US012718707B2

(12) United States Patent
Singapogu et al.

(10) Patent No.: US 12,718,707 B2
(45) Date of Patent: Aug. 25, 2026

(54) SUTURING SKILL SIMULATOR AND RELATED SYSTEMS AND METHODS

(71) Applicant: Clemson University Research Foundation, Clemson, SC (US)

(72) Inventors: Ravikiran Singapogu, Pendleton, SC (US); Richard Groff, Clemson, SC (US); Tanmay Kavathekar, Clemson, SC (US); Timothy C. Burg, Clemson, SC (US); Anand Jagannathan, Clemson, SC (US); Naren Nagarajan, San Francisco, CA (US); Irfan Kil, Foothill Ranch, CA (US); Simar Singh, Allen, TX (US); Jianxin Gao, Clemson, SC (US); Amir Mehdi Shayan, Seneca, SC (US); Zhanhe Liu, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 0 days.

(21) Appl. No.: 18/819,971

(22) Filed: Aug. 29, 2024

(65) Prior Publication Data

US 2025/0140132 A1 May 1, 2025

Related U.S. Application Data

(60) Provisional application No. 63/579,344, filed on Aug. 29, 2023.

(51) Int. Cl.
*G09B 23/34* (2006.01)
*A61B 17/04* (2006.01)

(52) U.S. Cl.
CPC .............. *G09B 23/34* (2013.01); *A61B 17/04* (2013.01)

(58) Field of Classification Search
CPC ..................................................... G09B 23/34
See application file for complete search history.

(56) References Cited

U.S. PATENT DOCUMENTS 8,834,170 B2 9/2014 Kurenov et al.
10,510,267 B2 12/2019 Jarc et al.
10,964,232 B2 3/2021 Rappel et al.
(Continued)

OTHER PUBLICATIONS

Kil et al., "Assessment of open surgery suturing skill: Simulator platform, force-based, and motion-based metrics" Frontiers in Medicine, vol. 9, Published Aug. 29, 2022, pp. 13.
(Continued)

*Primary Examiner* — Kesha Frisby
(74) *Attorney, Agent, or Firm* — Fredrikson & Byron, P.A.

(57) ABSTRACT

Suturing simulation systems and related methods comprising a table, a membrane housing associated with the table, a suturing membrane attached to the membrane housing, an internal camera disposed within the membrane housing, and at least one sensor associated with the table, wherein the internal camera and the at least one sensor are configured to collect suturing data. Other systems and methods include a data collection software module configured to synchronize the suturing image data from the internal camera and the suturing sensor data from the at least one sensor, thereby resulting in synchronized suturing data, and further can include a data processing software module configured process and extract metrics from the synchronized suturing data.

20 Claims, 30 Drawing Sheets

(56) References Cited

U.S. PATENT DOCUMENTS

| | | | |
|---|---|---|---|
| 2016/0314710 | A1 | 10/2016 | Jarc et al. |
| 2017/0140671 | A1 | 5/2017 | Chui et al. |

OTHER PUBLICATIONS

Shayan et al., "Measuring Hand Movement for Suturing Skill Assessment: A Simulation-Based Study" , Journal of Surgery, Nov. 2023, pp. 20.

Singh et al., "Objective and Automated Quantification of Instrument Handling for Open Surgical Suturing Skill Assessment: A Simulation-Based Study", IEEE Open Journal of Engineering in Medicine and Biology, vol. 5, 2024, pp. 485-493.

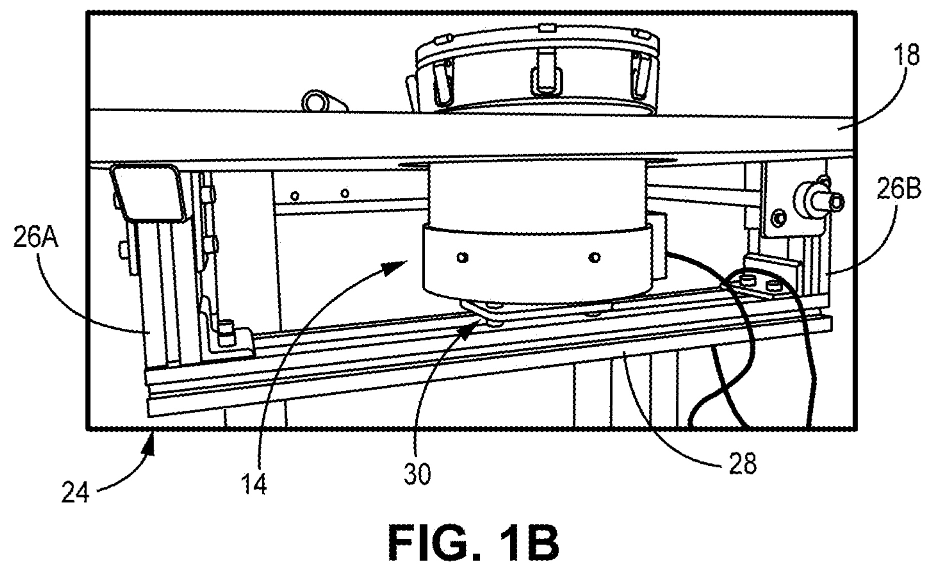
FIG. 1B
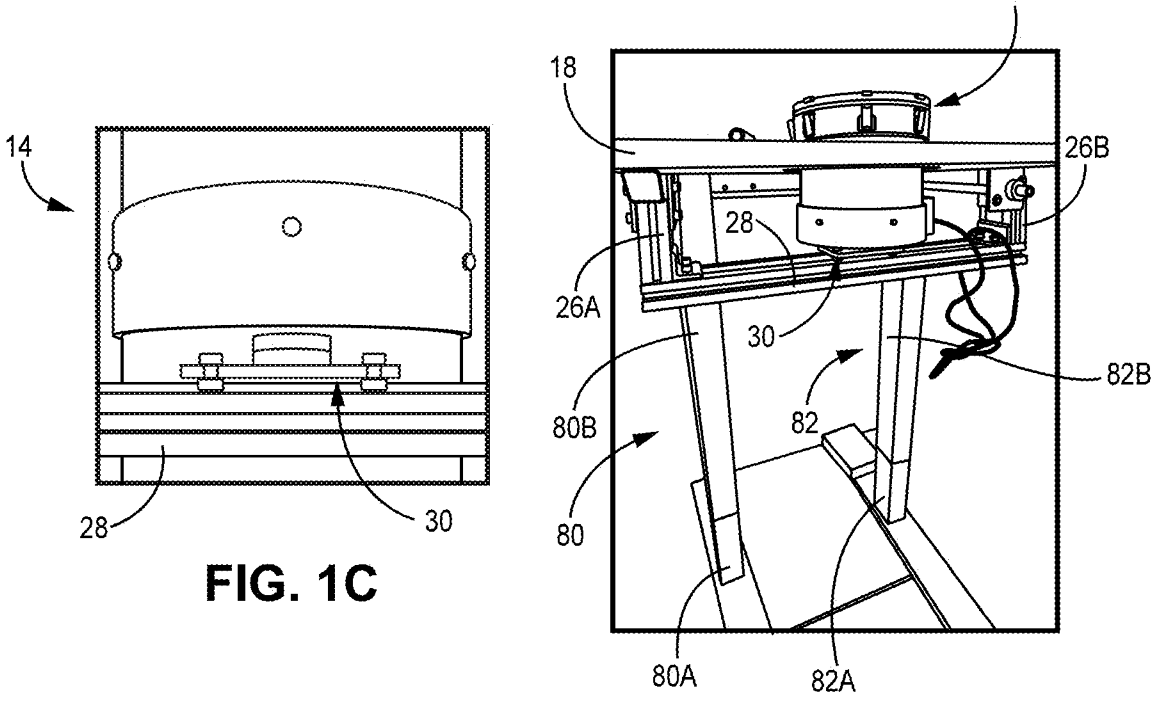
FIG. 1C
FIG. 1D

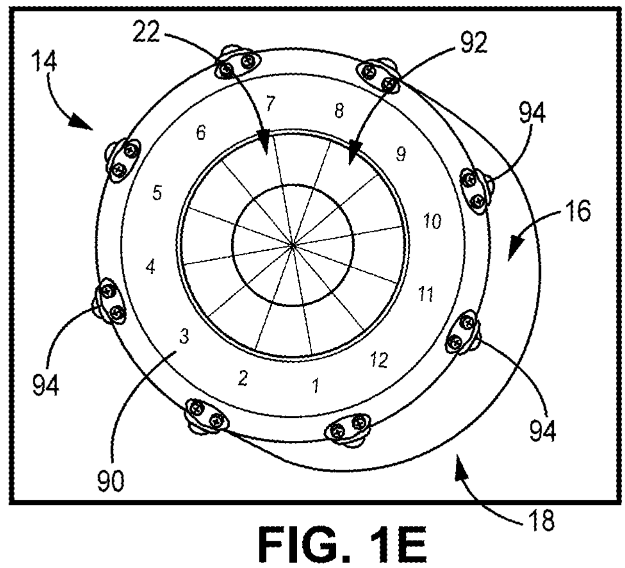
FIG. 1E
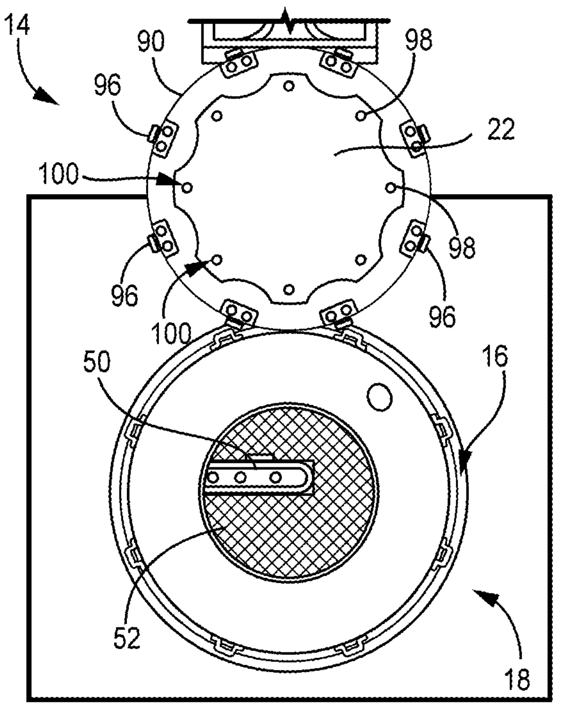
FIG. 1F
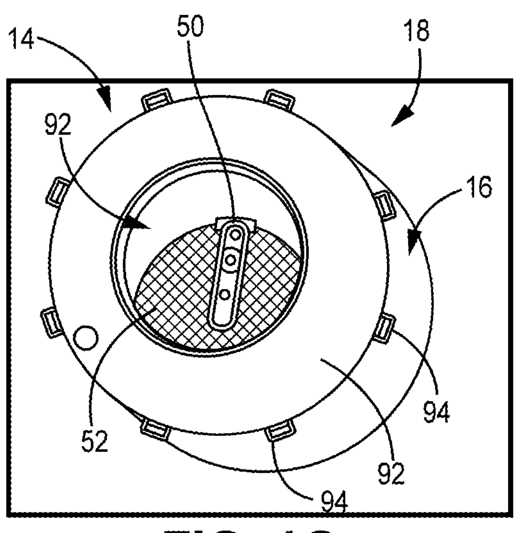
FIG. 1G

218
PITCH AXIS
ROLL AXIS

Roll Vel [rad/s]

4 2 0 -2 -4

14 15 16 17 18 19 20 21

Roll [rad]

1 0 -1

14 15 16 17 18 19 20 21

Time [s]

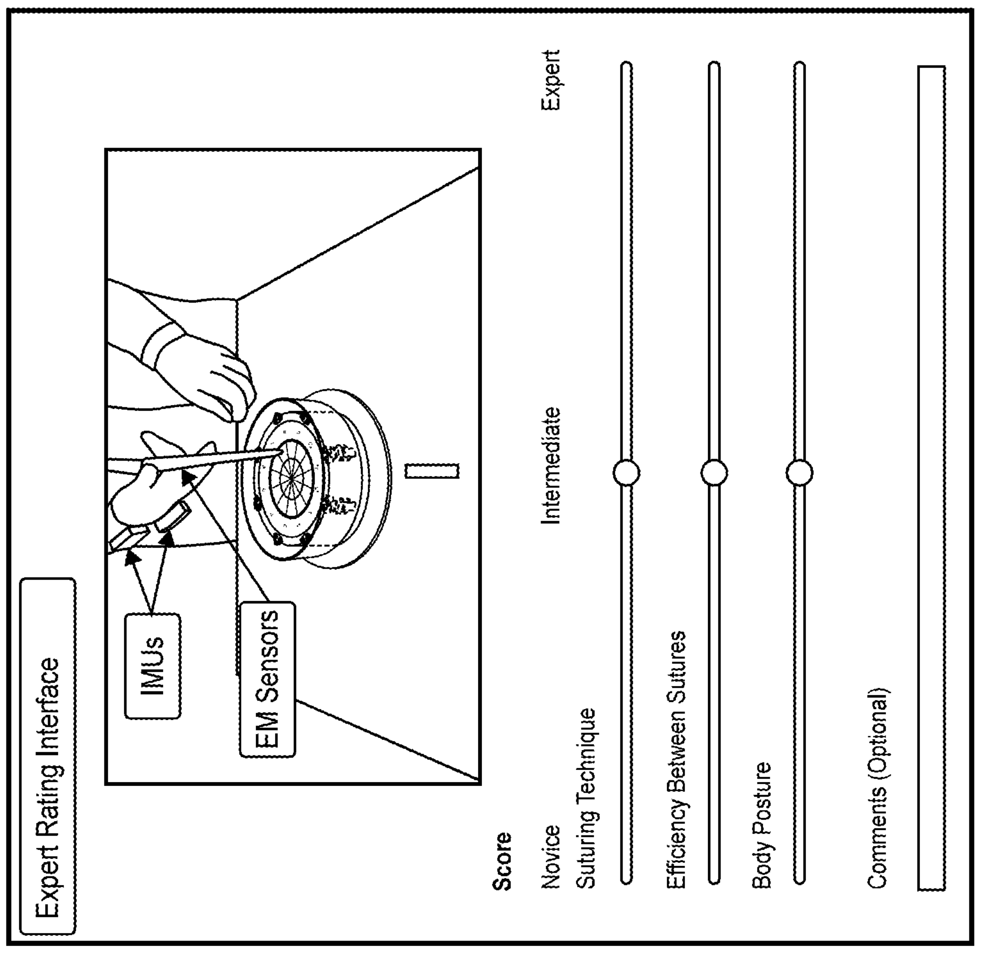
FIG. 22B
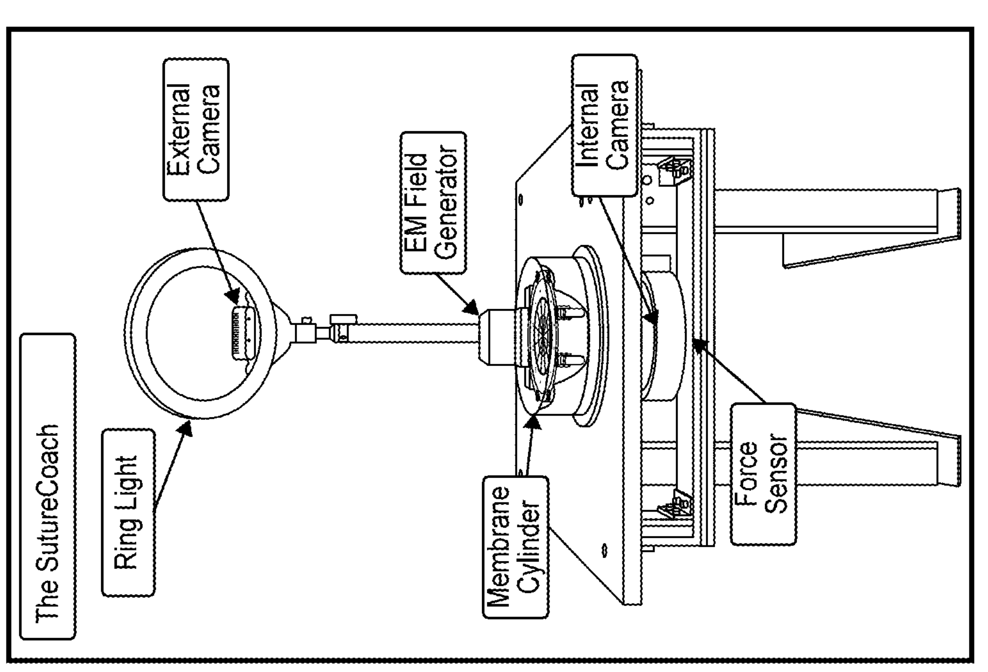
FIG. 22A

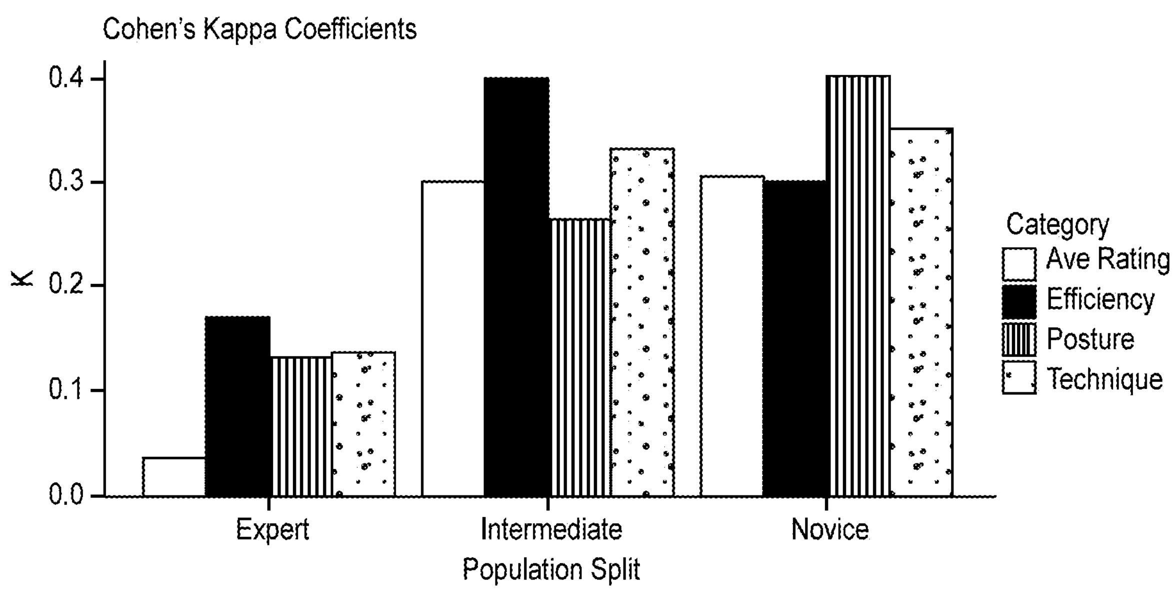

FIG. 26

Proof-of-Concept: Tailored Feedback to Improve SutureCoach Performance

1. Subject completes trial on the SutureCoach

2. Vote count classification of the trial.

Novice Split Decision Tree Classier 8 sutures are classified as unskilled.

The subject is considered unskilled

3. Which sutures were classified as unskilled?

12 11 1 10 2 9 3 8 4 7 5 6

4. Which metric decisions classified those sutures as unskilled?

S1: SA
S2: $LDLJ_{tool-t}$
S5: $LDLJ_{App}$
S6: AvgRoll
S8: $LDLJ_{App}$:T
S10: Pks, SA
S11: $LDLJ_{App}$
S12: $LDLJ_{App}$ 5. Example of how to translate these metrics into actionable feedback

| Metric | Feedback |
|---|---|
| SA | Minimize needle sway under the membrane. |
| $LDLJ_{tool-t}$ | Improve needle driver control. |
| $LDLJ_{App}$ | Improve needle driver efficiency approaching this suture. |
| AvgRoll | Larger, deliberate hand rotations. |
| T | Complete the suture faster. |
| Pks | Minimize shaky needle driver movement |

FIG. 27

SUTURING SKILL SIMULATOR AND RELATED SYSTEMS AND METHODS

CROSS-REFERENCE TO RELATED APPLICATION(S)

This application claims the benefit under 35 U.S.C. § 119 (e) to U.S. Provisional Application 63/579,344, filed Aug. 29, 2023 and entitled "Suturing Skill Simulator and Related Systems and Methods," which is hereby incorporated herein by reference in its entirety.

GOVERNMENT SUPPORT

This invention was made with government support under Grant No. 5R01HL146843-03, awarded by the National Institutes of Health. The government has certain rights in the invention.

FIELD

The various embodiments herein relate to surgical training tools, and especially to surgical simulators that provide objective measures of surgical skill.

BACKGROUND

Traditional surgical training shares many features in common with other apprenticeship-based skilled trades. Promotion is often based on duration of service rather than objective demonstration of specific objective performance metrics. This type of training may be highly subjective since feedback often depends on the expert surgeon's preferences and style. Further, training draws expert surgeons away from clinical responsibilities.

Objective measures of surgical skill have remained elusive because of a lack of consensus regarding the optimal metrics. Surgical trainees are often evaluated by surgical educators using subjective rating scales that often lack precision and reproducibility. Quantification of a surgeon's skill has received attention in recent years due to multiple factors including: duty hour restrictions on surgical residents, limited training opportunities, a call for the reduction in medical errors, and a need for structured training. Surgical skill is important due to the direct relationship between surgical performance and clinical outcomes such as hospital readmission and complication rates. Surgical outcomes may be improved through training to improve skill. For this purpose, surgical simulators-capable of simulating an aspect of a surgical procedure and of assessing and/or training the subject's skill on a given task—have been used in recent years.

Certain surgical simulators have been developed to aid surgeons-in-training in the acquisition of a wide range of surgical skills and to standardize and automate assessment of a surgeon's skill. Surgical simulators may be as basic as simple devices that allow surgeons to practice suturing of synthetic materials (e.g., sponges, plastic tubes) to highly sophisticated computer-based virtual operating rooms. However, simulation of open surgical techniques-such as, for example, suturing—has historically relied on the use of animal or cadaver labs which frequently lack object performance metrics.

Suturing is a fundamental surgical skill required in a variety of operations, ranging from wound repair in trauma care to delicate vascular reconstruction in vascular surgery. The process of suturing can be divided into the following phases: (i) puncturing a needle into the tissue perpendicularly, (ii) driving the needle through the tissue following the curvature of the needle, (iii) exiting the tissue from an exit point, and (iv) withdrawing the needle from the tissue completely prior to tightening the suture. Learning skilled suturing is essential for novice medical practitioners and has been incorporated into most fundamental skills training curricula, including, for example, the Fundamentals of Laparoscopic Surgery (FLS) and Fundamentals of Vascular Surgery (FVS) curricula. However, most currently available simulators for teaching suturing have been developed for minimally invasive surgery; only a handful of attempts have focused on open surgery. Furthermore, the majority of studies that examine suturing skill focus on product metrics, i.e., metrics based on analyzing the final results of the task (rather than the process of performing the task).

There is a need in the art for improved systems, methods, and devices for testing and quantifying suturing skills.

BRIEF SUMMARY

Discussed herein are various suturing simulation systems and methods, including such systems and methods that include a membrane housing, a suturing membrane, and two or more sensors and/or cameras that collect suturing-related data. Further embodiments relate to synchronization of the suturing-related data and calculation of objective metrics based on that synchronized data for assessing the suturing skills of a user.

In Example 1, a suturing simulation system comprises an adjustable table, a membrane housing associated with the adjustable table, a suturing membrane attached to the membrane housing, an internal camera disposed within the membrane housing, and a force/torque sensor operably coupled with the membrane housing, wherein the internal camera and the force/torque sensor are configured to collect suturing data.

Example 2 relates to the suturing simulation system according to Example 1, further comprising a motion sensor associated with the system, wherein the motion sensor is configured to collect suturing data.

Example 3 relates to the suturing simulation system according to Example 1, further comprising an external camera disposed above the membrane housing, wherein the external camera is configured to collect suturing data.

Example 4 relates to the suturing simulation system according to Example 1, further comprising a data collection software module configured to synchronize the suturing data from the internal camera and the force/torque sensor, thereby resulting in synchronized suturing data.

Example 5 relates to the suturing simulation system according to Example 4, wherein the data collection software module is configured to log the synchronized suturing data.

Example 6 relates to the suturing simulation system according to Example 5, further comprising a data processing software module configured to process image data in the synchronized suturing data.

Example 7 relates to the suturing simulation system according to Example 6, wherein the data processing software module is configured to extract metrics from the synchronized suturing data.

Example 8 relates to the suturing simulation system according to Example 1, further comprising at least one surgical depth cylinder removably positionable around the membrane housing.

Example 9 relates to the suturing simulation system according to Example 8, wherein the at least one surgical depth cylinder comprises a first surgical depth cylinder comprising a first height and a second surgical depth cylinder comprising a second height, wherein the second height is greater than the first height.

In Example 10, a suturing simulation and skills assessment system comprises a table comprising a height-adjustable tabletop, a membrane housing disposed through an opening in the tabletop, the membrane housing comprising a suturing membrane removably attached to the membrane housing, at least one removable surgical depth cylinder positionable around the membrane housing, an internal camera disposed within the membrane housing, wherein the internal camera is configured to collect suturing image data from an underside of the suturing membrane, at least one sensor associated with the table, wherein the at least one sensor is configured to collect suturing sensor data, a data collection software module configured to synchronize the suturing image data from the internal camera and the suturing sensor data from at least one sensor, thereby resulting in synchronized suturing data, and a data processing software module configured process and extract metrics from the synchronized suturing data.

Example 11 relates to the suturing simulation and skills assessment system according to Example 10, wherein the at least one sensor comprises a force/torque sensor operably coupled with the membrane housing.

Example 12 relates to the suturing simulation and skills assessment system according to Example 10, wherein the at least one sensor comprises a motion sensor associated with the system, wherein the motion sensor is attachable to a hand or wrist of a user.

Example 13 relates to the suturing simulation and skills assessment system according to Example 10, wherein the at least one sensor comprises a tool motion sensor associated with the system, wherein the tool motion sensor is attachable to a suturing tool.

Example 14 relates to the suturing simulation and skills assessment system according to Example 10, further comprising an external camera disposed above the membrane housing, wherein the external camera is configured to collect suturing image data from a top side of the suturing membrane.

Example 15 relates to the suturing simulation and skills assessment system according to Example 10, wherein the at least one removable surgical depth cylinder comprises a first surgical depth cylinder comprising a first height and a second surgical depth cylinder comprising a second height, wherein the second height is greater than the first height.

In Example 16, a method of assessing suturing skills of a user comprises providing a simulation system comprising a table comprising a height-adjustable tabletop, a membrane housing disposed through an opening in the tabletop, the membrane housing comprising a suturing membrane removably attached to the membrane housing, an internal camera disposed within the membrane housing, at least one sensor associated with the table, a data collection software module configured to synchronize the suturing image data from the internal camera and the suturing sensor data from at least one sensor, thereby resulting in synchronized suturing data, and a data processing software module configured process and extract metrics from the synchronized suturing data. The method further comprises having a user perform a suturing exercise on the suturing membrane, collecting suturing image data relating to the suturing exercise from an underside of the suturing membrane via the internal camera, collecting suturing sensor data relating to the suturing exercise via the at least one sensor, synchronizing the suturing image data and the suturing sensor data, thereby resulting in synchronized suturing data, processing and extracting metrics from the synchronized suturing data, and assessing a suturing skillset of the user via the metrics from the synchronized suturing data.

Example 17 relates to the method according to Example 16, further comprising determining a depth of the suturing exercise by selecting a removable surgical depth cylinder based on a height of the at least one removable surgical depth cylinder and positioning the removable surgical depth cylinder around the membrane housing.

Example 18 relates to the method according to Example 16, further comprising comparing the suturing skillset of the user to a suturing skillset of another user.

Example 19 relates to the method according to Example 16, further comprising determining whether to certify the user based on the suturing skillset of the user.

Example 20 relates to the method according to Example 16, further comprising providing feedback to the user based on the metrics from the synchronized suturing data.

While multiple embodiments are disclosed, still other embodiments will become apparent to those skilled in the art from the following detailed description, which shows and describes various illustrative implementations. As will be realized, the various embodiments herein are capable of modifications in various obvious aspects, all without departing from the spirit and scope thereof. Accordingly, the drawings and detailed description are to be regarded as illustrative in nature and not restrictive.

BRIEF DESCRIPTION OF THE DRAWINGS

FIG. 1B is a perspective side view of a membrane housing disposed through a tabletop of the system of FIG. 1A, according to one embodiment.

FIG. 1C is a close-up view of the membrane housing and a force/torque sensor of the system of FIG. 1A, according to one embodiment.

FIG. 1D is a perspective view of the table with adjustable legs of the system of FIG. 1A, according to one embodiment.

FIG. 1E is a top perspective view of the membrane housing and suturing membrane of the system of FIG. 1A, according to one embodiment.

FIG. 1F is top view of the membrane housing with the lid open in the system of FIG. 1A, according to one embodiment.

FIG. 1G is a perspective view of the top of the membrane housing of the system of FIG. 1A, according to one embodiment.

FIG. 19 shows confidence intervals of Tukey HSD pairwise comparisons for EM metrics for from sensor 1, according to one embodiment. Surface and depth intervals are plotted side-by-side and are denoted with a blue Δ and a yellow ∇, respectively. E, I, and N are shorthand for expert, intermediate, and novice, with corresponding comparisons marked with a.

FIG. 22A is a front perspective view of a suturing simulator platform detailing the placement of various sensors and equipment, according to one embodiment.

FIG. 22B is top perspective view of the EM sensors and the IMUs of the platform of FIG. 22A, according to one embodiment. Below that view is a screenshot of the expert rating survey interface used to gather expert ratings. Raters can use sliders on each skill category to evaluate a subject's performance on a scale from novice to expert.

FIG. 26 is a bar graph comparing each classifier's Cohen's kappa coefficient, grouped by population split, according to one embodiment. A higher coefficient value indicates better classification performance.

FIG. 27 is a flowchart illustrating how one embodiment of a suturing simulation system provides tailored feedback based on a subject's skill level based on Average Rating. (1.) The subject completes a trial on the system. (2.) Their performance data is analyzed by the vote count algorithm to determine their skill level. (3.) The algorithm will evaluate which sutures were considered unskilled, and (4.) extract specific metric-based decisions that failed the subject (5.) Finally, the system will provide targeted feedback on factors to improve performance at those locations.

DETAILED DESCRIPTION

Figure 1A:
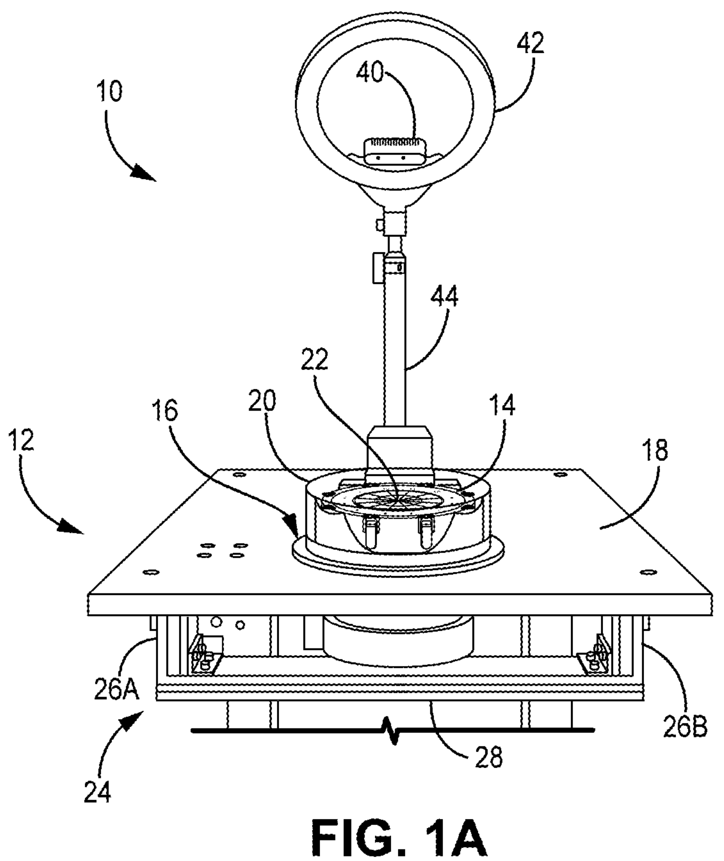
FIG. 1A is a perspective front view of a system for assessing suturing skills, according to one embodiment.

The various embodiments disclosed or contemplated herein relating to suturing simulator systems and methods of objectively testing suturing skills using such systems, including open surgery suturing skills. In some implementations, suturing simulator systems are provided that use multiple sensors and other data collection devices to collect synchronized force, motion, touch, and video data as a user (such as a trainee) performs a prespecified suturing task. Further, certain simulator embodiments are configured to simulate suturing at various depth levels, which can represent surgery inside a body cavity or at the surface. In addition, according to various implementations, certain suturing skill testing methods can use various metrics to provide objective analysis of suturing skill, including force metrics (force and torque in z direction), motion metrics (yaw, pitch, roll), physical contact metrics, and image-enabled metrics (orthogonal and tangential forces). That is, data collected from the various sensors and data collection devices of a suturing simulator according to the various embodiments herein can produce metrics for objectively quantifying suturing skill for a user and further for comparing skill levels between or among different users. Thus, the simulator systems and related methods can be used to assess and teach open surgery suturing skills, and further can be used by certifying organizations, credentialing committees, and surgical educators in addition to providing surgeons in training with objective feedback.

According to some embodiments, one advantage of the various simulator systems herein is that they utilize standard surgical tools (such as, for example, a standard needle holder, a standard needle with surgical thread, etc.), in contrast to known simulators that require the use of modified surgical tools. Another advantage relates to the adjustability of the simulator embodiments herein to allow for simulating different depth levels, because suturing at depth is especially important in certain types of procedures (such as, for example, vascular surgery) and requires significantly different and less intuitive hand motions as compared to suturing at the surface. A further advantage relates to the various sensors and collection devices and the resulting various metrics that can be calculated and tracked by the various systems herein, including the combination of force data with computer vision information to provide a measurement of suturing skill. Additionally, the various suturing simulator system embodiments herein also provide the advantages of training surgical skills without the use of humans or animals and the ability to objectively measure skill and its progression over time.

One embodiment of a suturing simulation system 10 is depicted in FIGS. 1A-1G. In this implementation, the system 10 includes a table 12, a membrane housing 14 disposed through an opening 16 in the tabletop 18, and a removable surgical depth cylinder 20 disposed around the membrane housing 14. The membrane housing 14 has a suturing membrane 22 removably attached to the top of the housing 14 such that it is accessible to a user for performing suturing exercises on the membrane 22 as will be described in additional detail below.

According to certain embodiments, the table 12 has a frame 24 to which the tabletop 18 is coupled. The frame 24 has two vertical bars 26A, 26B attached to the tabletop 18 and a horizontal bar 28 that is coupled to (or integral with) the two vertical bars 26A, 26B. In addition, as best shown in FIGS. 1B-1D, the membrane housing 14 is coupled to the horizontal bar 28 via a force and/or torque sensor 30 such that the sensor 30 can be used to detect the force and/or torque applied by the user (via a suturing needle) during the suturing exercises, as will be discussed in further detail below). In other words, the membrane housing 14 is disposed through the opening 16 such that the housing 14 is not attached to or in contact with the tabletop 18 and instead is coupled to the table 12 solely via the sensor 30 attached to the horizontal bar 28, thereby ensuring accurate measurement of any force and/or torque applied to the membrane 22 (and thus the housing 14) by the user. Alternatively, any configuration of the table 12, frame 24, and/or the housing 14 is contemplated that allows the membrane housing 14 to have one or more force/torque sensors to accurately measure force/torque. In one embodiment, the force/torque sensor 30 is a 6-axis force/torque sensor for measuring any and all force and torque applied to the membrane 22 during suturing. One specific exemplary sensor 30 is the ATI MINI 40, which is commercially available from ATI Industrial Automation, Inc. in Apex, NC. Alternatively, any known force/torque sensor that can be used to obtain similar measurements can be used.

Further, the system 10 can also have an external camera 40 disposed above membrane housing 14 as shown in FIG. 1A to capture images-still and/or video—of the user's hand movement and suturing tool(s) while the user performs a suturing exercise on the membrane 22. One exemplary camera embodiment can capture images at 30 fps. In one embodiment, an adjustable camera arm 44 is attached to the table 12 at one end and having the camera 40 attached at the other end such that the camera arm 44 can be used to optimize the positioning of the camera 40 to capture the membrane 22 and all movements of the user's hand and instrument(s) during suturing. According to certain implementations, the system 10 can also have a ring light 42 that is also coupled to the camera arm 44 and used in conjunction with the camera 40 to ensure consistent and/or optimal lighting for capturing the images. In one specific example, the camera 40 is a C920 HD USB 2.0, which is commercially available from Logitech International S. A. in Lausanne, Switzerland. Alternatively, any known camera and/or camera and ring light combination (or separate ring light) for use in capturing images in a similar fashion can be used herein.

In accordance with various implementations, the system 10 can also have an internal camera 50 disposed within the cylindrical housing 14 such that the camera 50 is positioned below and aimed up at the underside of the membrane 22, as best shown in FIGS. 1F and 1G. In this position, the internal camera 50 is intended to capture images of the underside of the membrane 22 and, more specifically, needle and thread movement (subcutaneous movement) underneath the membrane 22 during suturing. In one specific implementation, the camera 50 can record the needle and suture motion at 60 fps. Further, in certain embodiments, the camera 50 can have a software interface such as, for example, FlyCapture SDK. One exemplary internal camera is the Firefly MV USB 2.0, commercially available from Point Grey Research Inc., in British Columbia, Canada. Another camera that can be used is the Intel RealSense D435. Alternatively, any known camera for use to capture the images as described herein can be used.

Certain embodiments can also include one or more lights 52 (as best shown in FIGS. 1F and 1G) disposed within the cylindrical housing 14 as well to provide consistent lighting conditions for capturing the images of the underside of the membrane 22. In one specific implementation, the lights 52 are white LED strips 52 positioned at or near the bottom of the interior of the housing 14 such that the camera 50 is disposed between the lights 52 and the member 22 as shown. Alternatively, the one or more lights 52 can be any known lights that can be used to provide consistent lighting within the housing 14.

Figure 2A:
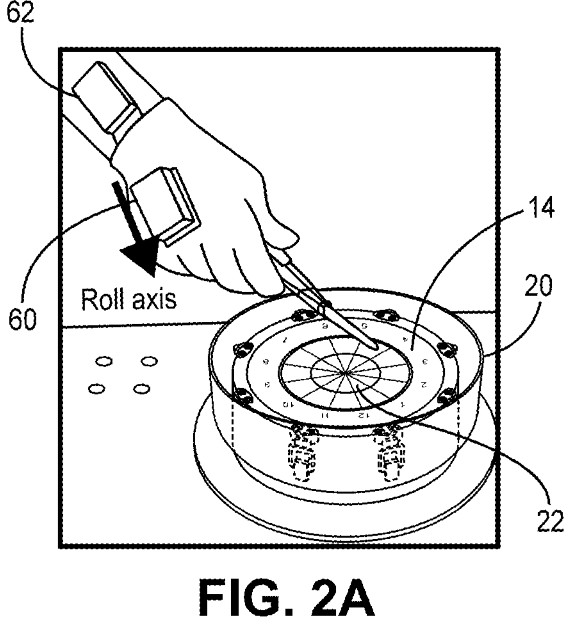
FIG. 2A is a perspective view of a user performing a suturing exercise on a suturing membrane with a first surgical depth cylinder disposed around the membrane housing, according to one embodiment.

The system 10 can also have hand/wrist motion sensors attached to the user, according to some implementations. More specifically, as shown in FIG. 2A, one motion sensor 60 is attached to the hand of the user, while a second motion sensor 62 is attached to the wrist of the user. Alternatively, in certain embodiments, only one sensor is used, and it's the motion sensor 60 attached to the hand. Each hand/wrist motion sensor 60, 62 (or the single sensor 60) is attached as shown (with sensor 60 attached to the dorsum of the user's hand and sensor 62 attached to the top of the user's wrist) and, in a specific implementation, can be logged at 200 Hz during suturing. In one embodiment, each motion sensor 60, 62 is an inertial measurement unit (IMU) 60, 62 that is used to track the motion of the user's hand and wrist, respectively, during the suturing exercise. One exemplary IMU that can be used for the motion sensors 60, 62 is an InertiaCube4 sensor, which is commercially available from InterSense Inc. in Billerica, MA. Further, in certain specific embodiments, InterSense SDK can be used to obtain yaw, pitch, and roll measurements of the subject's wrist motion.

Figure 17A:
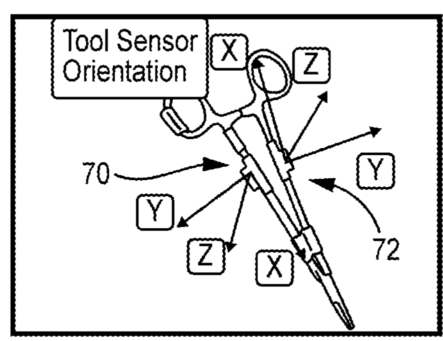
FIG. 17A depicts the titanium needle driver with the EM sensor attachment and orientations, according to one embodiment.
Figure 17B:
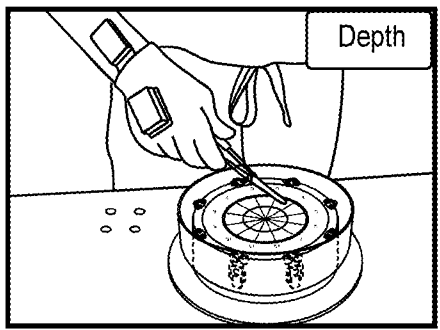
FIG. 17B depicts an expert subject suturing at the surface and depth conditions, according to one embodiment.
Figure 17C:
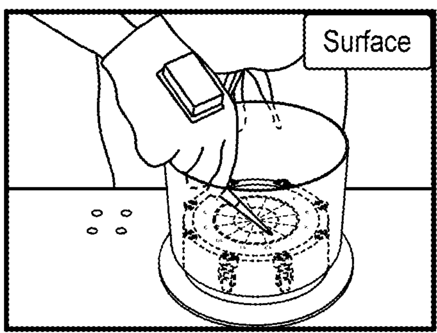
FIG. 17C depicts an expert subject suturing at the surface and depth conditions, according to one embodiment.
Figure 17D:
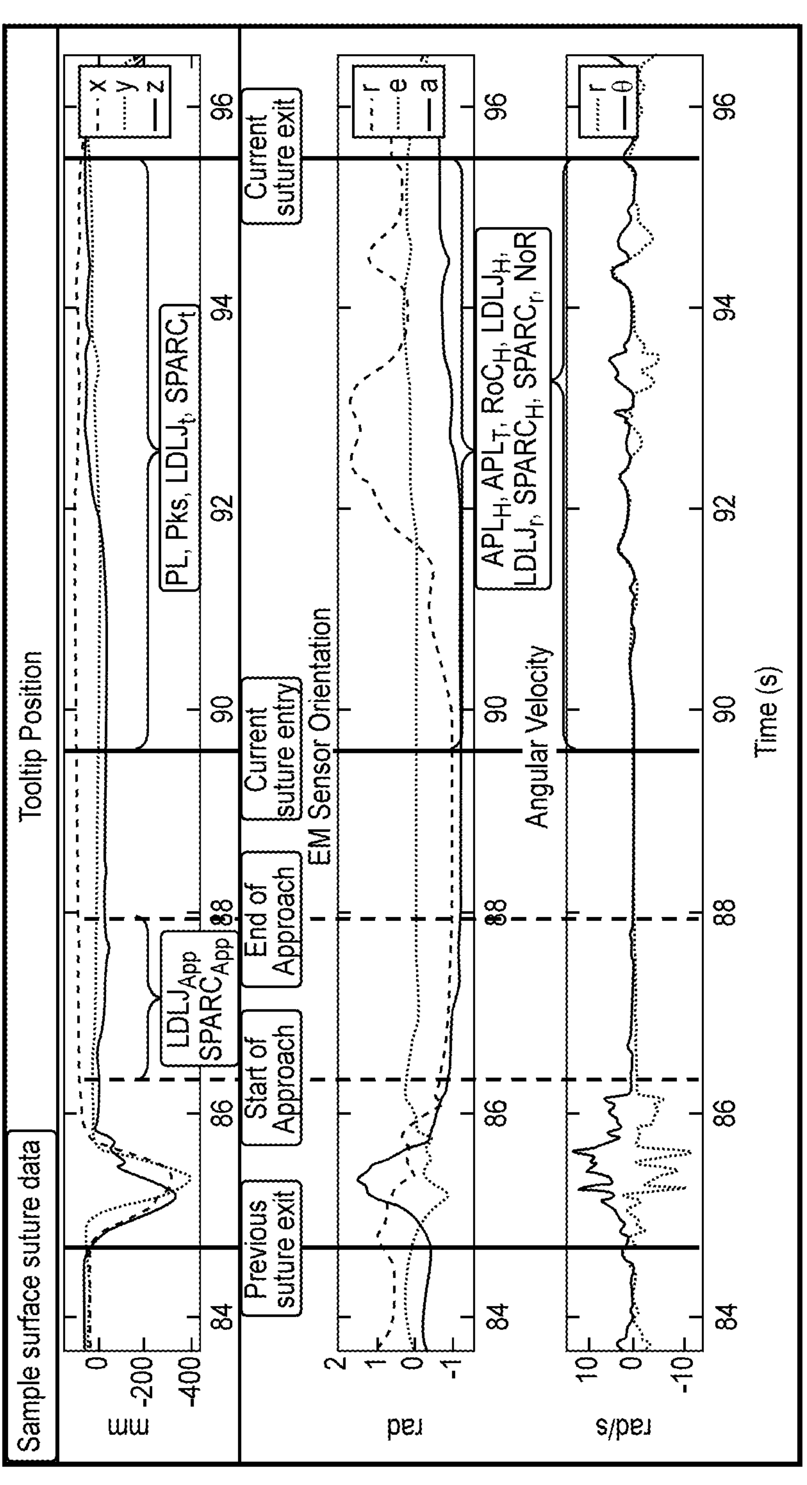
FIG. 17D depicts a graphical representation of sample tooltip position, orientation, and angular velocity profiles across a suture alongside sections of data that metrics are calculated on, according to one embodiment.
Figures 24A, 24B, 24C, 24D, 24E:
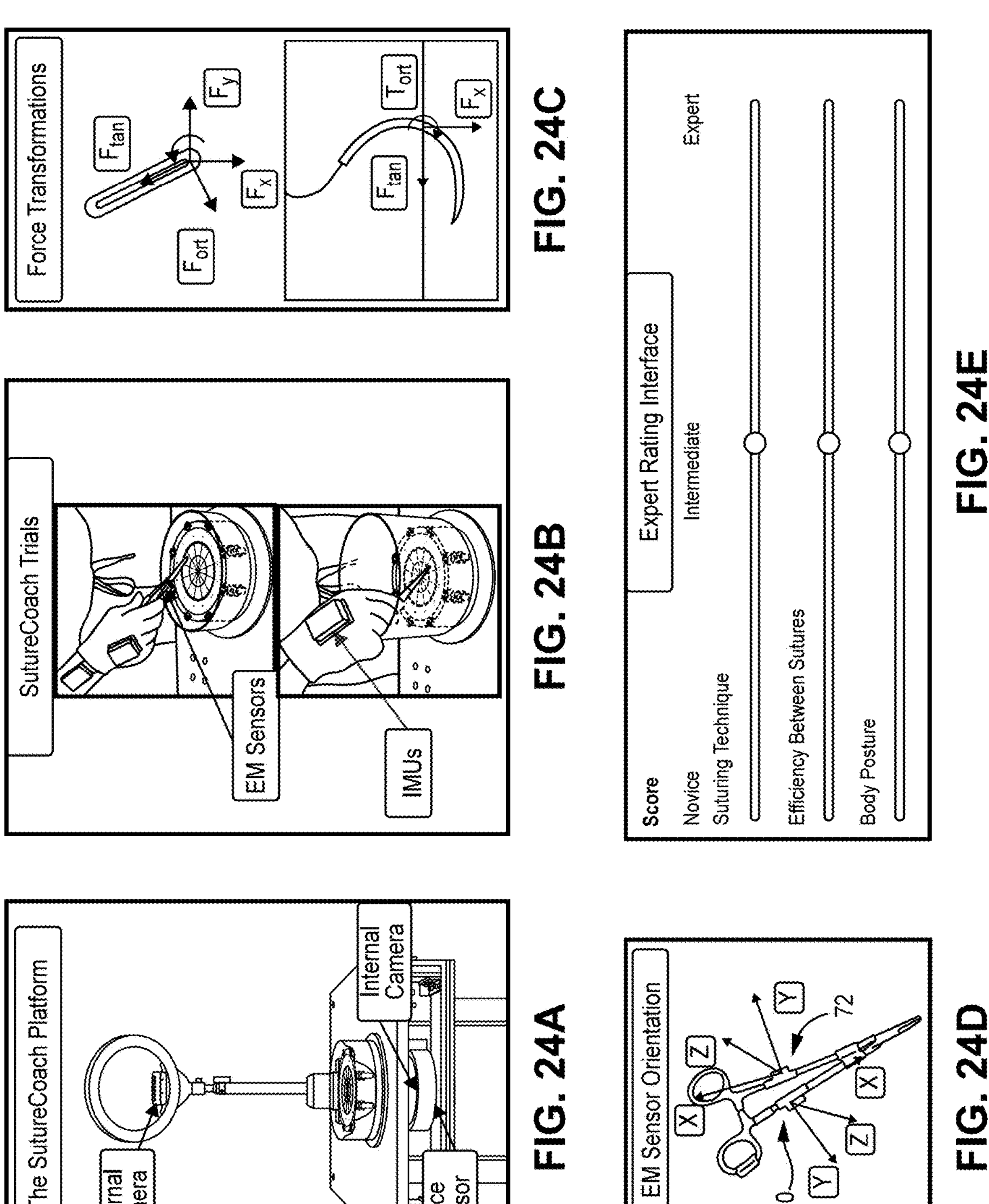
FIG. 24A is a front view of a suturing simulator, according to one embodiment.
FIG. 24B depicts a subject suturing under surface (top) and a depth (bottom) conditions, according to one embodiment.
FIG. 24C The top figure is a bottom-up view of a suturing needle (the image is transformed for better illustration) showing the critical tangential and orthogonal force transformations relative to the force/torque sensor's x and y directions. The bottom figure illustrates a side-view (bottom) representing the orthogonal torque transformation.
FIG. 24D is a perspective view of the needle driver and its two EM sensors and their relative orientations. Sensor 2 is transformed to match sensor 1.
FIG. 24E is an exemplary image of the expert rating interface, according to one embodiment.

Alternatively, or in addition to the hand/wrist motion sensors (such as sensors 60, 62) as discussed above, the system 10 can also have tool motion sensors 70, 72 as best shown in FIGS. 17A and 24D, according to one embodiment. In one embodiment as shown, the two sensors 70, 72 are attached to the handles of a suturing tool (in this specific example, a needle driver). More specifically, one sensor 70 is attached to one handle, and the other sensor 72 is attached to the second handle as shown. In embodiment, the tool motion sensors 70, 72 are electromagnetic position and orientation sensors. In one specific example, each of the two sensors 70, 72 can be an Ascension trakSTAR™ Model 180, which is commercially available from Northern Digital Inc. in Waterloo, ON, Canada.

According to certain embodiments, the tool motion sensors 70, 72 can be attached to the needle driver in a non-intrusive manner for the surgeon to feel comfortable using instrument handling techniques identical to those in the operating room. In one specific implementation, each sensor 70, 72 can be secured to the tool through a molded 3D-printed casing and lid that is affixed to each handle of the needle driver.

Figure 2B:
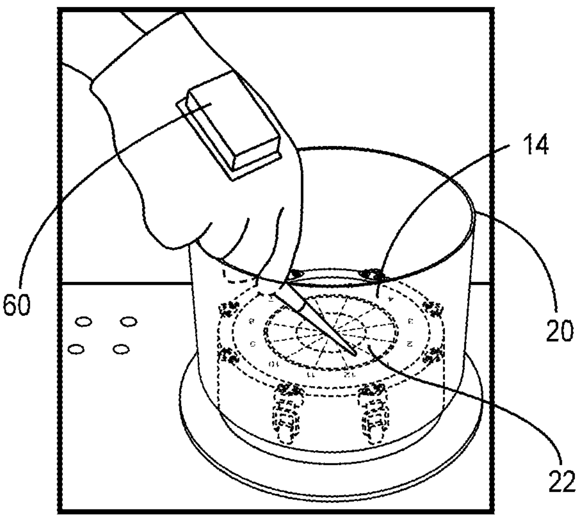
FIG. 2B is a perspective view of a user performing a suturing exercise on a suturing membrane with a second surgical depth cylinder disposed around the membrane housing, wherein the second surgical depth cylinder has a greater height that the first surgical depth cylinder of FIG. 2A, according to one embodiment.

As best shown in FIGS. 2A and 2B, the removable surgical depth cylinder 20 can be used in the system 10 to simulate suturing at different depths, according to one embodiment. In other words, multiple different removable cylinders 20 can be provided having different heights, each of which can be optionally disposed around the housing 14 to simulate a specific depth, thereby forcing the user to access the membrane 22 within the cylinder 20 at that depth in a fashion similar to the depth that might be experienced in a real open surgery. In the exemplary embodiment as shown in FIGS. 2A and 2B, two different cylinders 20 are provided, with the cylinder 20 in FIG. 2A having a height that is substantially similar to the height of the membrane 22, thereby replicating a surface surgery, while the cylinder 20 in FIG. 2B has a height that is higher than the membrane 22, thereby replicating a depth surgery. Alternatively, a number of cylinders 20 of different heights can be used in conjunction with the system 10 such that users can be exposed to simulated surgeries at multiple different depths. More specifically, the number of cylinders 20 of different heights that are provided with the system 10 can be two cylinders (as shown), three cylinders, four cylinders, five cylinders, six cylinders, or any number of cylinders of different heights. As such, the system 10 allows for the selection of a specific cylinder 10 to simulate a specific depth as needed.

According to certain embodiments, the removable depth cylinder 20 can also have one or more touch sensors coupled thereto for detecting contact between the user's hand or tool and the cylinder 20. For example, in one exemplary implementation, the touch sensor can be a flexible conductive film (not shown) that can line the interior and the top of the cylinder 20, with the film coupled to a capacitive sensing circuit such that any contact of the interior or top of the cylinder 20 by the user or the tool would be detected. In one embodiment, the flexible conductive film can be an Indium Tin Oxide coated plastic sheet, aluminum foil, or some combination of both. Further, in certain implementations, an Arduino can be coupled to the circuit to collect the contact information.

Certain simulation system 10 embodiments can also include a table 12 that has an adjustable height to allow for the table 12 to be adjusted to accommodate the comfort or needs of the specific user. In one embodiment, as best shown in FIG. 1D, the table 12 can have two adjustable legs 80, 82. More specifically, each leg 80, 82 has a bottom section 80A, 82A and an extendable top section 80B, 82B as shown. Thus, the height of the tabletop 18 above the floor can be adjusted by actuating the top sections 80B, 82B of the legs 80, 82 to move up or down as needed by the user, thereby resulting in the tabletop 18 being moved to the desired height. Alternatively, any known configuration or mechanism can be used to allow for the adjustability of the tabletop 18 height.

Returning to the cylindrical housing 14, additional features according to various embodiments are shown in FIGS. 1E-1F. In one implementation, the housing 14 has a lid 90 with an opening 92 defined therethrough such that the membrane 22, when attached, is accessed by the user through the opening 92. In certain embodiments, the lid 90 is rotatably movable between an open position (as shown in FIG. 1F) and a closed position (as shown in FIG. 1E) such that the interior of the housing 14 can be accessed when the lid 90 is in the open position and such that the membrane 22 can be used for suturing exercises when the lid 90 is in the closed position (and a membrane 22 is attached thereto). When the lid 90 is closed, the lid 90 can be firmly attached to the rest of the housing 14 using the latches 94 as best shown in FIG. 1E. The latches 94 are coupled to the cylindrical housing 14 such that each latch 94 can couple to a corresponding latch hook 96 on the lid 90 (as best shown in FIG. 1F). Alternatively, the lid 90 can be attached to the housing 14 via any known attachment mechanisms. In one embodiment as shown, the housing 14 has eight latches 94. Alternatively, the housing 14 can have one, two, three, four, five, six, seven, nine, ten, or any number of latches 94.

According to one embodiment, the membrane 22 can be attached to the housing 14 in the following fashion. First, the lid 90 is moved into the open position as best shown in FIG. 1F. At this point, a membrane 22 can be attached to the underside of the lid 90 via membrane hooks 98 disposed on the underside of the lid 90. More specifically, the membrane 22 can have holes 100 defined around the periphery of the membrane 22 that correspond to the hooks 98 on the underside of the lid 90. As such, the membrane 22 can be positioned against the lid 90 such that the membrane hooks 98 can be positioned through the corresponding openings 100, thereby attaching the membrane 22 to the underside of the lid 90. Once the membrane 22 is attached, the lid 90 can be moved back into its closed position.

In certain implementations, the membrane 22 can be made of a material such as GoreTex® or artificial leather. Alternatively, the membrane 22 can be made of any similar known fabric that can simulate tissue and can be used for simulated suturing.

In certain embodiments herein, a suturing exercise is performed on the membrane 22. According to some implementations, the exercise is the same as or similar to the radial suturing task in the Fundamentals of Vascular Surgery. Thus, as best shown in FIG. 5C, the membrane 22 can be designed such that suturing is performed in a radial and uninterrupted fashion. More specifically, a circle 110, representing an incision, is drawn or otherwise placed on the membrane 22, and the circle 110 is partitioned by radial lines 112 into equal sections each spanning 30° (similar to a clock face). Further, needle entry points 114 can be marked on the radial lines 112 as shown. In one embodiment, the distance of the entry mark 114 from the incision line 110 is based on the diameter of the needle. Thus, the marks can indicate where suturing is to be performed (entry on one side, exit on the other). Alternatively, the membrane 22 can be marked in any fashion and/or used in any fashion to allow for the performance and analysis of suturing skills.

Thus, the various system 10 embodiments disclosed or contemplated herein have multiple different sensors and other data collection devices (such as cameras) to collect data relating to a user's suturing exercise. More specifically, the data collection devices can collect force (via the force sensor 30), motion (via the motion sensors 60, 62, 70, 72), image (via cameras 40, 50), and, in some embodiments, touch data (via the capacitive touch sensors on the cylinder 20), thereby resulting in force-based metrics, motion-based metrics, image-based metrics, and, in some embodiments, touch-based metrics. That is, the system 10 has a suite of data collection devices to capture various possible aspects of skill: needle driver motions (tracked by motion sensors 70, 72), hand motion (tracked by motion sensors 60, 62 and camera 40), membrane forces and torques (tracked by force/torque sensor 30), and subcutaneous suture movement (tracked by internal camera 50).

Figure 7:
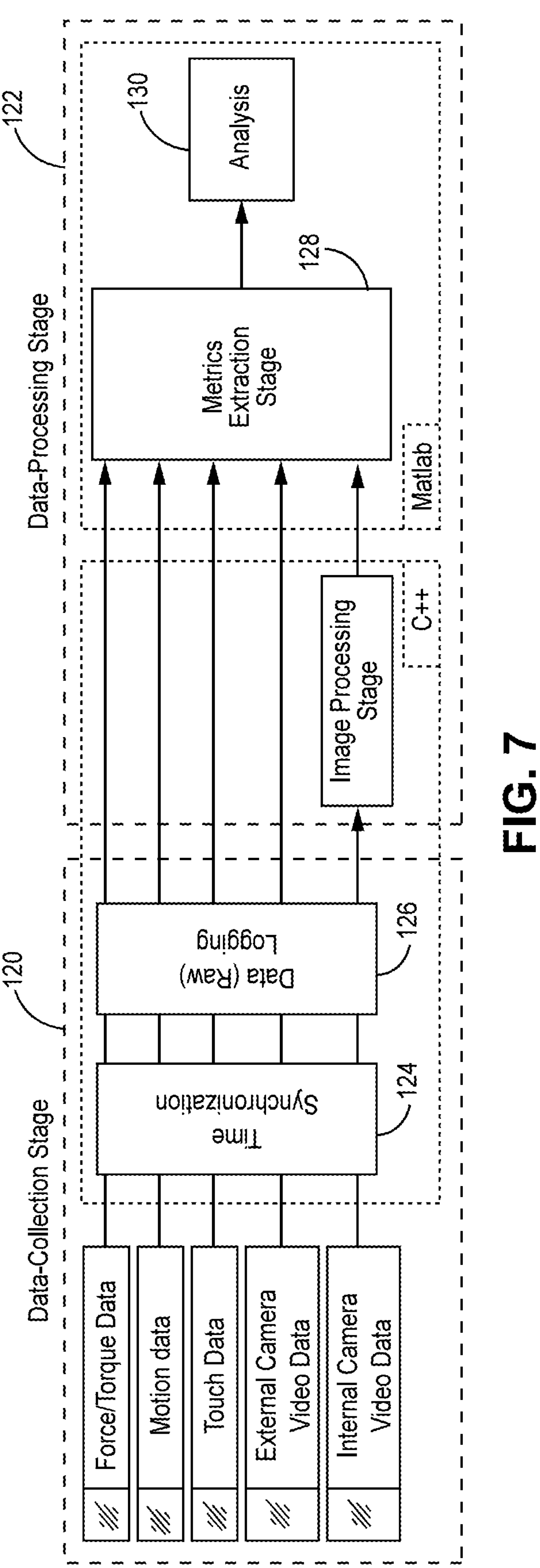
FIG. 7 is a flow chart depicting the data collection and data processing stages of a method of collecting suturing data from a suturing simulator and generating metrics relating to that suturing data, according to one embodiment.

In use, the system 10 can be operated in the following fashion as depicted in the flow chart of FIG. 7, according to one embodiment. The system 10 can operate in two main stages: the data collection stage 120 and the data processing stage 122. In the data collection stage 120, the system 10 synchronizes 124 and logs 126 the unprocessed (raw) force, motion, video, and touch data (collected from the data collection devices) as discussed above in real time during suturing.

In one embodiment, the logging step 126 makes it possible to revisit the collected raw data at any time for additional investigation and/or analysis.

Returning to the data collection stage 120, in one embodiment, the force/torque data can be logged at 1 KHz during suturing. In certain exemplary implementations, the data is obtained from the sensor (such as sensor 30) using software written using the NI-DAQ Software Development Kit (SDK), and in certain embodiments can be filtered offline, in one specific instance with a 10th-order Butterworth lowpass zero-phase filter with a cutoff frequency of 50 Hz to remove noise and smooth the data.

As mentioned above, in certain embodiments, the data collection is synchronized prior to post-processing. More specifically, in one exemplary implementation, the data is synchronized on a computer using a multithreaded implementation and timestamping. Alternatively, any known synchronization process can be used. In certain embodiments, the data collection stage 120 software can be written in C++ using Microsoft Visual Studio 2013. Alternatively, any appropriate software can be used to create the necessary software.

The raw, synched data can then be used in the data processing stage 122. Then, in the data processing stage 122, the collected data is used to extract metrics of suturing skill 128 and those metrics are analyzed 130. Further, before the extraction stage 128, the internal video (from one or both of the internal and external cameras 40, 50) is first processed with a computer vision algorithm to obtain information about needle and thread movement. This information is then used to identify the individual suture cycles. Thus, the collected raw data and the information about the individual suture cycles can be used to extract metrics 128 for each time the subject is actively suturing.

According to one embodiment, the individual suture cycles can be calculated in the following fashion. A single cycle can be divided into two distinct periods of time: active suturing time and idle time. Active suturing time is the time between needle entry into the membrane and complete needle removal from the membrane. Idle time is the time between the end of one active suturing time to the start of the next. In other words, active suturing is the time taken by subjects to complete one suture, whereas idle time is the time spent preparing for the next suture. Active suturing time may be further broken down into 4 phases: a) entry phase-puncturing the needle into the tissue; b) driving phase—driving the needle along some path under the membrane; c) exit phase-exiting the needle tip from the tissue; and d) pull-out phase—pulling the needle completely from the tissue and then tightening the thread. Dividing each suture cycle into distinct phases allows for context-specific interpretation of the sensor data. Needle entry and exit times obtained from the computer vision algorithm were used to extract each suture cycle for individual analysis.

Figure 8:
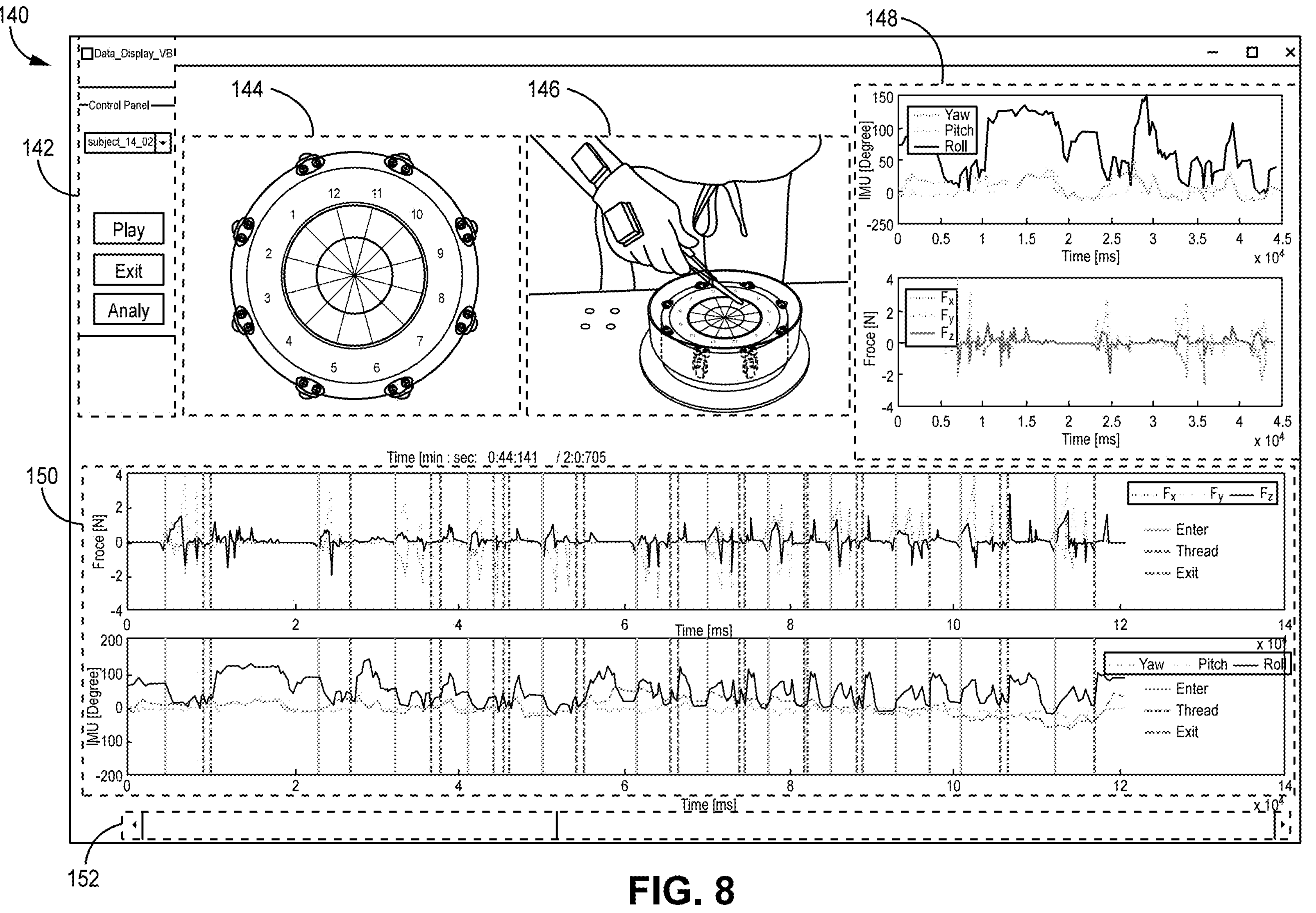
FIG. 8 is a graphical user interface of a suturing simulator system that is displaying synchronized data and images, according to one embodiment.

According to certain embodiments, the system 10 can also have a graphical user interface 140, as shown in one example in FIG. 8. The interface 140 can display a control panel 142, video from the internal camera 144, video from the external camera 146, real-time synchronized motion and force data in graphical representation 148, and synchronized force and motion data in graphical representation for the entire testing duration 150. In addition, the interface 140 can have an interactive slide 152 that allows a user to interactively explore the synchronized data by simply moving the slide 152 to a desired point in the synchronized data such that the graphical displays of data depict the data for the particular time chosen via the slide 152. Alternatively, the interface 140 can present any subset of this information and/or can present the information in a different configuration.

Further, in certain embodiments, the interface 140 can also label the needle entry, needle exit and thread entry times, which can be automatically determined by computer vision. For example, FIG. 9, according to one embodiment, depicts an example of synchronized data for one active suturing time with the suture sub-events identified (entry, driving, exit, and pull-out phase).

Another system 200 embodiment is depicted in FIGS. 3-5B and 6, according to one implementation. As with the system 10 discussed above, the system 200 has a table 202, a membrane housing 204 disposed through an opening in the tabletop 206 and having a suturing membrane 208 attached thereto, a surgical depth cylinder 210 disposed around the membrane housing 204, an external camera 212, an internal camera (not shown) and one or more lights (not shown) disposed within the housing 204, a force/torque sensor 214 disposed between the housing 204 and the table frame 216, and a motion sensor 218 attached to the user's hand.

It should be noted that, except as expressly discussed below, the system 200, the various components of the system 200, their features, and their methods of use are substantially similar or identical to the system 10 and its components, features, and methods as discussed above.

Figure 3:
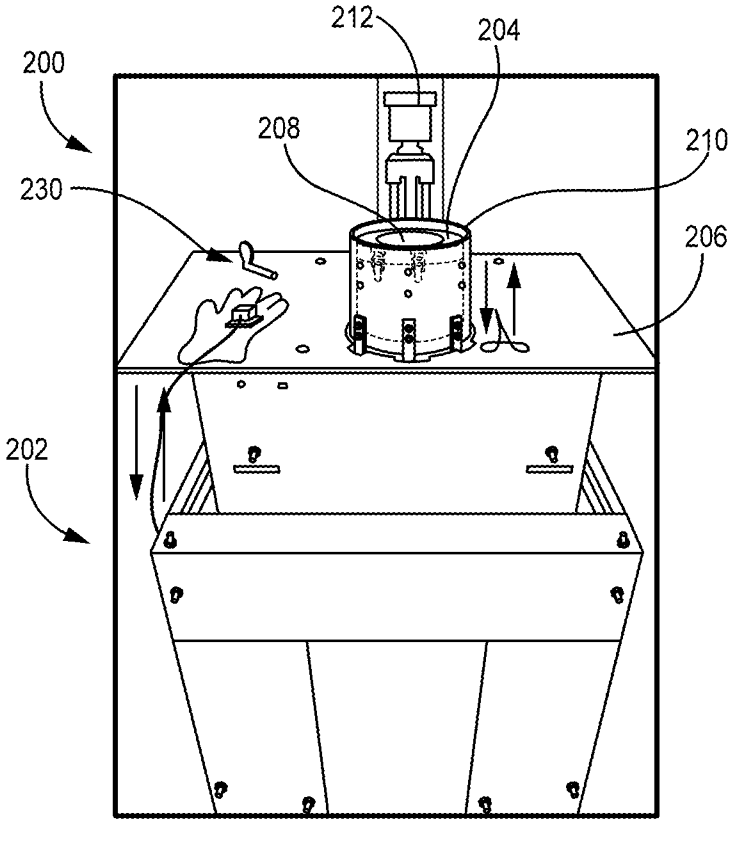
FIG. 3 is a perspective front view of another system for assessing suturing skills, according to another embodiment.

In this system 200 embodiment, the tabletop 206 is moved up and down via an actuation handle 230 that is rotatably disposed on the top of the tabletop 206 as best shown in FIG. 3. The handle 230 can be turned in the desired direction by the user to urge the tabletop 206 up or down to the desired height. Any known mechanism is coupled to the handle 230 and used to drive the tabletop 206 up and down.

The motor 230 is disposed within the table 202 and coupled to the tabletop 206. The motor can be any known motor for such use and can be actuated by the user to urge the tabletop 206 up or down to the desired height.

Figure 4:
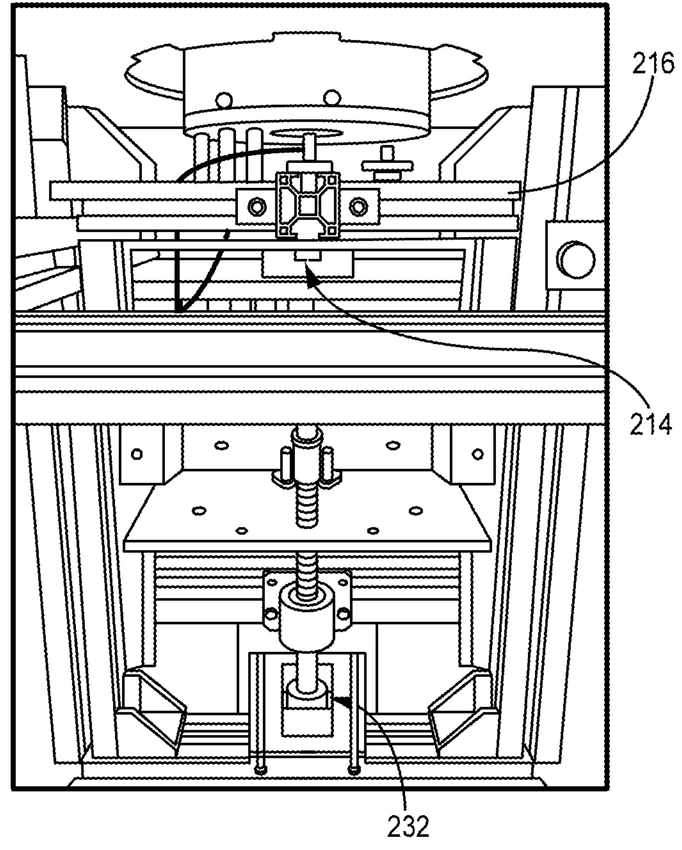
FIG. 4 is a cutaway side view of some of the internal components of the system of FIG. 3, according to one embodiment.
Figure 5A:
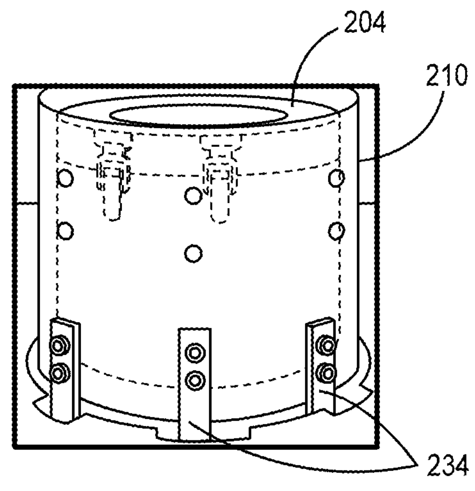
FIG. 5A is a side view of a membrane housing with a moveable depth cylinder disposed around the housing at one height, according to one embodiment
Figure 5B:
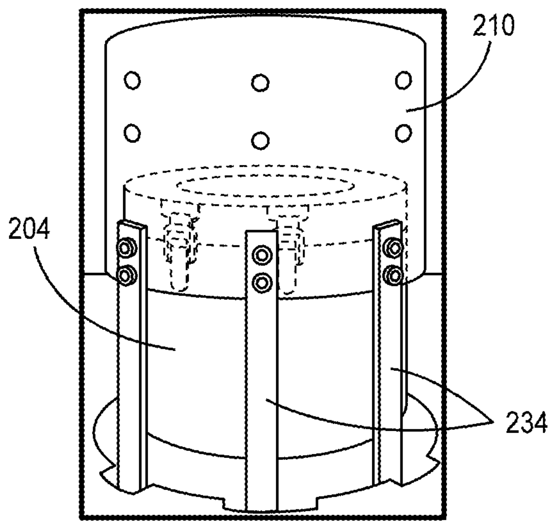
FIG. 5B is a side view of the membrane housing of FIG. 5A with the moveable depth cylinder disposed around the housing at another height, according to one embodiment.
Figures 5C, 6:
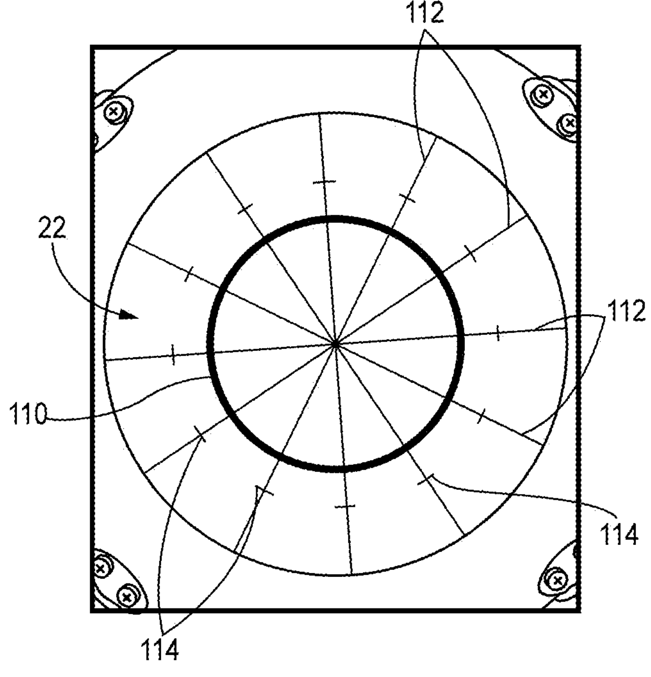
FIG. 5C is a top view of a suturing membrane, according to one embodiment.
FIG. 6 is a perspective view of a user's hand with a motion sensor attached thereto, according to one embodiment.

As best shown in FIGS. 5A and 5B, the surgical depth cylinder 210 is not removable, and instead is adjustable to a variety of heights via a motor 232 disposed within the table 202 (as best shown in FIG. 4). More specifically, the cylinder 210 is attached to the motor 232 via a set of vertical bars 234 that are attached around the periphery of the cylinder 210 near the bottom thereof as best shown in FIGS. 5A and 5B. As such, the motor 232 can be actuated to move the cylinder 210 up or down such that the height of the cylinder 210 can be adjusted as needed. More specifically, in use, if it is desired to have the user simulate suturing at a depth, then the motor 232 can be actuated to move the cylinder 210 upward to a desired height above the membrane 208. Alternatively, if it is desired to have the user simulate surface suturing, then the motor 232 can be actuated to move the cylinder 210 downward to the desired height in relation to the membrane 208. As should be understood from the configuration, a variety of cylinder 210 heights are possible. As such, the system 200 allows for the selection of a specific cylinder 210 height to simulate a specific depth as needed.

As such, the various simulation systems and methods as disclosed or contemplated herein are designed to collect synchronized force, motion, and video data during a suturing exercise, such as, for example, a radial suturing task adapted from the Fundamentals of Vascular Surgery skill assessment. Further, the various system embodiments herein can analyze the synchronized data to extract objective metrics for suturing skill assessment.

EXAMPLE 1

This example focuses on simulator-based assessment of open surgery suturing skill. More specifically, a new surgical simulator is used that is designed to collect synchronized force, motion, video and touch data during a radial suturing task adapted from the Fundamentals of Vascular Surgery (FVS) skill assessment. The synchronized data is analyzed to extract objective metrics for suturing skill assessment.

The simulator has a camera positioned underneath the suturing membrane, enabling visual tracking of the needle during suturing. Needle tracking data enables extraction of meaningful metrics related to both the process and the product of the suturing task. To better simulate surgical conditions, the height of the system and the depth of the membrane are both adjustable. Metrics for assessment of suturing skill based on force/torque, motion, and physical contact are presented. Experimental data are presented from an example comparing attending surgeons and surgery residents.

Analysis shows force metrics (absolute maximum force/torque in z-direction), motion metrics (yaw, pitch, roll), physical contact metric, and image-enabled force metrics (orthogonal and . . . tangential forces) are found to be statistically significant in differentiating suturing skill between attendings and residents.

The results suggest that this simulator and accompanying metrics could serve as a useful tool for assessing and teaching open surgery suturing skill.

Precise quantification of metrics that define "best surgical practices" factors would have potential value to certifying organizations, credentialing committees and surgical educators in addition to providing surgeons in training with objective feedback.

Many metrics for skill assessment have been presented in the literature. These metrics can be classified as force-based metrics, motion-based metrics and image-based metrics. Force-based metrics, such as absolute, mean, and peak forces and force volume, have been most successful at distinguishing novice vs. expert performance at surgical tasks. Hand and/or surgical tool motion obtained via sensor-based kinematic data were also examined to extract motion-based metrics, which can distinguish skill level. Acceleration of the hand and rotation of the wrist were found to distinguish expert surgeons from novices. In addition, hand and/or surgical tool motion obtained from external video using Artificial Intelligence (AI) were also examined to extract motion-based metrics. Total duration, path length, and number of movements were found to be important for distinguishing between attendings and medical students. Further, computer vision has also been used to extract image-based metrics as a means to quantify surgical skill. Frischknecht et al. analyzed photographs taken post-procedure to assess suturing performance. Metrics that proved most meaningful in ranking the quality of suturing included the number of stitches, stitch length, total bite size, and stitch orientation.

Process metrics, i.e., metrics that quantify skill by analyzing how the task was performed, provide significantly more insight for skill training and assessment than product metrics but are also more technically challenging to obtain.

To address the limitations of current surgical simulators, in one embodiment, a suturing simulator has been developed which collects synchronized force, motion, touch, and video data as trainees perform a prespecified suturing task. Product and process metrics are extracted from these data and are used to distinguish suturing skill level. A feature of this system is that standard surgical tools (needle holder, needle with surgical thread, etc.) are used on the platform in contrast to simulators which require the use of modified surgical tools (for example needle coloring, dots for computer vision tracking, etc.). Inspired by suggestions from collaborators in vascular surgery, the system simulates suturing at various depth levels, which represent surgery inside a body cavity or at the surface. Suturing at depth is especially important in vascular surgery and requires significantly different and less intuitive hand motions as compared to suturing at the surface.

The suturing simulator presented here extends a preliminary version of the platform presented in Kavathekar et al. and Singapogu et al. that featured a single external camera, a force sensor, and a motion sensor. This example presents the construction of the simulator, metrics based on force, motion and touch, and a skill assessment of attending and resident surgeons using these metrics. The example was carried out with three main objectives: (1) to validate the simulator's capability of collecting synchronized force, motion, touch, and video data, (2) to extract metrics from data collected from a population with open surgery suturing experience, (3) to test the construct validity of the various metrics. Section 2 describes the simulator, experimental setup, and methods used in the example. Section 3 presents the experimental results, along with a discussion of the force- and motion-based metrics. Section 4 presents conclusions and future work.

The physical system was designed with the following main components: (a) membrane housing, and (b) height adjustable table (see FIG. 3). The cylindrical membrane housing was constructed from clear acrylic and its sides were shielded externally with an aluminum sheet. Eight metal latches along the upper exterior of the membrane housing were used to secure the membrane, a material such as GoreTex®, artificial leather, or other fabric, on which suturing is performed (see FIGS. 5A and 5B).

Similar to the radial suturing task in the Fundamentals of Vascular Surgery, the suture membrane (see FIG. 5C) was designed such that suturing is performed in a radial and uninterrupted fashion. A circle, representing an incision, was drawn on the membrane. The circle was partitioned by radial lines into equal sections each spanning 30°, similar to a clock face. Needle entry points were marked on the radial lines. The distance of the entry mark from the incision line is based on the diameter of the needle. The marks indicated where suturing was to be performed (entry on one side, exit on the other). All membranes were made of artificial leather using a laser cutter.

An internal camera (Firefly MV USB 2.0, Point Grey Research Inc., British Columbia, Canada) was positioned inside the membrane holder and used to record needle and thread movement from underneath the membrane. White LED strips were mounted inside the membrane housing to provide consistent lighting conditions. In addition, an external camera (C920 HD USB 2.0, Logitech International S. A., Lausanne, Switzerland) was positioned above the membrane to record the membrane and hand movement of the subjects during suturing. A 6-axis force/torque sensor (ATI MINI 40, ATI Industrial Automation Inc., NC, USA) was placed under the housing to measure forces and torques applied to the membrane during suturing (see FIG. 4). An InertiaCube4 sensor (InterSense Inc., MA, USA) was used to record hand motion during suturing (see FIG. 6).

To simulate suturing in a body cavity or at the surface of the body, a transparent acrylic cylinder is positioned around the membrane holder. The vertical position of the cylinder can be adjusted to simulate suturing at different depths (see FIGS. 5A and 5B). Capacitive sensing was employed to detect physical contact, i.e., touch, between the subjects' body or the surgical instrument and the cylinder. The interior and top of the cylinder was lined with flexible conductive film (Indium Tin Oxide coated plastic sheet) and aluminum foil, respectively. The conductive materials were attached to a simple capacitive sensing circuit and read using an Arduino.

The membrane housing was mounted onto an adjustable height table. This allows subjects to set the height of the platform as desired for comfort during the suturing exercise. Ergonomic studies of the height of operating tables show that the optimum height of the table lies between 55 cm and 100 cm from the floor up to table surface. The table for the suturing simulator was modified to permit heights between 71 cm and 99 cm.

The system processes of the suturing simulator (see FIG. 3) are categorized into two main stages: (i) Data Collection, and (il) Data Processing (FIG. 7). In the Data-Collection stage, the system synchronizes and logs force, motion, video, and touch data during suturing. The Data-Processing stage uses the collected data to extract metrics of suturing skill.

Data were collected from the four sensing modes: force/torque, motion, video, and physical contact. Force/torque data were collected using the 6-axis force/torque sensor and logged at 1 KHz during suturing. To obtain force/torque data from the sensor, software was written using the NI-DAQ Software Development Kit (SDK). Collected force/torque data were filtered offline with a 10th-order Butterworth lowpass zero-phase filter with a cutoff frequency of 50 Hz to remove noise and smooth the data. To record hand motion, the InertiaCube4 sensor was placed on the dorsum of the subject's dominant hand as shown in FIG. 6 and logged at 200 Hz during suturing. InterSense SDK was used to obtain Øyaw, Opitch, and Oroll measurements of the subject's wrist motion. The internal camera with FlyCapture SDK was used to record needle and suture motion from under the membrane at 60 fps. The external camera was used to record membrane and hand movement at 30 fps. An open source computer vision library (OpenCV 3.0.0) was used to capture and log the external video. For logging touch data, the Arduino capacitive sensing and serial communication libraries were used.

In certain embodiments, the system has an internal camera, enabling extraction of vision-based metrics. Further, according to some implementations, the system synchronizes data collection prior to post-processing on a single PC using a multithreaded implementation and timestamping. The Data Collection Stage software was written in C++ using Microsoft Visual Studio 2013.

During suturing, all unprocessed (raw) data is synchronized and logged. Logging allows for revisiting the raw data at any time for additional investigation and analysis. The raw data were then used in the Data-Processing stage.

In this stage (see FIG. 7), internal video was first processed with a computer vision algorithm to obtain information about needle and thread movement. This information was then used to identify the individual suture cycles. Next, collected raw data were used to extract metrics for each time the subject is actively suturing.

During continuous suturing, a single suture cycle can be divided into two distinct periods of time: active suturing time and idle time. Active suturing time is the time between needle entry into the membrane and complete needle removal from the membrane. Idle time is the time between the end of one active suturing time to the start of the next. In other words, active suturing is the time taken by subjects to complete one suture, whereas idle time is the time spent preparing for the next suture. Active suturing time may be further decomposed into 4 phases: a) entry phase-puncturing the needle into the tissue; b) driving phase-driving the needle along some path under the membrane; c) exit phase-exiting the needle tip from the tissue; and d) pull-out phase-pulling the needle completely from the tissue and then tightening the thread.

Figure 9:
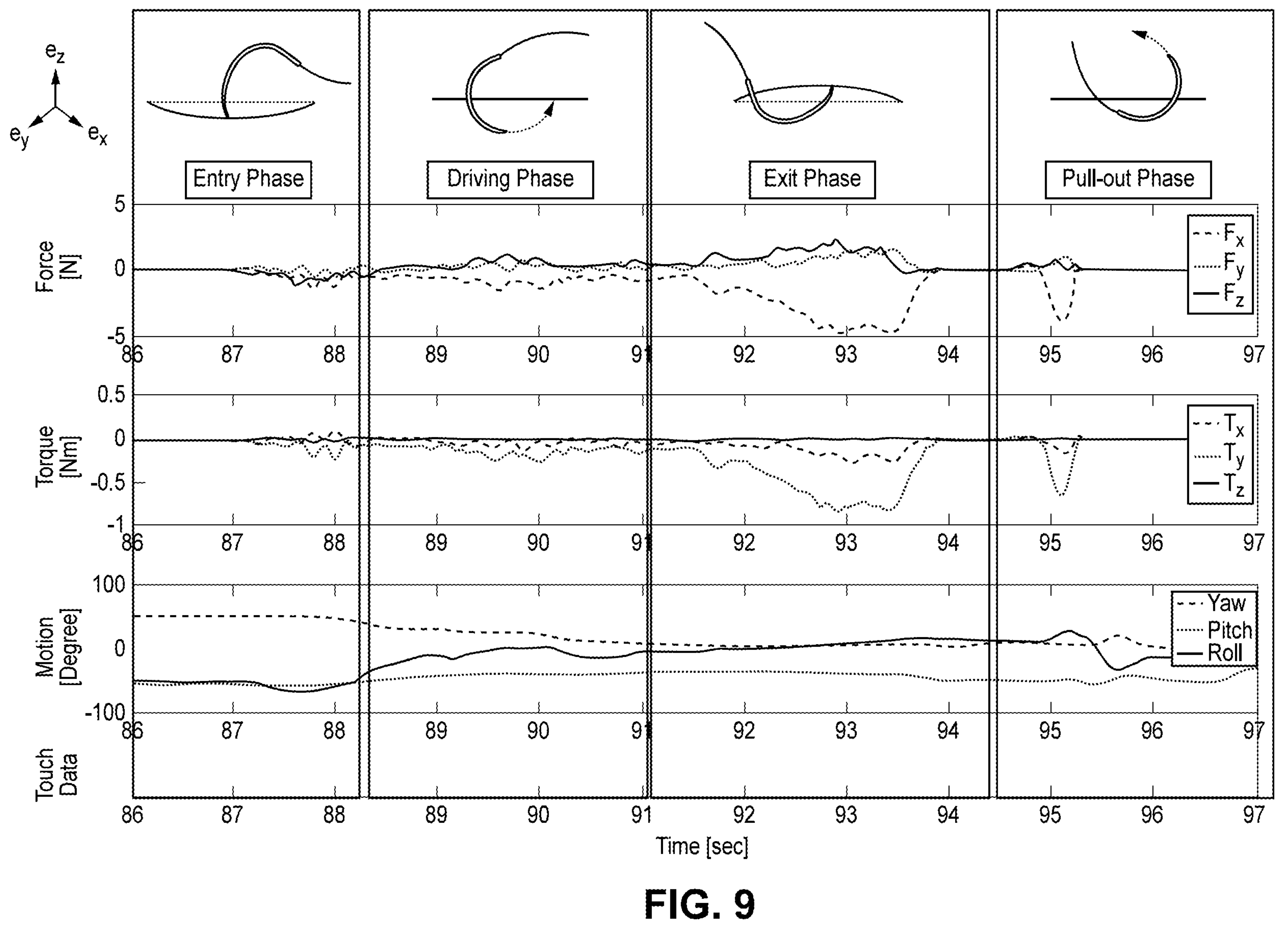
FIG. 9 is an exemplary display of synchronized data gathered by a system for assessing suturing skills, according to one embodiment.
Figures 10A, 10B, 10C, 10D, 10E:
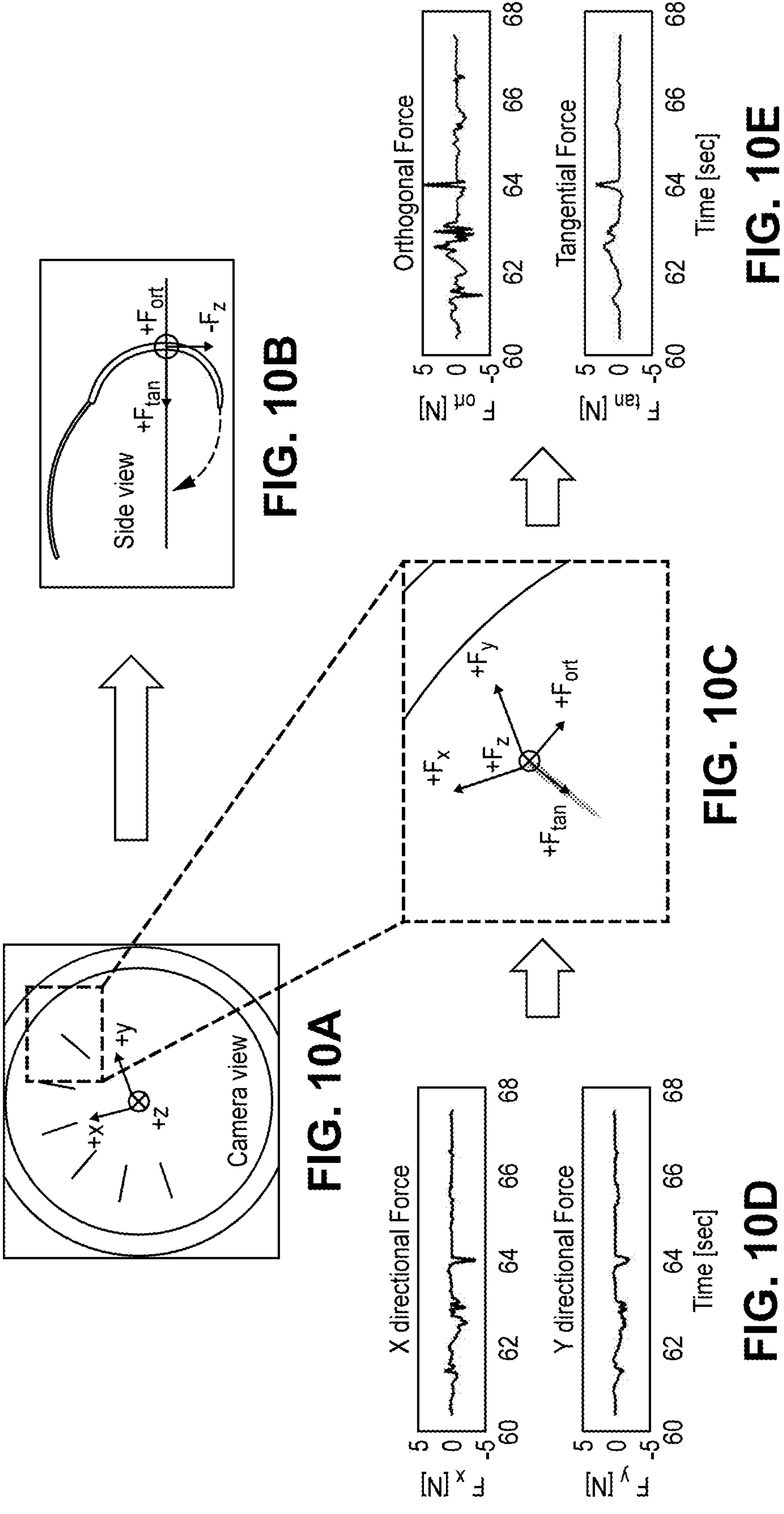
FIG. 10A depicts a representation of the forces of a suture, according to one embodiment.
FIG. 10B depicts a representation of the forces of a suture, according to one embodiment.
FIG. 10C depicts a representation of the forces of a suture, according to one embodiment.
FIG. 10D depicts a graphical representation of the forces of a suture, according to one embodiment.
FIG. 10E depicts a graphical representation of the forces of a suture, according to one embodiment.

Dividing each suture cycle into distinct phases allows for context-specific interpretation of the sensor data. Needle entry and exit times obtained from the computer vision algorithm were used to extract each suture cycle for individual analysis. In addition, a Graphical User Interface (GUI) in MATLAB (FIG. 8) was created to display synchronized force, motion, and touch data, as well as video from external and internal cameras. The interface also labels the needle entry, needle exit and thread entry times automatically determined by computer vision. The interface enables convenient, interactive exploration of the synchronized data. An example of synchronized data for one active suturing time with the suture sub-events identified (entry, driving, exit, and pull-out phase) is shown in FIG. 9.

Many of the metrics presented in this example are computed from time series data of a scalar signal X (f) using one of the following functions:

$$\text{PEAK}_{+}(X) = \max_{t}(X(t)) \tag{1}$$

$$\text{PEAK}_{-}(X) = \max_{t}(-X(t)) = -\min_{t}(X(t)) \tag{2}$$

$$PP(X) = \text{PEAK}_{+}(X) + PEAK_{-}(X) \tag{3}$$

$$INTABS(X) = \int_{t} |X(t)|dt \tag{4}$$

$$DER(X) = \sqrt{\int_{t}\left(\frac{dX(t)}{dt}\right)^{2}dt} \tag{5}$$

The time interval over which the maximum is taken is specified in the definition of the specific metric. Typically the time interval corresponds to one whole active suture time. Note that PEAK+ (X) is the maximum value that signal X took over the time interval and PEAK_(X) is the negative of the minimum value that signal X took during the time interval. If signal X (t) is negative at some point, then PEAK-(X) can be interpreted as the magnitude of peak negative value of X (t). PP (X) is the peak-to-peak amplitude of signal X. INTABS (X) is related to the impulse for a force signal X (t). This quantity will be high when X (t) is high in magnitude over a long period of time. DER (X) is the derivative of the signal X (t) and can be interpreted as the consistency of signal X (t) during the time interval.

For each active suturing time, were used to compute metrics based on time series for force components Fx, Fy, and Fz, and torque components Tx, Tv, and Tz. Based on the coordinate axes (shown in FIGS. 10A-10E), PEAK+ (Fz) is the maximum force component applied upward on the membrane while PEAK-(Fz) is the maximum force component applied downward.

Force applied orthogonal to the stitch direction may increase tissue tearing and should therefore be minimized. The axes of the force sensor are not generally aligned with the directions of the radial stitches, so a change of coordinates is required to determine the force components orthogonal and tangential to the stitch direction. Using the suture entry and exit points detected by computer vision, the suture direction at each suture location can be identified. Then, a change of coordinates can be applied to compute the force tangential to stitch direction and orthogonal to stitch direction (see FIGS. 10A-10E). Calculations of the orthogonal and tangential forces were achieved as follows.

Total force, F→, can be expressed in the vision coordinate system as:

$$\vec{F} = F_x\vec{e}_x + F_y\vec{e}_y \tag{6}$$

where Fx and Fy are the component forces in x and y direction, respectively, as read from the force sensor, and $e_x$ and $e_y$ are the unit vectors in the vision coordinate frame aligned with the x- and y-axes of the force sensor, respectively. Since the coordinate system of the force sensor is constant, $e_x$ and $e_y$ were also constant, independent of suture location. The unit vectors $e_x$ and eywere precomputed based on a calibration experiment.

The same force can also be represented as $$\vec{F} = F_o\vec{e}_o + F_t\vec{e}_t \tag{7}$$

where Fo and Ft are the component forces orthogonal and tangential to the stitch direction in vision coordinate frame, respectively, and e, and $e_t$ are the corresponding unit vectors in the vision coordinate frame.

Thus, (6) and (7) can be rearranged as follows to obtain orthogonal and tangential component forces, Fo and Ft:

$$\begin{bmatrix} F_o \\ F_t \end{bmatrix} = [\vec{e}_o \quad \vec{e}_t]^{-1}[\vec{e}_x \quad \vec{e}_y]\begin{bmatrix} F_x \\ F_y \end{bmatrix} \tag{8}$$

Contrary to $e_x$ and $e_y$, the direction of unit vectors $e_o$ and $e_t$ depend on suture location. The vectors, $e_o$ and $e_t$ are calculated from the suture entry and exit points, whose values are obtained using the computer vision algorithm.

Using the aforementioned calculations, orthogonal and tangential forces for each suture location were obtained. For each active suturing time, (1)-(3) were used to compute metrics based on Fo and Ft.

Metrics on total range of hand motion were extracted from IMU orientation data using (3), specifically PP(θyaw), PP($\theta_{pitch}$) and PP($\theta_{roll}$) for each active suturing time.

The capacitive touch sensor was used to identify and count each instance of physical contact between the subject and the top and/or internal wall of the cylinder around the membrane holder. The total number of touches ($C_n$) made during a suture cycle is used as a metric.

A total of 15 subjects (6 Attending Surgeons, 8 Surgery Residents and 1 Medical Student) were recruited from a local hospital to participate. Informed consent was obtained from participants prior to participation. Each subject was asked to complete a questionnaire on their background and experiences. The data from 12 subjects (5 Attending Surgeons, 7 Surgery Residents) were used in analysis. The range of surgical suturing experience for attending surgeons was from 7 to 25 years, whereas the range of surgical suturing experience for residents was from 2 to 5 years. Three subjects did not meet the criteria and were removed from analysis; 1 attending surgeon (did not meet subject pool definition, not actively practicing), 1 surgery resident (trial interruption), and 1 medical student (did not meet subject pool definition). All attendings in this example specialized in vascular surgery, except one who was a trauma surgery specialist.

Before suturing, subjects were encouraged to adjust the height of the table (FIG. 3) to a comfortable level. The rationale for height adjustment was to allow users to choose a suitable height based on their individual physical characteristics and preferences. Participants were instructed to begin at 10 o'clock on the clock face and suture in a counter-clockwise fashion at each hour to complete a 12 hour cycle. At each hour, the needle is inserted at the marked location and withdrawn to make a stitch symmetric about the incision line. Subjects were instructed to perform continuous, uninterrupted suturing on the membrane using a Prolene suture needle (SH, 26 mm, 3-0) (Ethicon Inc., Somerville, NJ, USA). Subjects performed this procedure at two different membrane depths: at "surface" (i.e., 0 in. depth) and at "depth" (i.e., 4 in. depth) (FIGS. 5A and 5B).

Since the observed distribution of the metrics was not Gaussian (tested with Lilliefors test), the data were analyzed using the Wilcoxon rank sum test (5% significance level) to identify which metrics showed statistically different performance between attending and resident surgeons. Each stitch was considered as a separate trial. Suturing at the surface and at depth are analyzed separately.

TABLE 1

Statistical results for force/torque-based metrics.

| Time series data | Metric | Surface | Depth |
|---|---|---|---|
| $F_x(t)$ | PEAK + ($F_x$) | 0.30 | 0.49 |
| | PEAK − ($F_x$) | 0.18 | 0.75 |
| | PP($F_x$) | 0.65 | 0.99 |
| | INTABS(Fx) | 0.01* | 0.25 |
| | DER($F_x$) | <0.001* | 0.51 |
| $F_y(t)$ | PEAK + ($F_y$) | 0.95 | 0.92 |
| | PEAK − ($F_y$) | 0.14 | 0.24 |
| | PP($F_y$) | 0.34 | 0.77 |
| | INTABS(Fy) | 0.02* | 0.06 |
| | DER($F_y$) | <0.001* | 0.34 |
| $F_z(t)$ | PEAK + ($F_z$) | 0.77 | <0.001* |
| | PEAK − ($F_z$) | <0.001* | 0.01* |
| | PP($F_z$) | 0.01* | <0.001* |
| | INTABS(Fz) | <0.001* | <0.001* |
| | DER($F_z$) | <0.001* | <0.001* |
| $T_x(t)$ | PEAK + ($T_x$) | 0.54 | 0.17 |
| | PEAK − ($T_x$) | 0.87 | 0.99 |
| | PP($T_x$) | 0.39 | 0.43 |
| | INTABS(Tx) | 0.04* | 0.06 |
| | DER($T_x$) | <0.001* | 0.16 |
| $T_y(t)$ | PEAK + ($T_y$) | 0.29 | 0.40 |
| | PEAK − ($T_y$) | 0.25 | 0.61 |
| | PP($T_y$) | 0.12 | 0.84 |
| | INTABS(Ty) | 0.01* | 0.23 |
| | DER($T_y$) | <0.001* | 0.44 |
| $T_z(t)$ | PEAK + ($T_z$) | <0.001* | 0.01* |
| | PEAK − ($T_z$) | <0.001* | <0.001* |
| | PP($T_z$) | <0.001* | <0.001* |
| | INTABS(Tz) | <0.001* | <0.001* |
| | DER($T_z$) | <0.001* | <0.001* |

Metrics with statistical significance are shown with *.

Figure 11:
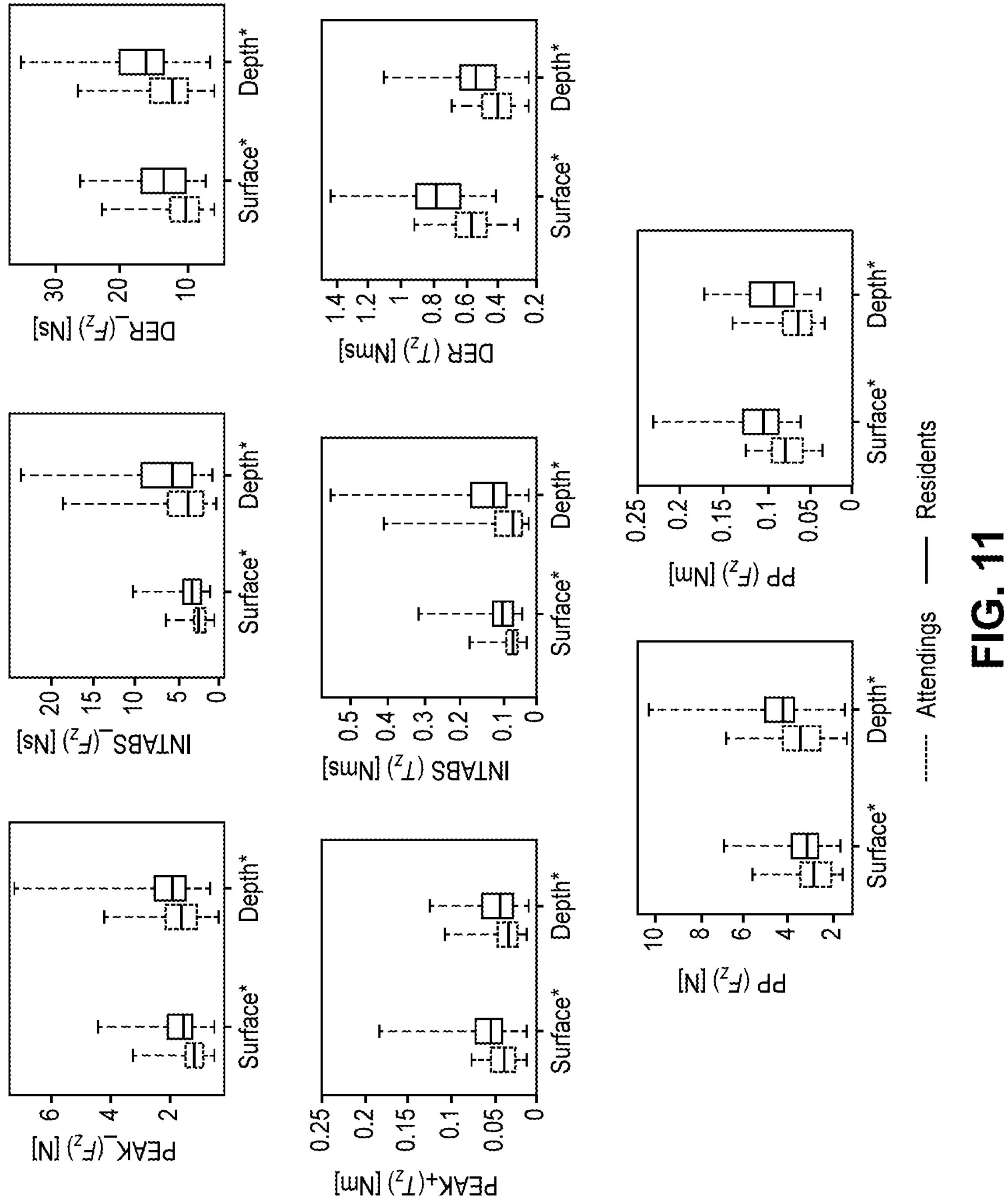
FIG. 11 depicts a graphical representation of experimental results for force/torque-based metrics: according to one embodiment.
Figure 12:
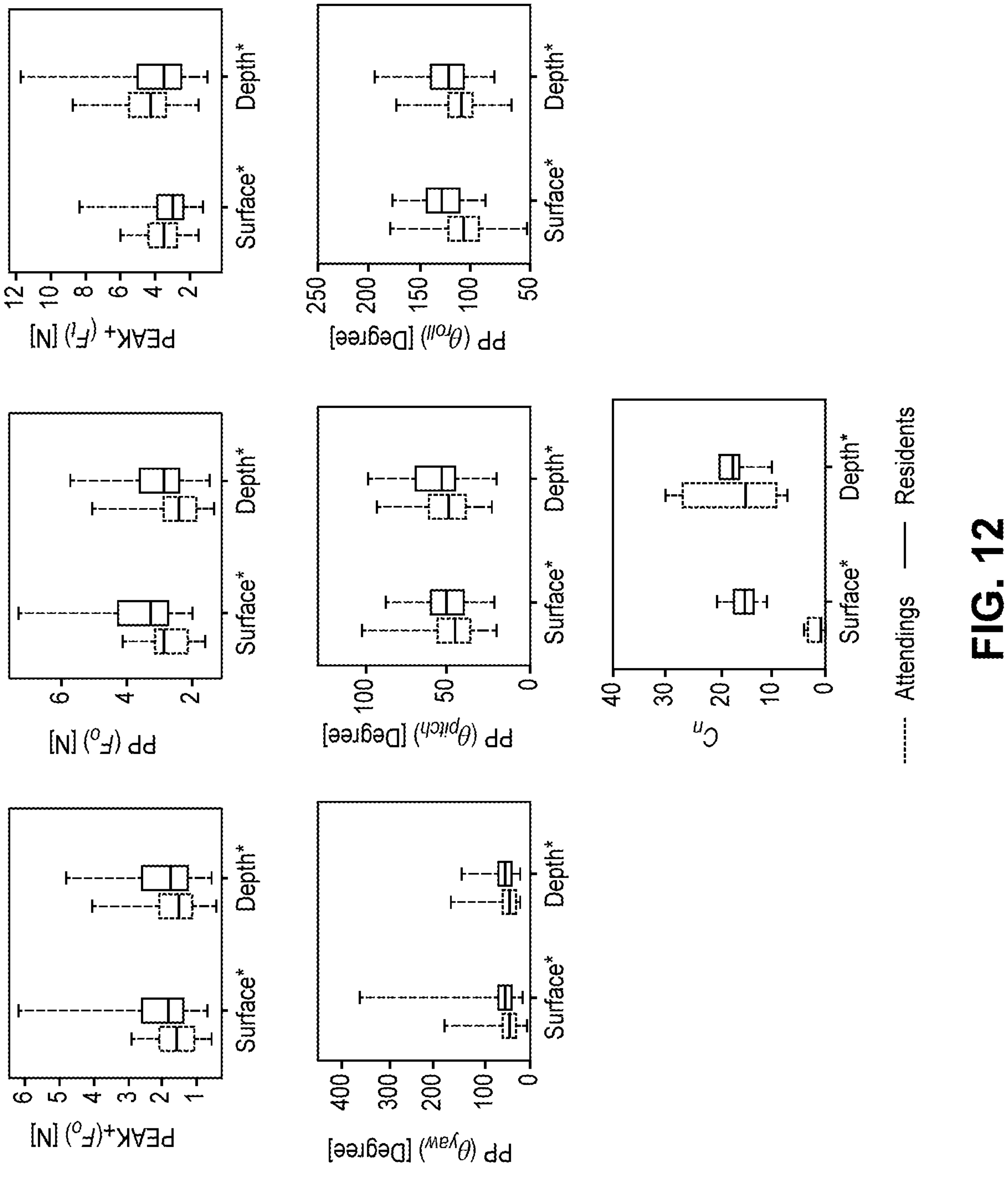
FIG. 12 depicts a graphical representation of motion-based, physical contract, and vision-enabled force metrics, according to one embodiment.

Tables 1, 2 show the p-values for statistical difference between attending and resident surgeons on various force, motion and touch metrics at surface level and at depth level. For selected metrics, FIGS. 11 and 12 provide box plots of performance of attending and resident surgeons at surface level and at depth level. Interpretation and discussion of results are provided below.

TABLE 2

Statistical results for motion-based, physical contact and vision-enabled force metrics.

| Time series data | Metric | p value Surface | Depth |
|---|---|---|---|
| $F_o(t)$ | PEAK + ($F_o$) | <0.001* | 0.02* |
| | PEAK − ($F_o$) | <0.001* | 0.02* |
| | PP($F_o$) | <0.001* | <0.001* |
| $F_t(t)$ | PEAK + ($F_t$) | 0.05* | 0.12 |
| | PEAK − ($F_t$) | 0.02* | 0.07 |
| | PP($F_t$) | 0.16 | 0.22 |
| $\theta_{yaw}(t)$ | PP($\theta_{yaw}$) | <0.001* | <0.001* |
| $\theta_{pitch}(t)$ | PP($\theta_{pitch}$) | 0.67 | 0.02* |
| $\theta_{roll}(t)$ | PP($\theta_{roll}$) | <0.001* | <0.001* |
| C(t) | $C_n$ | <0.001* | 0.76 |

Metrics with statistical significance are shown with *.

Results for force-based metrics show that INTABS (Fx), DER (Fx), INTABS (Fy) and DER (Fy) were significantly different between attendings and residents at surface level. In addition, a statistical difference in performance between attending and resident surgeons was found for metrics PEAK-(Fz), PP (Fz), INTABS (Fz) and DER (Fz) at both depth and surface as well as for metric PEAK+ (Fz) at depth. For z-directional force metrics, the medians of attendings at both surface and depth level were found to be lower as compared to residents. The results show that z-directional force was found to be important for distinguishing between experience levels. In contrast to z-directional forces, in this example, metrics calculated for x and y direction forces at both surface and depth level were found to be non-significant.

Similarly, results for torque-based metrics show that INTABS (Tx), DER (Tx), INTABS (Ty) and DER (Ty) were significantly different between attendings and residents at surface level. In particular, results for torque-based metrics show that z directional torques (PEAK+ (Tz), PEAK-(Tz), PP (Tz), INTABS (Tz) and DER (Tz)) were significantly different between attendings and residents, at both the depth and surface level. The z-axis is vertical, so Tz is associated with forces orthogonal to the z-axis applied with a non-zero moment arm. Given the radial suturing pattern, that means Tz is most closely associated with forces orthogonal to the stitch direction. This motivates direct measurement of the orthogonal force Fo, as explained in 2.1.4.2.

Results show that the metrics obtained from orthogonal force (Fo) were statistically different between attendings and residents on both surface and depth levels (see Table 2). In addition, tangential force (Ft) metrics were significantly different between attendings and residents at surface, with the exceptions of PP (Ft). Orthogonal forces applied by attendings were lower than those applied by residents, whereas tangential forces applied by attendings were higher.

In Horeman et al., subjects made parallel sutures aligned with the y axis of the force sensor. It was observed that the maximum absolute forces in x and y directions were important for distinguishing between experience levels. Since the stitch direction was unchanged, x and y force directions were always orthogonal and tangential to the stitch direction, respectively. The example presented here uses a radial suture membrane with stitches in 12 different directions (see FIG. 5C). This radial membrane is based on the one used in FVS training and is intended to test the subject's dexterity and preparedness for vascular anastomosis. Since the force sensor was fixed in place, x and y force directions were not generally aligned with stitch direction. Even though x and y directional force metrics were not found to be statistically significant in this example, measurements of forces in x and y directions are required to calculate orthogonal and tangential forces. Reinterpreting the x and y for axes from Horeman et al. as orthogonal and tangential to stitch direction, the present example supports that orthogonal forces, and to a lesser extent tangential forces, are important for distinguishing skilled performance.

Previous studies suggest that there is a significant difference in hand movement between expert and novice surgeons during suturing. The rotation of the wrist, indicated by $\theta_{roll}$, was previously found to be particularly useful in assessment of suturing skill. In the present example, similar to earlier studies, the total range of hand movement for $PP(\theta_{yaw})$ and $PP(\theta_{roll})$ at both surface and depth, and for $PP(\theta_{pitch})$ at depth were found to be statistically significant in differentiating attendings from residents. This suggests that yaw, pitch and roll might be useful for assessment of suturing skill.

Results for yaw, pitch, and roll show that total range of hand movement by attendings are consistently lower than that of residents, regardless of depth. In Dubrowski et al. and Horeman et al., it was found that experts use greater wrist rotation during suturing. In contrast, the results show that attendings use less wrist rotation. This may be explained by the fact that the majority of attendings in this example were experts in the field of vascular surgery. Due to the intricate nature of this type of surgery, it may be reasonable to assume that significant wrist rotation is not necessary in achieving accurate suturing during the surgical procedure. Also, pitch was found to be statistically significant, but only at depth, possibly because hand motion is more complicated when a subject sutures at depth. Moreover, during the experiments, it was observed that inexperienced participants tend to reposition the needle holder more often while suturing at depth. The complexity of hand movement during suturing deserves further investigation, specifically for suturing at depth, an essential aspect of vascular suturing.

The number of times subjects made physical contact with the platform at both surface and depth conditions was examined. Results indicate that the total number of physical touches ($C_n$) on surface level for attendings was significantly lower than for residents, whereas there was no statistical difference between attendings and residents at depth. It should be noted that suturing at depth was introduced to mimic more realistic surgical conditions; however, feedback from attendings after the experiment revealed that requiring a surgeon to suture accurately without touching the top and/or the walls of the cylinder was an overly restrictive constraint. In fact, in certain conditions during surgery, surgeons strategically use boundaries of body cavities, for instance, to augment their forces during suturing.

In certain embodiments, a suturing simulator is provided with the capability of collecting synchronized force, motion, touch, and video data to allow for the assessment of suturing skill in open surgery. Data collected from the simulator during suturing allowed for the extraction of metrics for quantifying suturing skill between different levels of trainees. Force-based, torque-based, motion-based, and physical contact metrics were presented. Combining force data with computer vision information, vision-enabled force metrics were found, specifically for forces orthogonal and tangential to stitch direction which provide deeper insight into suturing performance. Also, the vision algorithm aided in the identification of suture events and the segmentation of corresponding sensor data.

Experimental data collected from both attendings and residents were presented. Presented metrics were used to compare attendings' and residents' performance. Analysis shows that force metrics (force and torque in z direction), motion metrics (yaw, pitch, roll), physical contact metric, and image-enabled metrics (orthogonal and tangential forces) were statistically significant in differentiating suturing skill between attendings and residents. These results demonstrate the feasibility of distinguishing fine skill differences between attendings and residents, as compared to experienced vs. completely inexperienced personnel.

EXAMPLE 2

Background: To maximize patient safety, surgical skills education is increasingly adopting simulation-based curricula for formative skills assessment and training. However, many of the standardized assessment tools rely on human raters for performance assessment, which is resource-intensive and subjective. Simulators that provide automated and objective metrics from sensor data can address this limitation. An instrumented bench suturing simulator was used, patterned after the Clock Face (CF) radial suturing model from the Fundamentals of Vascular Surgery (FVS), for automated and objective assessment of open suturing skills.

Methods: For this example, 97 participants (35 attending surgeons, 32 residents, 30 novices) were recruited at national vascular conferences. Automated hand motion metrics, especially focusing on rotational motion analysis, were developed from the Inertial Measurement Unit (IMU) attached to participants' hands, and the proposed suite of metrics was used to differentiate between skill levels of the three groups.

Results: Attendings' and residents' performances were found to be significantly different than novices for all metrics. Moreover, most of the novel metrics could successfully distinguish between finer skill differences between attending and resident groups. In contrast, traditional operative skill metrics such as Time and Path Length were unable to distinguish attendings from residents.

Conclusion: This example provides evidence for the effectiveness of rotational motion analysis for the assessment of suturing skill. The suite of IMU-based hand motion metrics introduced in this example allow for the incorporation of hand movement data for suturing skill assessment.

Objectively assessing and measuring the technical competency of surgical trainees in safe, simulated settings is invaluable in surgical education. The surgical education community continuously searches for highly reliable, safer, efficient, and more granular methods to objectively evaluate the practical skills of their trainees, hoping to foster competent surgeons 1.

As the paradigm in board certification is shifting toward standardized hands-on competency examination, a simulation-based curriculum and assessment tool called the Fundamentals of Vascular Surgery (FVS) was designed for targeted teaching and testing of basic open vascular skills 2. FVS was developed to address concerns related to reduced resident work hours 3 and decreased exposure of trainees to open surgical procedures because of the shifting practice patterns toward a majority endovascular approach 4. Results of the first study to evaluate open vascular skills based on FVS demonstrated a high correlation between ratings with training levels of the 20 surgical trainees who participated in this study (r=0.93, combined score) when assessed by two experienced evaluators on a global rating scale (GRS) 2. More recently, Schmiederer et al. (2021) provided further evidence supporting the effectiveness of FVS by conducting a three-year study involving 17 general surgery residents who were assessed on the FVS models by an expert rater 5. Owing to the already established body of research demonstrating the value of simulation-based training curricula 6-8 and the several recent studies showcasing the promise of the FVS curriculum 4,5,9, the FVS is slated to be soon required by the ABS. However, one limitation of bench simulation models is the need for expert assessors for manual skills assessment. Performance on the FVS simulation kit is evaluated by experienced raters using a GRS, adapted from Objective Structured Assessment of Technical Skill (OSATS) 2. This work addresses this limitation through an instrumented simulator that provides automated and objective skill assessment via sensor measurements for the FVS Clock Face (CF) suturing task 5.

Automated sensor-based metrics offer viable solutions for the emergent need for objective simulation-based assessment tools tailored for credentialing. To this end, this example introduces an instrumented benchtop simulator system for open vascular suturing patterned after the FVS CF suturing model. It should be noted that one version of this simulator has been named "SutureCoach™, which may be referenced elsewhere in this example and other examples herein. Radial suturing on The simulator system requires sensorimotor coordination, dexterity, controlled hand-roll, and needle holder maneuvering skills. Realization of a sensorized benchtop suturing simulator offers a practical solution for objective and automated assessment of open suturing skills, alleviates the burden of proctor training, and ensures consistent grading.

The current open suturing skill assessment research, specifically studies utilizing sensor-based metrics, has three major limitations. First, metrics are scarce and mostly focus on the general economy of motion, providing limited insight into task-specific qualities of motion. Second, the sample size is often too small for the inferences to be generalizable. Third, many studies include only a limited range of clinical expertise (e.g., several residents vs. several attendings) for examining the efficacy of metrics in distinguishing skill. Here, these limitations were attempted to be overcome by extensively analyzing the quality and economy of hand motions during open radial suturing by collecting an extensive national dataset and assessing skill on a finer level. This example aimed to explore the effectiveness of a suite of performance metrics extracted from an Inertial Measurement Unit (IMU) for open vascular suturing skill assessment. While human movement is normally comprised of both translation and rotation, the vascular suturing task performed on the simulator system is predominantly rotational in nature. As such, it was surmised that quantitative rotational analysis could also be valuable for evaluating suturing skills and gaining more insight into the process of suturing. The lack of rotation-based hand motion metrics for suturing skill assessment motivated the measurement technique used herein. Therefore, it was hypothesized that (1) hand motion metrics can accurately distinguish between suturing skill levels of novices, residents, and attending surgeons and that (2) rotational motion analysis, i.e., metrics based on hand rotation, are more insightful for evaluating CF suturing skill than metrics based on translational motion.

The suturing simulator as shown in FIG. 1A, was designed and developed based on prior research on earlier iterations. The simulator was instrumented with four sensing modalities to capture aspects of skill vascular surgeon-educators deem necessary for open suturing. First, the simulator system featured two Intel® RealSense™ Depth Cameras (D435). Second, an ATI MINI 40 force sensor (ATI Industrial Automation Inc., NC, USA) was used to read forces applied to the membrane. Third, two EM position sensors (Ascension trakSTAR™ Model 180, Northern Digital Inc.) were attached to the needle holder (titanium 8-in. Mayo-Hegar). Fourth, two IMUs were secured to the subjects' dominant hand and wrist. The suturing platform was comprised of a hollow cylinder housing a synthetic leather membrane integrated into a custom-made adjustable height table.

For this example, an extensive national dataset consisting of 392 suturing trials was collected from subjects with diverse training backgrounds and clinical standings. All subjects (n=97) were recruited at various national vascular conferences over a 5-month period. Voluntary informed consent was obtained from every participant. Clemson University Institutional Review Board provided ethics approval for this example.

The radial suturing task of this example consisted of two different conditions: suturing at surface and depth (simulating suturing in an anatomical cavity), as shown in FIGS. 2A and 2B. All recruited subjects went through standardized instructions about the task, the data obtained, and the sensor-based metrics computed. The suturing task was comprised of four trials: first at the surface, then at depth, and then two more trials with the same sequence. A trial consisted of 12 interrupted sutures around the CF engraved on the membrane affixed on the simulator. The laser-engraved synthetic membrane was replaced with a new one before each trial. All subjects used 3-0 Prolene sutures (26 mm 1/2c SH needle) throughout this example and received new sutures upon request during the task.

Due to the voluntary participation and the nature of research involving human subjects, not all subjects completed all four trials or performed all 12 sutures around the CF. However, these incomplete suturing trials only amounted to a minor portion (0.014%) of the dataset (65 missing sutures). In addition, two trials were excluded due to technical errors (e.g., IMU hitting the table mid-trial), resulting in 392 trials and 4687 sutures total.

For analysis, participants were categorized into three groups: (1) attending surgeons and fellows (na=35), (2) residents PGY1-PGY5 (nr=32), and (3) novices (nn=30) consisting of medical students and graduate students. The three groups included 142, 126, and 124 trials, respectively. Table 3 shows the detailed distribution of subjects' demographic. All attending surgeons specialized in vascular surgery. All fellows specialized in vascular surgery except one participant, who was a colorectal surgery fellow. The majority (78%, n=25) of the resident group were vascular surgery residents, while the remaining others (n=7) were residents specializing in general, colorectal, and orthopedics.

TABLE 3

The demographic information of all study participants

| Demographic Information | Number | Surface trials | Depth trials | Surface sutures | Depth sutures | Total no. of sutures |
|---|---|---|---|---|---|---|
| Participants | 97 | 196 | 196 | 2,345 | 2,342 | 4,687 |
| Male | 68 (70%) | 138 | 138 | 1,650 | 1,650 | 3,300 |
| Female | 29 (30%) | 58 | 58 | 695 | 692 | 1,387 |
| Novices | 30 (31%) | 62 | 62 | 737 | 740 | 1,477 |
| Graduate student | 13 | 28 | 28 | 335 | 335 | 670 |
| Medical student | 17 | 34 | 34 | 402 | 405 | 807 |
| Residents | 32 (33%) | 63 | 63 | 756 | 755 | 1,511 |
| PGY1 | 3 | 6 | 6 | 72 | 71 | 143 |
| PGY2 | 5 | 10 | 10 | 120 | 120 | 240 |
| PCY3 | 5 | 10 | 10 | 120 | 120 | 240 |
| PGY4 | 8 | 15 | 15 | 180 | 180 | 360 |
| PGY5 | 11 | 22 | 22 | 264 | 264 | 528 |
| Attendings | 35 (36%) | 71 | 71 | 852 | 847 | 1,699 |
| Fellow | 10 | 19 | 19 | 228 | 226 | 454 |
| Attending (≤10 y) | 13 | 26 | 26 | 312 | 310 | 622 |
| Attending (>10 y) | 12 | 26 | 26 | 312 | 311 | 623 |

To portray the attending surgeons' population with better detail, they are grouped based on years of experience as attending surgeons.
PGY, postgraduate year.

This example focused on quantifying hand motions; hence only the data obtained from the hand IMU were used to formulate metrics for this example. The IMU was the Xsens MTw Awinda wireless motion tracker (Xsens Technologies BV, Enschede, The Netherlands), which sampled hand motions internally at 1 KHz and wirelessly transferred filtered and calibrated inertial data to the backend software at 120 Hz. The IMU housing dimensions were 47×30×13 mm, weighing 16 g [18-20]. All participants wore Latex surgical gloves, and the IMU was secured to the dorsum of their dominant hand using Velcro straps. For standardized placement, operators centered the IMU approximately on the midshaft point of the third metacarpal through visual estimation [21]. The IMU directly outputted angular velocity [rad/s], i.e., rotational velocity around hand roll/pitch/yaw axes as well as the three-dimensional linear acceleration [m/s$^2$] of the hand in x, y, and z in Cartesian sensor-frame coordinates. Custom backend C++ software automatically synchronized all sensors at the beginning of each trial. Data were recorded until an operator manually stopped data collection after subjects finished the 12$^{th}$ suture around the CF. The camera affixed to the simulator bed enabled real-time detection of needle entry/exit times [16,17]. Prior to motion analysis, entry/exit times were used to segment the IMU data for each suture cycle. Lastly, each suture's angular velocity and linear acceleration time series were used to compute the hand motion metrics that are proposed, calculated, and used throughout the rest of this example.

Figure 13:
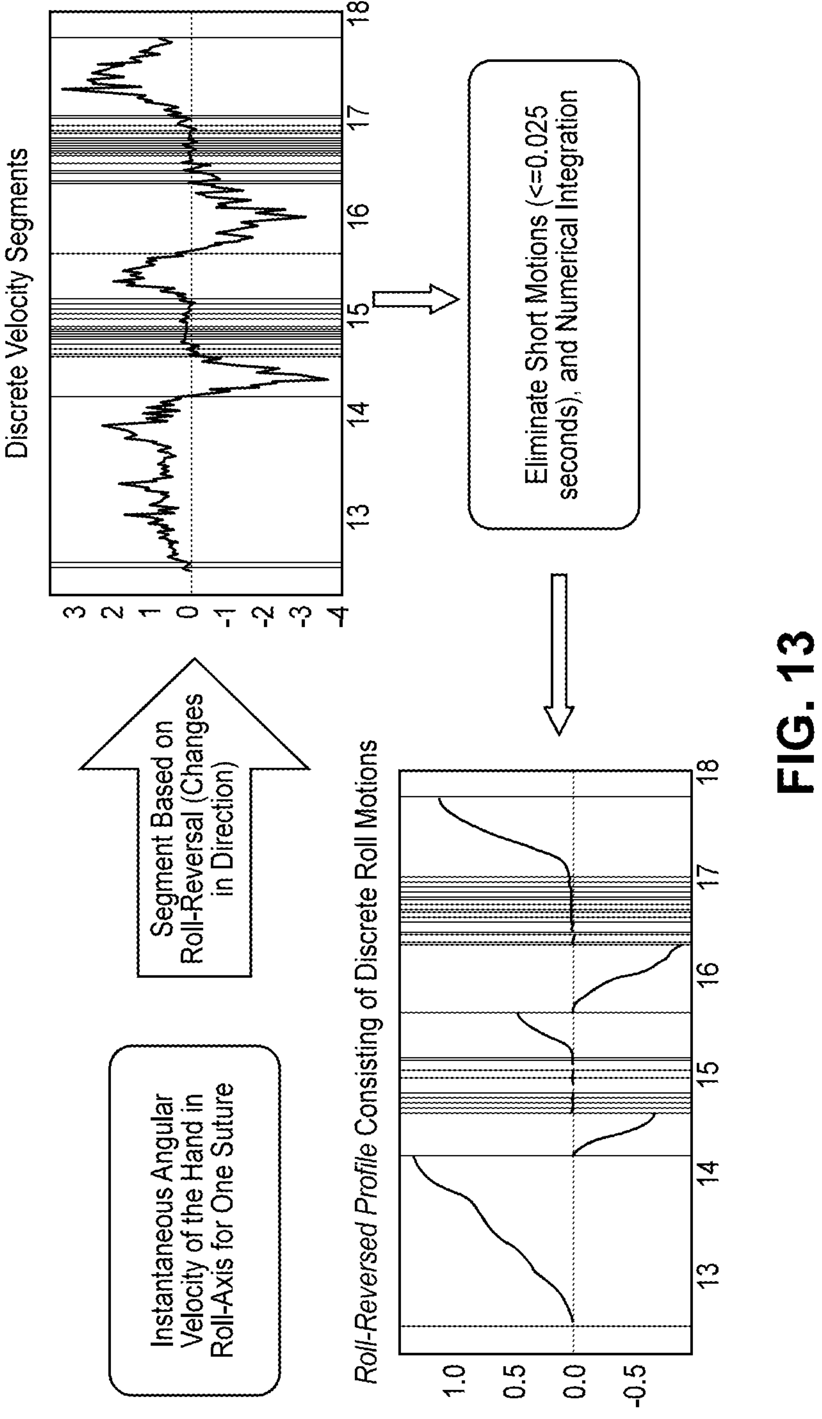
FIG. 13 is a flow chart illustrating the process of calculating discrete roll motions for each suture action, according to one embodiment.

Metrics were formulated based on clinical suitability to evaluate different components of open suturing skill deemed essential for achieving competency. Formulas and descriptions of all metrics are provided in Table 4.1. Table 4.2 reproduces the 'Formulation' column of Table 4.1. Moreover, Table 5 provides easy-to-understand clinical interpretations of metrics and examples of how they could potentially relate to clinicians' feedback to trainees. For each suture, a roll-reversal profile was constructed based on changes in the direction of hand roll (forehand/backhand). After segmenting the instantaneous angular velocity time series of hand roll based on reversal points, motions with three or fewer samples (<=0.025 seconds) were filtered to reduce sensitivity to unintentional motions, especially during periods of hesitation. Then discrete roll motions were calculated by numerical integration of each velocity segment. The flowchart provided in FIG. 13 illustrates this process.

TABLE 4.1

Summary of hand motion metrics used in this study.

| Category | Metric | Formulation | Description |
|---|---|---|---|
| RRP | No. of Rolls | N = number of discretized segments in RRP | Measures the no. of roll motions in RRP. |
| | Effective roll | $\lvert\Sigma R_\theta\rvert$ | Forward roll in the needle driving direction calculated by summating all roll angles in the RRP and normalized based on needle configuration during suturing (forehand or backhand). |
| Roll angular velocity profile | Average roll angle | $\frac{\lvert\sum R_\theta\rvert}{N}$ | The average angle of all discrete roll motions in the RRP. |
| | Maximum roll velocity | max(\|Vprofile\|) | Peak angular velocity attained while rolling. |
| | Median roll velocity | median(\|Vprofile\|) | Median angular velocity of the hand in the roll direction. |
| | $SPARC_r$ | $SPARC_r = -\int_0^{\omega_c}\left[\left(\frac{1}{\omega_c}\right)^2+\left(\frac{d\hat{V}(\omega)}{d_\omega}\right)^2\right]d\omega$ | The arc length of the Fourier transform of the velocity profile.[22,23] |

TABLE 4.1-continued

Summary of hand motion metrics used in this study.

| Category | Metric | Formulation | Description |
|---|---|---|---|
| | | $\hat{V}(\omega) = \frac{V(\omega)}{V(0)}$ | |
| | $LDLJ_r$ | $-\text{Ln}\left(\frac{dur^3}{V_p^2}\int(V'')^2 dt\right)$ | The natural log of jerk integrated and squared. Jerk was derived from angular velocity using the Savitzky-Golay method.[22,23] |
| | $LDLJ_t$ | $-\text{Ln}\left(\frac{dur}{a_p^2}\int(a')^2 dt\right)$ | The natural log of jerk integrated and squared. Jerk was derived from linear accelration using the Savitzky-Golay method.[22,23] |
| 3D linear acceleration | Path length (pl) | $PL = \int \frac{t_{needle\,exit}}{t_{needle\,entry}} \int acc(x, y, z)dt$ | The total point-to-point 3D distance traveled by the hand to complete the suture, calculated after the position of each point in Cartesian coordinates was estimated based on acceleration data. |
| Computer vision segmentation | Time | $T = t_{needle\ exit} - t_{needle\ entry}$ | Duration of the suture cycle. |

3D, 3-dimensional: LDLJ, log dimensionless jerk: PL, path length: RRP, roll-reversal profile: SPARC, spectral are length.

TABLE 4.2

| Formulation |
|---|
| N = number of discretized segments in RRP |
| $\lvert\Sigma R_\theta\rvert$ |
| $\frac{\lvert\sum R_\theta\rvert}{N}$ |
| max(\|Vprofile\|) |
| median(\|Vprofile\|) |
| $SPARC_r = -\int_0^{\omega_c}\left[\left(\frac{1}{\omega_c}\right)^2 + \left(\frac{d\hat{V}(\omega)}{d_\omega}\right)^2\right]d\omega$ |
| $\hat{V}(\omega) = \frac{V(\omega)}{V(0)}$ |

TABLE 4.2-continued

| Formulation |
|---|
| $-\text{Ln}\left(\frac{dur^3}{V_p^2}\int(V'')^2 dt\right)$ |
| $-\text{Ln}\left(\frac{dur^3}{a_p^2}\int(a')^2 dt\right)$ |
| $PL = \int \frac{t_{needle\,exit}}{t_{needle\,entry}} \int acc(x, y, z)dt$ |
| $T = t_{needle\ exit} - t_{needle\ entry}$ |

TABLE 5

| Category | Metric | Clinical Motivation | Examples of Possible Interpretations |
|---|---|---|---|
| Efficiency | Number of Rolls | Following the curvature of the needle efficiently with fewer adjustments; decisiveness in driving the needle | Made many unnecessary moves; inefficient; too many adjustments while maneuvering the needle<br>Few number of rotations and maximum efficiency |
| | Effective Roll | Effective magnitude of rotation in the suturing direction; rotational economy | Unnecessary and excessive amount of rotation due to errors in angular path planning<br>Completed the suture with efficient hand roll and minimal wasted rotational motion |
| | Average Roll Angle | Average amount of rotation; rotational dexterity | Made too many small and tentative rotations; failure to follow the curvature of the needle<br>Completed the suture using substantial and deliberate rotations |
| | Path Length (PL) | Economy of translational hand movements | Superfluous hand path; wasted hand movements<br>Optimal hand path; efficient hand movements |
| | Time | Time taken to complete the suture | Excessive time spent on the suture<br>Suture was completed quickly |
| Speed | Maximum/Median Roll Velocity | Speed of hand rotation in the roll direction | Slow and hesitant rotations<br>Fast and confident rotations |

TABLE 5-continued

| Category | Metric | Clinical Motivation | Examples of Possible Interpretations |
|---|---|---|---|
| Smoothness | SPARC & LDLJ | Smoothness of hand motions | Excessive hand tremor; unsmooth and uncontrolled hand movements/rotations Steady, controlled, and smooth movements/rotations with minimal jerk |

Number of Rolls metric measures the economy of hand roll and subsequently measures decisiveness by considering both intentional and unintentional motions [19,22-25]. Competent surgeons are expected to follow the curvature of the needle and complete sutures more economically, leading to fewer roll motions.

Effective Roll metric calculates the total angular distance rolled during a suture while considering the direction of roll. Backward rolls are considered inadequacies that increase the chance of tissue trauma; hence, in this metric, they are subtracted from the total cumulative sum. Skilled subjects are expected to follow an efficient pre-planned angular path and have lower Effective Roll scores.

Average Roll Angle was formulated to compute the average magnitude of all roll motions in the roll-reversal profile for each suture cycle. Suturing with a semi-circular needle requires more rotational motions as opposed to translational motions: Hence, superiorly skilled subjects are expected to have better rotational dexterity and drive the needle more in each rotation.

To explore whether skillful surgeons attain high angular velocities while suturing or use slower controlled roll motions, the hand roll angular velocity time series were used to formulate two velocity metrics: Maximum and Median Roll Velocity during a suture cycle.

Spectral arc length (SPARC) and log dimensionless jerk (LDLJ) are two smoothness metrics suitable for the assessment of motor and psychomotor performance. Both metrics were calculated based on angular velocity to quantify hand roll smoothness; hence they are denoted as SPARCr and LDLJr. LDLJ was also applied to linear acceleration to estimate the smoothness of translational hand movements (denoted here as LDLJi). The neuromuscular structure is expected to develop through training and fostering of suturing skills, resulting in improved motor coordination. Thus, jerkier and less controlled motions are expected from novices/residents compared to attending surgeons[26-28].

The hand Path Length during the completion of a surgical task is a valuable metric for assessing technical skills [4,12,29]. Point-to-point Path Length was calculated using 3D accelerometer data (Table 4.1, Table 4.2).

Finally, Time, the duration of a suture, was also used as a general task economy metric. Statistical analyses of this example utilized R version 4.2.2. One-way Analysis of Variance (ANOVA) was used to determine if the three sample populations, i.e., attendings/residents/novices, have the same mean scores for IMU-based metrics in both conditions of the task: superficial and deep suturing. ANOVA results showed that for all metrics at both conditions, at least one sample group was significantly different than the other two. Results of pairwise comparisons of suturing skills between the three populations are visualized in FIG. 14. Also, FIG. 15 contains the boxplots of metric scores for the three sample populations to give an overview of all metric distributions. The distributions of attending, resident, and novice groups are also expressed in terms of mean, standard deviation, median, and interquartile ranges in Tables 6 and 6. Lastly, Tables 8 and 9 show the exact P values and confidence interval boundaries.

TABLE 6

| | Attendings | | | | | Residents | | | | | Novices | | | | |
|---|---|---|---|---|---|---|---|---|---|---|---|---|---|---|---|
| | Avg | Std | Med | Q1 | Q3 | Avg | Std | Med | Q1 | Q3 | Avg | Std | Med | Q1 | Q3 |
| Num Rolls | 47.57 | 29.30 | 41.00 | 29.00 | 58.25 | 58.87 | 34.38 | 53.00 | 36.00 | 75.00 | 86.70 | 84.23 | 70.00 | 46.00 | 104.00 |
| Avg Roll | 0.16 | 0.09 | 0.14 | 0.10 | 0.29 | 0.15 | 0.09 | 0.13 | 0.09 | 0.18 | 0.11 | 0.07 | 0.10 | 0.07 | 0.14 |
| Effective Roll | 1.05 | 0.72 | 0.96 | 0.48 | 1.49 | 1.15 | 0.72 | 1.04 | 0.59 | 1.61 | 1.42 | 0.84 | 1.32 | 0.80 | 1.89 |
| Max Roll Vel | 7.01 | 2.94 | 6.28 | 5.03 | 8.35 | 7.51 | 2.82 | 7.03 | 5.58 | 8.88 | 6.26 | 2.93 | 5.67 | 4.04 | 8.01 |
| Med Roll Vel | 0.55 | 0.23 | 0.51 | 0.39 | 0.67 | 0.63 | 0.24 | 0.60 | 0.45 | 0.79 | 0.49 | 0.22 | 0.46 | 0.34 | 0.62 |
| SPARC | −12.53 | 5.96 | −11.23 | −14.86 | −8.53 | −13.23 | 6.16 | −12.19 | −15.80 | −9.34 | −17.05 | 10.70 | −14.18 | −20.23 | −10.01 |
| $LDLJ_r$ | −18.64 | 1.75 | −18.76 | −19.83 | −17.51 | −19.22 | 1.92 | −19.36 | −20.43 | −18.13 | −20.50 | 1.88 | −20.46 | −21.61 | −19.21 |
| $LDLJ_t$ | −8.65 | 1.07 | −8.71 | −9.46 | −7.90 | −8.88 | 1.05 | −8.99 | −9.64 | −8.20 | −9.55 | 1.11 | −9.52 | −10.30 | −8.85 |
| Path Length | 2.64 | 2.99 | 1.74 | 1.01 | 3.28 | 2.93 | 4.58 | 1.78 | 1.11 | 3.26 | 6.63 | 32.05 | 3.12 | 1.60 | 6.59 |
| Time | 7.39 | 3.16 | 6.83 | 5.21 | 8.92 | 7.56 | 3.41 | 6.91 | 5.29 | 8.96 | 11.15 | 6.45 | 9.59 | 7.01 | 12.97 |

TABLE 7

| | Attendings | | | | | Residents | | | | | Novices | | | | |
|---|---|---|---|---|---|---|---|---|---|---|---|---|---|---|---|
| | Avg | Std | Med | Q1 | Q3 | Avg | Std | Med | Q1 | Q3 | Avg | Std | Med | Q1 | Q3 |
| Num Rolls | 53.78 | 36.25 | 45.00 | 30.00 | 66.00 | 61.37 | 38.26 | 52.00 | 36.00 | 79.00 | 110.10 | 102.42 | 78.00 | 48.00 | 131.00 |
| Avg Roll | 0.14 | 0.08 | 0.12 | 0.08 | 0.17 | 0.13 | 0.07 | 0.12 | 0.09 | 0.16 | 0.10 | 0.05 | 0.09 | 0.06 | 0.33 |
| Effective Roll | 1.06 | 0.70 | 0.97 | 0.53 | 1.47 | 1.14 | 0.67 | 1.13 | 0.67 | 1.52 | 1.29 | 0.77 | 1.24 | 0.69 | 1.74 |

TABLE 7-continued

| | Attendings | | | | | Residents | | | | | Novices | | | | |
|---|---|---|---|---|---|---|---|---|---|---|---|---|---|---|---|
| | Avg | Std | Med | Q1 | Q3 | Avg | Std | Med | Q1 | Q3 | Avg | Std | Med | Q1 | Q3 |
| Max Roll Vel | 6.31 | 2.59 | 5.72 | 4.47 | 7.66 | 6.79 | 2.57 | 6.33 | 5.00 | 8.19 | 5.85 | 2.78 | 5.27 | 3.90 | 7.32 |
| Med Roll Vel | 0.48 | 0.19 | 0.44 | 0.33 | 0.60 | 0.56 | 0.21 | 0.53 | 0.39 | 0.68 | 0.43 | 0.18 | 0.40 | 0.29 | 0.53 |
| SPARC | −13.31 | 7.48 | −11.36 | −15.90 | −8.54 | −13.85 | 7.32 | −12.22 | −16.25 | −9.32 | −19.65 | 14.17 | −14.80 | −23.28 | −10.82 |
| $LDLJ_r$ | −18.80 | 1.85 | −18.83 | −19.96 | −17.68 | −19.25 | 2.05 | −19.31 | −20.63 | −18.02 | −20.89 | 2.17 | −20.71 | −22.19 | −19.32 |
| $LDLJ_t$ | −8.89 | 0.98 | −8.93 | −9.58 | −8.27 | −8.98 | 1.02 | −9.06 | −9.69 | −8.26 | −9.63 | 1.24 | −9.65 | −10.39 | −8.84 |
| Path Length | 3.20 | 4.98 | 1.77 | 1.02 | 3.09 | 3.08 | 3.96 | 1.84 | 1.12 | 3.36 | 8.72 | 16.11 | 3.57 | 1.66 | 8.05 |
| Time | 8.09 | 4.12 | 7.21 | 5.41 | 9.34 | 7.96 | 3.84 | 7.11 | 5.38 | 9.50 | 13.79 | 10.48 | 10.69 | 7.17 | 16.26 |

TABLE 8

| | Attendings vs. Residents | | | Attendings vs. Novices | | | Residents vs. Novices | | |
|---|---|---|---|---|---|---|---|---|---|
| | P | CI_L | CI_H | P | CI_L | CI_H | P | CI_L | CI_H |
| Num Rolls | <0.001 | −16.63 | −5.97 | <0.001 | −45.23 | −34.55 | <0.001 | −34.09 | −23.09 |
| Avg Roll | 0.009 | 0.002 | 0.02 | <0.001 | 0.04 | 0.06 | <0.001 | 0.03 | 0.05 |
| Effective Roll | 0.032 | −0.19 | −0.01 | <0.001 | −0.46 | −0.28 | <0.001 | −0.37 | −0.18 |
| Max Roll Vel | 0.001 | −0.84 | −0.17 | <0.001 | 0.42 | 1.10 | <0.001 | 0.91 | 1.61 |
| Med Roll Vel | <0.001 | −0.11 | −0.05 | <0.001 | 0.03 | 0.08 | <0.001 | 0.11 | 0.16 |
| SPARC | 0.172 | −0.24 | 1.65 | <0.001 | 3.73 | 5.63 | <0.001 | 3.00 | 4.95 |
| $LDLJ_r$ | <0.001 | 0.36 | 0.79 | <0.001 | 1.66 | 2.10 | <0.001 | 1.08 | 1.53 |
| $LDLJ_t$ | <0.001 | 0.10 | 0.35 | <0.001 | 0.77 | 1.02 | <0.001 | 0.54 | 0.80 |
| Path Length | 0.714 | −1.23 | 0.65 | <0.001 | −5.14 | −3.25 | <0.001 | −4.87 | −2.93 |
| Time | 0.748 | −0.70 | 0.37 | <0.001 | −4.34 | −3.27 | <0.001 | −4.20 | −3.09 |

TABLE 9

| | Attendings vs. Residents | | | Attendings vs. Novices | | | Residents vs. Novices | | |
|---|---|---|---|---|---|---|---|---|---|
| | P | CI_L | CI_H | P | CI_L | CI_H | P | CI_L | CI_H |
| Num Rolls | 0.053 | −15.25 | 0.07 | <0.001 | −64.02 | −48.62 | <0.001 | −56.65 | −40.81 |
| Avg Roll | 0.158 | −0.002 | 0.02 | <0.001 | 0.03 | 0.05 | <0.001 | 0.03 | 0.04 |
| Effective Roll | 0.074 | −0.16 | 0.01 | <0.001 | −0.31 | −0.14 | <0.001 | −0.24 | −0.06 |
| Max Roll Vel | <0.001 | −0.79 | −0.17 | 0.002 | 0.15 | 0.77 | <0.001 | 0.62 | 1.26 |
| Med Roll Vel | <0.001 | −0.10 | −0.06 | <0.001 | 0.03 | 0.07 | <0.001 | 0.11 | 0.15 |
| SPARC | 0.528 | −0.64 | 1.72 | <0.001 | 5.16 | 7.53 | <0.001 | 4.58 | 7.02 |
| $LDLJ_r$ | <0.001 | 0.21 | 0.69 | <0.001 | 1.85 | 2.32 | <0.001 | 1.39 | 1.88 |
| $LDLJ_t$ | 0.205 | −0.03 | 0.22 | <0.001 | 0.61 | 0.87 | <0.001 | 0.52 | 0.78 |
| Path Length | 0.968 | −1.03 | 1.27 | <0.001 | −6.67 | −4.36 | <0.001 | −6.82 | −4.45 |
| Time | 0.919 | −0.66 | 0.92 | <0.001 | −6.50 | −4.90 | <0.001 | −6.65 | −5.01 |

Figures 16A, 16B:
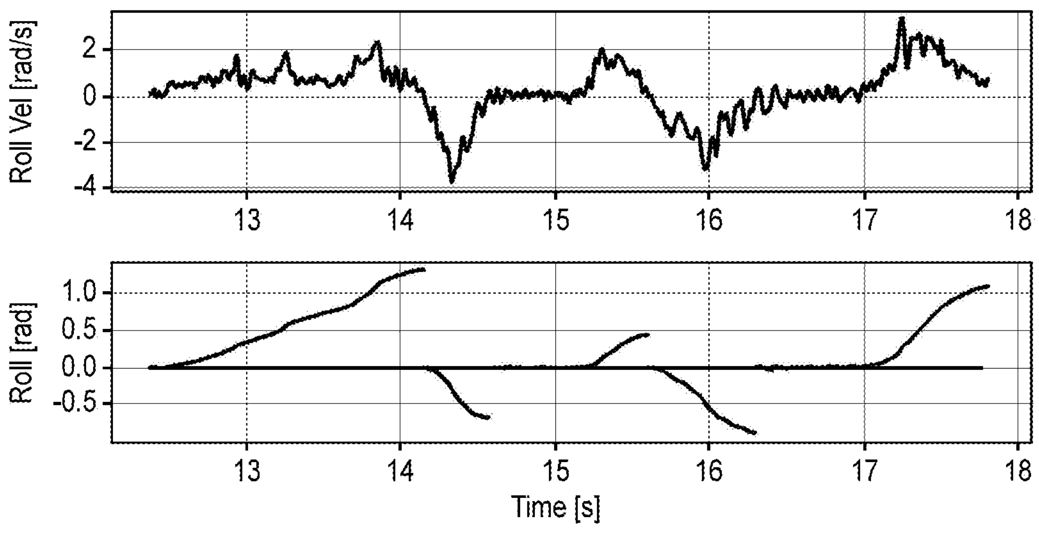
FIG. 16A depicts a graphical comparison of a selected angular velocity time series and corresponding roll-reversal profile for an attending, according to one embodiment.
FIG. 16B depicts a graphical comparison of a selected angular velocity time series and corresponding roll-reversal profile for a novice, according to one embodiment.

To give a better overview of results, FIG. 16A-16B illustrates a comparison of two selected angular velocity time series and corresponding roll-reversal profiles for an attending and novice. As such, the Number of Rolls metric was computed from the roll-reversal profile of all sutures in the dataset. Statistical analysis revealed that attendings demonstrated a significantly greater economy of hand roll in comparison with novices at both surface and depth conditions. This was also observed when comparing residents with novices (novices had significantly greater Number of Rolls). A salient result of this analysis is that Number of Rolls discerned the finer difference in hand movement skill between attending and resident populations.

The Effective Roll scores were significantly less for both attending and resident groups when compared with the novice groups respectively. While this result was observed at both surface and depth conditions, there was a significant difference between attending and resident Effective Roll scores at the surface suturing condition suggesting its value for suturing skill assessment.

The Average Roll Angle metric was similarly able to differentiate between all three groups with the mean scores for both attendings and residents being significantly higher than that of novices at both task conditions. Also, when comparing attendings vs. residents, attendings had a significantly higher mean Average Roll Angle in the surface condition.

Both roll velocity metrics, i.e., Maximum Roll Velocity and Median Roll Velocity, demonstrated similar trends to one another when comparing the three groups. Pairwise Tukey comparisons showed a significant statistical difference between all three clinical levels at both conditions. Both attending. and resident groups had significantly higher mean Max/Median Roll Velocities than the novice group.

Figure 14:
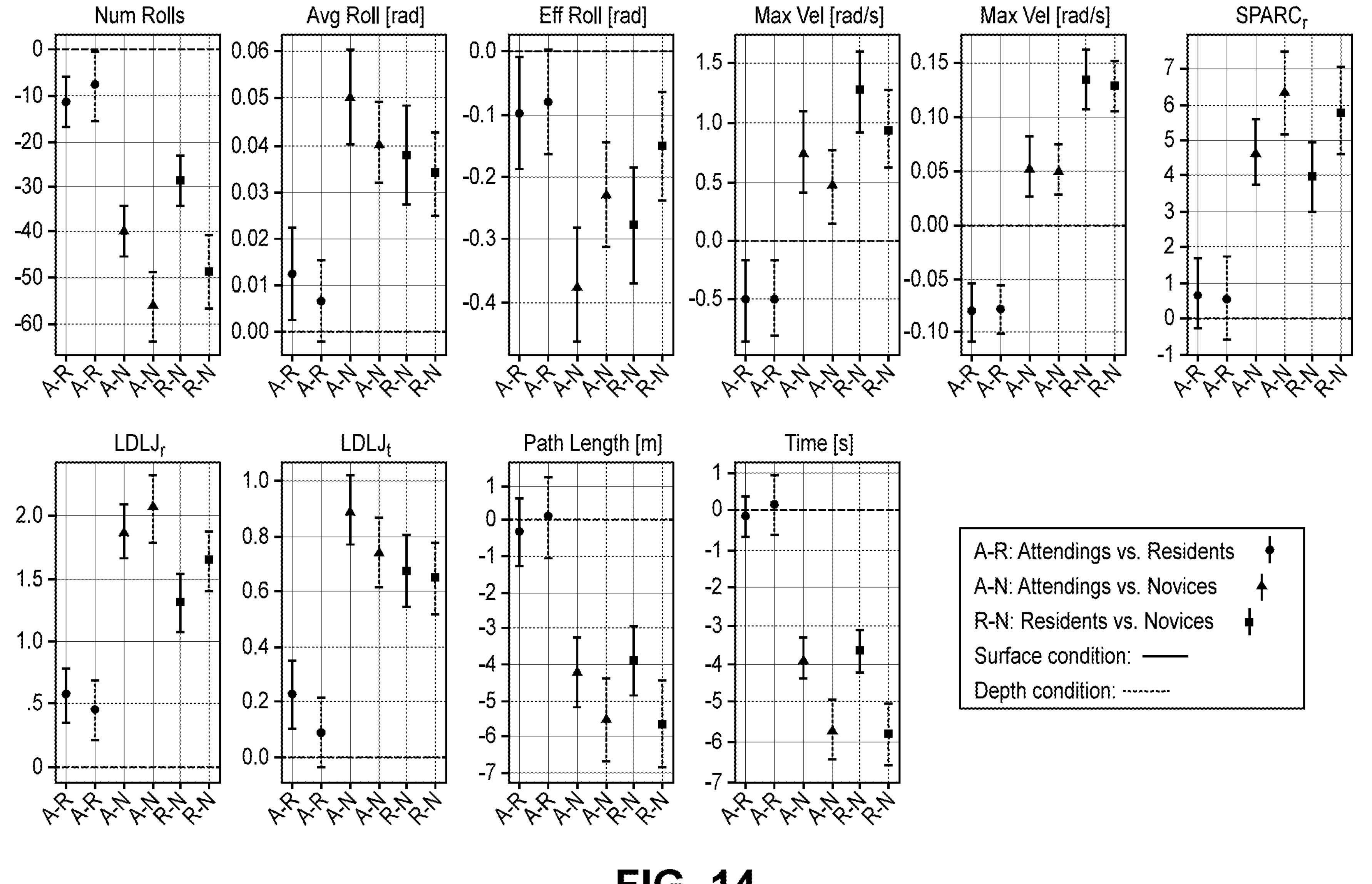
FIG. 14 depicts a graphical representation of the results of pairwise comparisons of suturing skills between three populations, according to one embodiment.
Figure 15:
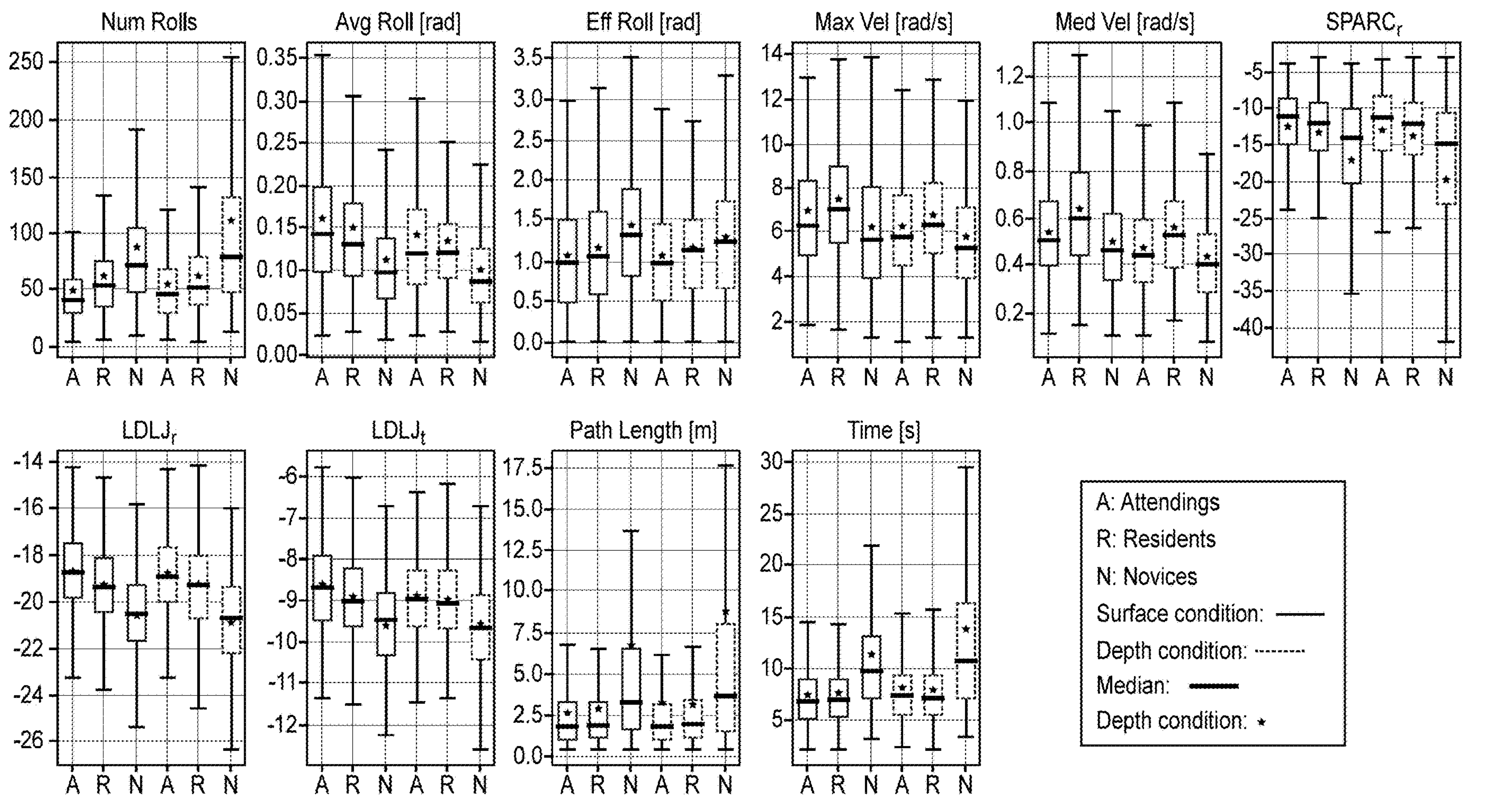
FIG. 15 depicts boxplots of metric scores for the three sample populations to give an overview of all metric distributions, according to one embodiment.

Interestingly, a statistical comparison between the attending and resident groups showed that residents have higher mean Max/Median Roll Velocities than the attendings (FIG. 14).

For measuring hand roll smoothness, LDLJ, demonstrated significantly better mean scores for attendings compared to both residents and novices and significantly better smoothness for residents compared to novices for both surface and depth conditions of the suturing task. Similarly, SPARCr demonstrated significantly better values for pairwise comparisons of attendings vs. novices and residents vs. novices for both conditions. However, unlike LDLJ, when comparing attendings to residents, SPARC, scores could not significantly differentiate between the two groups at either condition. With respect to translational smoothness (LDLJI), post-hoc tests observed the same relationship as LDLJ, except for comparing attendings with residents at the deep suturing condition (which did not indicate a significant difference).

Commonly used metrics Path Length and Time also observed results in line with the previous metrics. Both attending and resident groups were found to be significantly more efficient compared to novices with respect to average suture completion Time and average hand Path Length, at both conditions of the task. However, no significant differences between attendings vs. residents were observed based on Time and Path Length for either task condition.

In summary, all metrics were consistently able to significantly differentiate between attending and novices as well as residents and novices. In addition, when comparing attendings to residents, all metrics were able to significantly differentiate between the two groups for at least one condition of the task (surface or depth) except for SPARCr, Path Length, and Time.

The primary purpose of this example was to examine if sensor measurement of hand movements during CF suturing could reflect participants' technical skill. For this, IMU-based hand motion metrics on the instrumented platform were proposed, specifically designed for comprehensive open radial suturing skill assessment. In line with the validated FVS CF radial suturing task, this system seeks to objectively quantify suturing skill using sensor data. Ultimately, analysis of hand motion data revealed several salient results supporting the effectiveness of hand motion metrics in distinguishing skilled from unskilled CF suturing.

Analysis revealed that the novel hand movement metrics used herein could reliably distinguish between the skill groups as hypothesized. Metrics derived from a participant's roll-reversal profile—Number of Rolls, Effective Roll, and Average Roll Angle-yielded results as expected: for both Number of Rolls and Effective Roll, as clinical experience increased, the metric values generally decreased. In contrast, Average Roll Angle increased with clinical experience. These key metrics demonstrated that with increased clinical experience, participants not only needed a smaller number of hand roll movements to complete each suture, but the "amount" of roll required was also smaller than for less experienced participants. At the same time, the more experienced participants also had a greater average roll, indicating that participants with superior suturing skill rolled their hand to a greater degree per hand rotation. The efficacy of these three hand rotation metrics in particular, for measuring CF suturing skill is evidenced by the fact that they could successfully differentiate between all three skill groups. These results confirm one's intuition that hand rotation is an important aspect of surgical suturing and, indeed, for surgical skill development in general.

Another aspect of the metrics used herein pertained to quantifying the smoothness of hand movements during suturing. As expected, metrics computing smoothness of motion reflected participants' suturing skill; attendings not only demonstrated superior roll economy but also were smoother in executing these motions. Among rotational [LDLJr, SPARC] and translational [LDLJi] smoothness metrics, LDLJr, most powerfully differentiated between all three groups at both suturing conditions. This finding aligned with an underlying hypothesis of this example: metrics computed based on rotational motions are better suited to CF suturing skill assessment than metrics based on translational motions. The other metric that was used to quantify smoothness, SPARCr, did not reflect skill with the same granularity as LDLJr, showing differences only between attendings vs. novices and residents vs. novices. SPARC was not applied to accelerometer data for translational motion analysis based on the guidelines provided in related literature [27]. Ultimately, these results suggest that measures of hand motion smoothness, especially roll smoothness, could be useful for training and assessing suturing skills.

An interesting finding of the hand motion analysis related to the Maximum/Median Roll Velocity metrics: results showed that the resident group overall had the highest hand roll velocity. A potential explanation may lie in the known speed-accuracy trade-off [30,31] wherein residents may be solely concerned about completing the task fast. As a result, they likely sacrifice respect for tissue and accuracy during suturing—also crucial for skilled suturing. On the other hand, attendings better understand the multi-faceted nature of skilled suturing and balance accuracy, speed, and other factors [32], which results in more careful tissue handling and controlled roll motions. This argument could further be supported by referring to LDLJr, which revealed that though residents' have faster rotations, they are not as smooth as attendings, which is important for effective suturing.

The IMU-based metrics presented in this example are process metrics that provide insight into aspects of suturing procedure, not just the outcome. Traditionally, suturing Time was widely used as a readily available metric for skill assessment. However, Time has been shown to be inferior to process metrics that seek to quantify how the suturing task was performed [33]. In addition, the availability of metrics that capture vital aspects of suturing skill—motion, forces, etc.—allows trainees to become cognizant of the multi-faceted nature of this essential skill. For instance, assessing suturing skill simply by looking at the finished product on the FVS CF model poorly correlated with suturing skill (r=. 24); however, live ratings given by expert assessors during suturing showed a high correlation with participants' training experience (r=. 82) since richer and more comprehensive perceptual information was available to the raters[2].

Using a suite of multimodal metrics would also mitigate the potential negative effects of training where students focus solely on task completion time. This is in line with similar possible negative effects that were observed in the current analysis, revealing that even though residents sutured with higher angular velocities, no significant difference existed between residents and attendings with respect to suture completion Time, suggesting that residents did not actually gain any advantage by rotating their hands faster. Moreover, Path Length is another commonly used and relatively simple metric that measures the efficiency of translational movements of the hand[12,21,29]. In this example, Path Length—similar to Time— could not differentiate between attending and resident groups. The inability of Time and Path Length for finer-grained assessment of suturing skill in this example, in contrast with the discriminative efficacy of the rotational motion analysis, further highlights the promise of rotation-based metrics for superior skill assessment.

It should be noted that there was no "ground truth" for suturing skills for purposes of the examples herein. That is, clinical standing (attendings/residents/novices) was implicitly assumed to be commensurate with suturing skill.

In conclusion, a suite of IMU-based metrics with a particular focus on rotational motion analysis was presented. Metric scores were used to draw inferences on the CF suturing performance of subjects, grouped based on their clinical standing. Particularly, rotation-based metrics were shown to be fine-grade differentiators of suturing skill when assessed on the adapted FVS CF task. Consequently, the simulator system can offer objective, accurate, autonomous, and less burdensome possibilities for proficiency-based teaching and assessment of open vascular suturing which is in line with the top research priorities in simulation-based surgical education identified by Stefanidis et al. (2022)[34]. In addition, the simulator system can potentially help facilitate a wider implementation of the FVS by providing a self-guided training solution for practicing CF suturing that can be incorporated into surgical training programs that require FVS. Lastly, the methods and metrics of this example are potentially applicable to different surgical tasks, and the sizable dataset collected for this example supports the generalizability of the results.

EXAMPLE 3

Vascular surgery encompasses a wide range of intricate procedures, including surgeries performed both traditionally ("open" surgery) as well as endoscopically (endovascular surgery). Due to the benefits of endovascular procedures for increasing patient comfort and reducing hospital stay, there is a demand for today's vascular surgery trainees to learn endovascular techniques. Consequently, surgeon educators recognize the need for trainee development in open surgical techniques, as procedures unable to be done endovascularly are relatively more challenging. To determine educational priorities for technical skill learning, a study exploring necessary procedures to include in a vascular surgery curriculum deemed open surgical techniques to comprise two-thirds of the required procedures for a proper curriculum. Among these, anastomotic technique ranked the highest priority. In line with this, vascular surgeon educators have stressed the importance of learning fundamental vascular skills, such as suturing, as foundational for learning advanced surgical techniques. Unskilled suturing can lead to bleeding and tearing, potentially leading to adverse patient morbidity and mortality. Since vascular procedures can be high-risk, proficient suturing is crucial for well-prepared surgeons.

Given the critical role of suturing in open vascular surgery procedures, there is a demand for practical and widespread objective training methods for effective and efficient skills training. Task trainers provide a relatively affordable and reusable training method as a viable alternative to cadaver training, despite diminished anatomical realism. Such trainers excel in facilitating measurable performance in a focused, simulated anatomical environment that typically allows for sensor metrics to provide objective assessment and targeted feedback on specific skills. The appeal of these trainers is evident in their increasing adoption by surgery boards for performance training and assessment tailored to surgical specialties. These trainers utilize game-like training modules to assess performance through expert ratings, time-based metrics, and error-based metrics. As such, task trainers can be valuable pedagogical tools, particularly in instilling fundamental surgical skills.

For task trainers to excel as learning tools, they must incorporate effective metrics that score a trainee on the various characteristics of a surgical procedure. Needle driver motion is frequently evaluated by surgical experts in standardized rating sheets, as a surgeon's ability to manipulate instruments efficiently denotes surgical skill. Thus, this study's primary focus is quantifying the needle driver's distinct motion characteristics during suturing on a simulator. While conventionally used motion metrics, such as path length (PL), average velocity, or the number of peaks in the velocity profile (Pks), offer a foundational approach to motion analysis, these measures are limited in their formulation and can yield varied results in distinguishing clinical expertise. Accordingly, the surgical education community requires more sophisticated metrics to provide trainees with robust skill measurements and meaningful feedback.

Precise instrument handling with minimum hesitation is hypothesized to be associated with smooth motion of the tool, and capturing this behavior holds the potential for effective surgical skills training. While initially used for tracking stroke recovery, motion smoothness is increasingly used as a robust tool for measuring surgical proficiency. Among the various motion smoothness metrics defined in previous studies, log dimensionless jerk (LDLJ) and spectral arc length (SPARC) are considered state-of-the-art in measuring smoothness of motion. To the knowledge of the inventors, there is no application of motion smoothness for open suturing skills assessment.

Surgical skills assessment on open surgery is limited due to the high demand for minimally invasive surgical skills training. This claim is substantiated by a systematic review by Mitchell et al. that found twenty-nine studies on open vascular skills assessment, reporting eight studies on dexterity analysis of hand motions. Although the studies reported positive results in surgical skills assessment and correlation with expert ratings, there is an additional need to quantitatively assess instrument handling motion as these motions are directly related to suturing quality and provide complexity and depth unique from hand tracking. Only a few studies have done so, likely due to the difficulty of instrumentation without interfering with the subject's needle driver maneuverability. Suturing skills assessment for open surgery requires further research, and evaluating tool motions can provide valuable quantification of some of the various characteristics of skilled suturing.

Studies that use tool motion analysis for surgical skills assessment generally evaluate tooltip motion, but the needle driver's rotational motion is integral to open suturing. Recognizing this, Sharon et al. propose analyzing rotational motion for efficient suturing skill quantification and introduce a novel metric, the orientation rate of change (RoC). The study demonstrated potential in their measure by distinguishing expert and novice performance, but the researchers note that their small sample size may affect the generalizability of their results. Similarly, a previous study on the simulator system found metrics applied to rotational hand motions were better suited to differentiate clinical expertise than metrics applied to transitional hand motions. It can be expected that applying complex metrics to rotational motion may better assess instrument handling motion quality pertinent to skilled suturing.

To compare the importance of rotational vs. translational needle driver motions in open suturing, this study applies equivalent metrics to both domains of motion. Additionally, studies on surgical skills assessment have generally succeeded in differentiating between experts (clinicians, surgeon educators) and novices (medical students, subjects with no experience). However, surgical skill assessment has encountered difficulties in determining differences between experts and intermediates (residents), often attributing this to a small sample size. To mitigate this, this dataset consists of 97 subjects with a vast range of experience, ranging from students with no experience to expert vascular attendings with several decades of experience. In this study, the aim is to answer the following questions:

1) Can metrics that quantify tool motion indicate skilled instrument handling?

2) Are metrics that quantify tool rotational motion better suited to assess suturing skill over metrics that quantify tool translational motion?

II. Materials and Methods

A. Simulator Design and Development

The simulator system is a custom-built simulator that renders radial suturing employed in vascular surgery and measures suturing skill comprehensively using multi-modal sensors. The current design features a hollow cylinder with a simulated membrane material attached to the surface. Twelve suture locations are marked in a radial suturing pattern modeled from the Fundamentals of Vascular Surgery simulator. The simulator system simulates suturing at surface and depth conditions simulated through raised barriers. The depth condition represents vascular suturing in an anatomical cavity. Subjects were instructed to complete four trials on the simulator system: one at surface, one at depth, and two more trials of the same sequence. FIGS. 17A-17D demonstrates both simulator conditions. The platform interfaces various sensors for a multi-modal, comprehensive assessment of suturing skill. An internal camera (Intel RealSense D435) automatically performs subcutaneous, vision-based needle tracking, recorded at 60 fps, to synchronize sensor data for suture-specific analysis. A force/torque sensor measures membrane forces during suturing, and two inertial measurement units (IMUs) are placed on a subject's hand and wrist. A previous study on a substantially similar simulator analyzed hand motions obtained from the IMU on the same dataset presented herein. Specifically, this study examines data obtained from two electromagnetic position and orientation sensors (Ascension trakSTAR Model 180, Northern Digital Inc.), recording x, y, and z Cartesian sensor-frame coordinates and azimuth, elevation, roll, and quaternion orientation at a rate of 100 Hz, are attached to both handles of a needle driver (Mayo-Hegar, 8"). Tooltip location is calculated through rotation calibration.

The electromagnetic sensor attachment to the needle driver was designed in a non-intrusive manner for the surgeon to feel comfortable using instrument handling techniques identical to those in the operating room. The sensor is secured through a molded 3D-printed casing and lid, which is then affixed to each handle of the needle driver. One sensor is flipped so the cable can be wrapped around the needle driver and braided with the other sensor to mitigate interference during the suturing procedure. A representation of the orientation of both sensors is seen in FIG. 17A. The sensors are rotated 180 degrees in the x and y axis post-processing to align both sensor's movement profiles.

B. Data Processing

Sensor data for metrics that do not require derivatives were processed with a 20 Hz, 2nd order low-pass Butterworth filter applied to the profile. LDLJ heavily relies on accurate derivative estimations, as a previous study on cannulation needle motions found that noise increases exponentially per derivative calculation. It was found that a window length of 25 best suited rotation calibrated tip motion data, as calibrated tooltip values are noisier than raw data. Thus, a Savitzky-Golay filter of order three and a window span of 25 was used for translational tooltip motion derivatives. For rotational motion derivatives, the low-pass Butterworth filtered data was compared to several Savitzky-Golay parameters and found a window span of 13 best matched the filtered data. For further validation, this parameter was compared with x-angular velocity obtained from an IMU placed in parallel with the EM sensor.

C. Metrics

Figure 18:
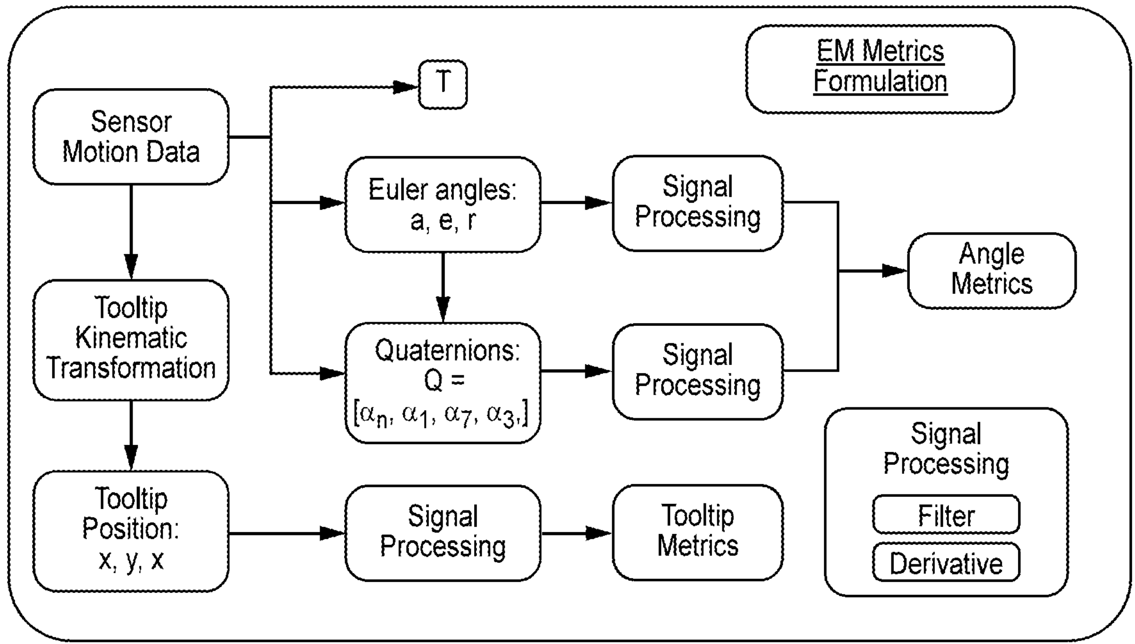
FIG. 18 shows a flowchart describing EM data processing and metrics calculations, in according with one embodiment.

We aimed to establish metrics to pinpoint characteristics of skilled instrument handling needle driver motion. The following section will present the metrics and corresponding formulations used in this paper. Performance is evaluated by suture, and metrics are calculated from the start of needle contact to the surface of the membrane until the tracked needle swage exits the membrane. A flowchart depicting the data processing methods and metric calculations is seen in FIG. 18. Metrics with physical properties deemed applicable to provide feedback were chosen. General formulations will be presented since metrics will be applied to both rotational and translational motion.

To evaluate the needle driver's rotational motion, motion metrics were applied to the x-axis/roll (denoted with r), as the primary angular motions in needle driving encapsulate rotations about this axis. To evaluate the needle driver's translational motion, motion metrics are applied to the calibrated tooltip location (denoted with t). Additionally, the surgeon collaborators frequently stated that a trainee's confidence in their motions when approaching a suture could indicate their suturing skill, leading to the formulation of Suture Approach Confidence metrics. This measure uses a third of the time from the last suture end time to the current suture start time and computes LDLJ and SPARC (denoted with App) on that time window. A list of the metrics used in this study and their application is seen in Table 10.

TABLE 10

| Metric | Tooltip | Roll | Suture Approach Confidence |
|---|---|---|---|
| PL/APL | ✓ | ✓ | |
| Pks | ✓ | | |
| LDLJ | ✓ | ✓ | ✓ |
| SPARC | ✓ | ✓ | ✓ |
| RoC | | ✓ | |
| NoR | | ✓ | |

1) Time (T): The time from needle contact to needle exit. T is the most common measure of surgical skill.

$$T = t_{exit} - t_{entry}$$

2) Path Length (PL): Total distance traversed by the tooltip. PL is a common measure to assess the economy of motion. Theoretically, it can be surmised that a skilled clinician follows minimal displacement to accomplish their surgical procedure. Thus, total tooltip distance and degree of rotation correlate with clinical expertise.

$$\int_{t_{entry}}^{t_{end}} \sqrt{\left(\frac{dx}{dt}\right)^2 + \left(\frac{dy}{dt}\right)^2 + \left(\frac{dz}{dt}\right)^2} \, dt \quad (2)$$

3) Number of Peaks in the Velocity Profile (Pks): A precursory motion metric that measures the number of peaks present in the velocity profile with a minimum prominence of 0.05 mm/s with the findpeaks MATLAB function. The more unsmooth the velocity profile, the greater amount of peaks.

4) Log Dimensionless Jerk (LDLJ): The natural log of jerk integrated and squared, where T and PL are defined above.

$$LDLJ = \ln \left| \frac{T^5}{PL^2} \int_{t_{entry}}^{t_{end}} \left(\frac{d^3x}{dt^3}\right)^2 + \left(\frac{d^3y}{dt^3}\right)^2 + \left(\frac{d^3z}{dt^3}\right)^2 dt \right| \quad (3)$$

5) Spectral Arc Length (SPARC): The arc length of the Fourier transform of the velocity profile.

$$SPARC_r = -\int_0^{\omega_c} \left[ \left(\frac{1}{\omega_c}\right)^2 + \left(\frac{d\hat{V}(\omega)}{d_\omega}\right)^2 \right]^{\frac{1}{2}} d\omega; \quad (4)$$

$$\hat{V}(\omega) = \frac{V(\omega)}{V(0)}, \; V(\omega) = \mathcal{F}\{v(t)\}$$

6) Angular Path Length (APL): Total angular distance observed by the sensors.

$$APL + 2\sum_{i=1}^{N-1} \left(Q(i+1) \cdot Q(i)^{-1}\right) \quad (5)$$

7) Rate of Angular Change (RoC): The rate of change in rotation.

$$RoC = \frac{2}{N-1} \sum_{i=1}^{N-1} \frac{Q(i+1) \cdot Q(i)^{-1}}{t(i+1) - t(i)} \quad (6)$$

8) Number of Rotations (NOR): Building upon the number of rolls metric previously applied to measure hand movements on the simulator system, NoR sums the number of changes in the direction of rotation through roll-axis angular velocity to measure deliberate rotations during suturing performance. A deliberate change in rotation requires an APL greater than 3.6 degrees—1% of the full 360-degree rotation—until the next rotation occurs.

D. Subject Demographics and Statistical Methods

This study evaluated suturing performance of 97 subjects with varying levels of expertise. Ethics approval for this study was provided by Clemson University (IRB number: IRB2020-0387; Date of Approval: May 4, 2021). Participants included attendings with varying degrees of clinical experience, fellows, residents (Post Graduate Year (PGY) 1-5), and novices (medical students and others with no medical experience) on the suturing simulator. A distribution of subject demographics is seen in Table 11.

TABLE 11

| Subject Handedness | Subjects | Surface Trials | Surface Sutures | Depth Trials | Depth Sutures | Total Total Sutures |
|---|---|---|---|---|---|---|
| Right | 89 | 182 | 2177 | 180 | 2152 | 4329 |
| Left | 8 | 16 | 192 | 16 | 190 | 382 |
| Experts | 35 | 71 | 852 | 71 | 847 | 1699 |
| Fellow | 10 | 19 | 228 | 19 | 226 | 454 |
| Attending (<=10 years) | 13 | 26 | 312 | 26 | 310 | 622 |
| Attending (>10 years) | 12 | 26 | 312 | 26 | 311 | 623 |
| Intermediates | 32 | 63 | 756 | 63 | 755 | 1511 |
| PGY1 | 3 | 6 | 72 | 6 | 71 | 143 |
| PGY2 | 5 | 10 | 120 | 10 | 120 | 240 |
| PGY3 | 5 | 10 | 120 | 10 | 120 | 240 |
| PGY4 | 8 | 15 | 180 | 15 | 180 | 360 |
| PGY5 | 11 | 22 | 264 | 22 | 264 | 528 |
| Novices | 30 | 64 | 761 | 62 | 740 | 1501 |

As noted in the table, some subjects were unable to complete all four trials or all twelve sutures.

Statistical analyses were computed using R (version 4.2.2). Tukey HSD tests for multiple pair-wise comparisons between the three levels of clinical standing are computed for each metric. The model uses Tukey's multiplicity adjustment to account for the family-wise error rate based on the number of comparisons made, similar to ANOVA. The linear model fits each metric with the level of clinical standing while controlling for suture location, subject handedness, and the interaction between the two variables, as suturing technique and the needle driver's position and orientation depend on such factors. To analyze the relationships between the metrics, correlation matrices were generated for surface and depth trials.

III. Results

Figure 19:
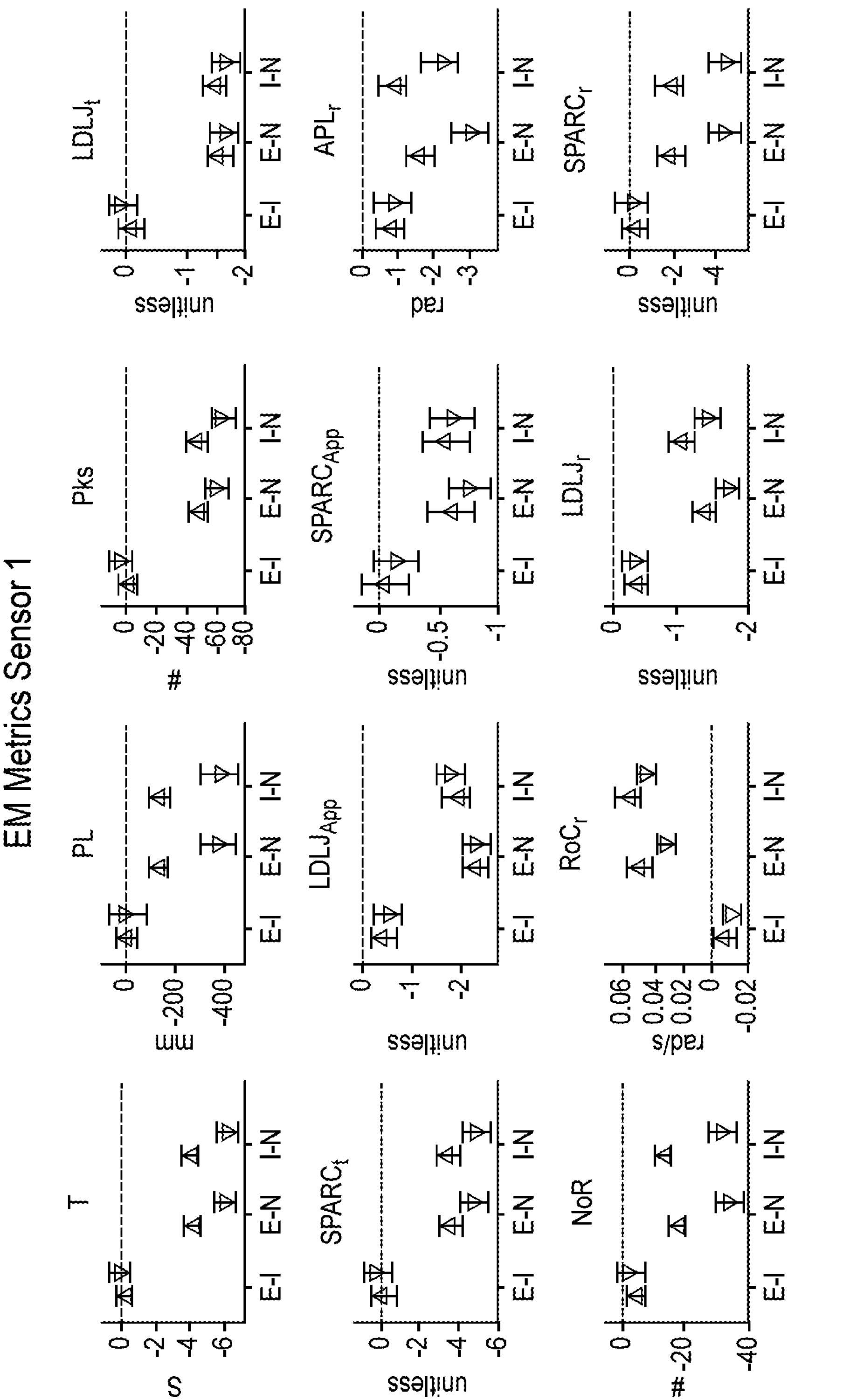

The pair-wise TukeyHSD comparison results calculated from sensor 1 are seen in FIG. 19. All metrics observe similar results between sensor 1 and sensor 2. As such, results from sensor 2 are only presented in the supplementary materials. Additionally, pair-wise Tukey HSD p-value results are recorded in Table 12.

TABLE 12

| | Surface | | | | | | Depth | | | | | |
|---|---|---|---|---|---|---|---|---|---|---|---|---|
| | Sensor 1 | | | Sensor 2 | | | Sensor 1 | | | Sensor 2 | | |
| Metric | E-I | E-N | I-N | E-I | E-N | I-N | E-I | E-N | I-N | E-I | E-N | I-N |
| Tooltip Metrics | | | | | | | | | | | | |
| T | 0.480 | 0.000* | 0.000* | N/A | N/A | N/A | 0.766 | 0.000* | 0.000* | N/A | N/A | N/A |
| PL | 0.973 | 0.000* | 0.000* | 0.968 | 0.000* | 0.000* | 0.997 | 0.000* | 0.000* | 0.991 | 0.000* | 0.000* |
| Pks | 0.841 | 0.000* | 0.000* | 0.808 | 0.000* | 0.000* | 0.445 | 0.000* | 0.000* | 0.375 | 0.000* | 0.000* |
| $LDLJ_t$ | 0.434 | 0.000* | 0.000* | 0.419 | 0.000* | 0.000* | 0.971 | 0.000* | 0.000* | 0.965 | 0.000* | 0.000* |
| $SPARC_t$ | 0.877 | 0.000* | 0.000* | 0.757 | 0.000* | 0.000* | 0.999 | 0.000* | 0.000* | 0.893 | 0.000* | 0.000* |

TABLE 12-continued

| | Surface | | | | | | Depth | | | | | |
|---|---|---|---|---|---|---|---|---|---|---|---|---|
| | Sensor 1 | | | Sensor 2 | | | Sensor 1 | | | Sensor 2 | | |
| Metric | E-I | E-N | I-N | E-I | E-N | I-N | E-I | E-N | I-N | E-I | E-N | I-N |
| $LDLJ_{App}$ | 0.002* | 0.000* | 0.000* | 0.004* | 0.000* | 0.000* | 0.010* | 0.000* | 0.000* | 0.000* | 0.000* | 0.000* |
| $SPARC_{App}$ | 0.820 | 0.000* | 0.000* | 0.957 | 0.000* | 0.000* | 0.889 | 0.000* | 0.000* | 0.109 | 0.000* | 0.000* |
| Rotational Metrics | | | | | | | | | | | | |
| $APL_r$ | 0.000* | 0.000* | 0.000* | 0.000* | 0.000* | 0.000* | 0.000* | 0.000* | 0.000* | 0.000* | 0.000* | 0.000* |
| $RoC_r$ | 0.032 | 0.000* | 0.000* | 0.019 | 0.000* | 0.000* | 0.000* | 0.000* | 0.000* | 0.000* | 0.000* | 0.000* |
| $LDLJ_r$ | 0.000* | 0.000* | 0.000* | 0.000* | 0.000* | 0.000* | 0.000* | 0.000* | 0.000* | 0.002* | 0.000* | 0.000* |
| $SPARC_r$ | 0.763 | 0.000* | 0.000* | 0.789 | 0.000* | 0.000* | 0.999 | 0.000* | 0.000* | 0.990 | 0.000* | 0.000* |
| NoR | 0.000* | 0.000* | 0.000* | 0.000* | 0.000* | 0.000* | 0.343 | 0.000* | 0.000* | 0.476 | 0.000* | 0.000* |

Among the tooltip metrics, LDLJApp emerged as the sole metric capable of distinguishing between expert and intermediate performance in both superficial and depth conditions. In contrast, angular-based metrics showed improved performance compared to the tooltip metrics, with 4/5 metrics successfully distinguishing between experts and intermediates in the surface condition and 3/5 in the depth condition. SPARCr failed to differentiate between expert and intermediate performance in both conditions, and NoR could not do so in the depth condition.

Figure 21:
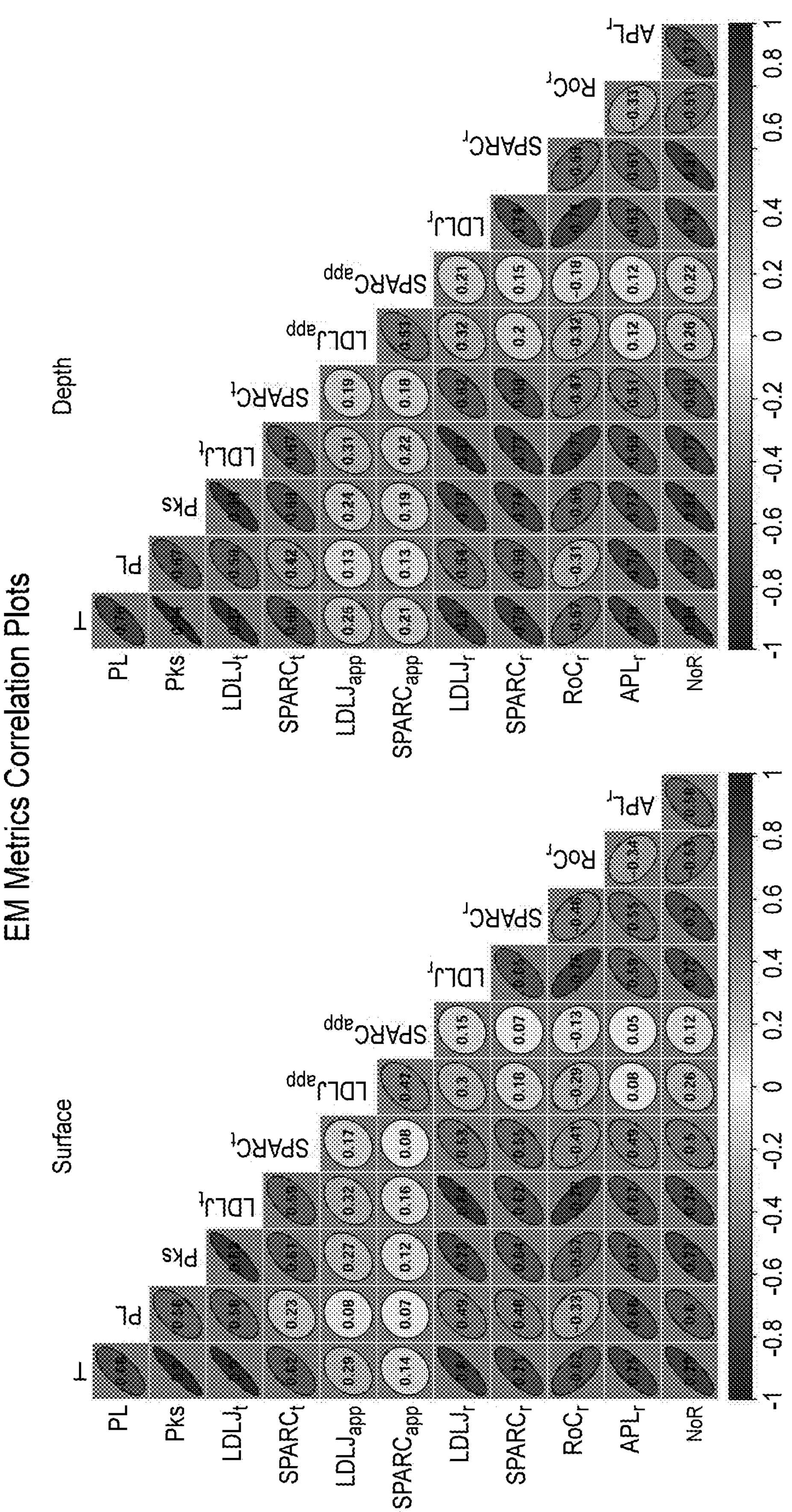
FIG. 21 depicts correlation matrices visualizing the relationships between all metrics defined in the study in the surface condition (left) and the depth condition (right), according to one embodiment.

Correlation matrices from surface and depth trial metrics revealed high correlations across translational and rotational metrics, particularly with T (FIG. 21). Among the translational metrics, Pks and LDLJt demonstrated the highest correlations with T (surface: Pks=LDLJt=0.9, depth: Pks=0.94 and LDLJt=0.87). Likewise, for rotational metrics, LDLJr and NoR observed the highest correlation with T (surface: LDLJr=0.8 and NoR=0.79, depth: LDLJr=0.8 and NoR=0.89).

IV. Discussion

The importance of skilled instrument handling in suturing signifies the potential for tool motion metrics for suturing skills assessment. In support of this claim, all metrics analyzed in this study effectively differentiated novice from intermediate or expert suturing performance. The discussion begins by focusing on the results of the traditional translational tooltip metrics and T. T, PL, and Pks were unable to differentiate between expert and intermediate skill levels. Studies incorporating these metrics have found similar difficulties in separating expert clinician and intermediate resident groups, noting their limitation for more nuanced levels of skill assessment. Thus, determining the fine-grain differences between the expert and intermediate skill levels will allow for better assessment of skilled instrument handling characteristics for targeted skills analysis and improved feedback.

More advanced motion smoothness metrics have been found to be effective in surgical skills analysis, although only a few studies have incorporated them thus far. Results from FIG. 19 demonstrate that the sole tooltip measure to differentiate between experts and intermediates was found from one of the new applications of smoothness defined in this study LDLJApp, whereas SPARCApp, SPARCt and LDLJt could not. Despite SPARC being developed to address LDLJ's limitations of sensitivity to noise, this study evidenced that SPARC and LDLJ have varying results in terms of superiority. For example, LDLJApp was designed to preemptively assess a surgeon's confidence before suturing, quantifying movements that are highly related to the original purpose of LDLJ to assess stroke rehabilitation in hand motion tasks. In summary, while tooltip metrics effectively distinguish novice from intermediate and expert skill levels, they appear to have limited value in differentiating experts and intermediates.

We hypothesized that the most potent suite of metrics for measuring adept suturing skills from instrument handling could be derived from its rotational time series data. Recent seminal research by Sharon et al. has offered insights into the potential of rotational motion metrics. In their study, they found that, while angular displacement (APL) could not differentiate expert surgeon performance from non-medical graduate students in the open needle driving trial, it could do so in the teleoperated condition. Conversely, we found that APLr was among the most effective metrics, observing significant differences between all groups for both conditions. It is important to note that Sharon et al. highlight limitations in their work deriving from a small sample size and the lack of subjects with more varied levels of clinical expertise, likely leading to the differences in observed results. It can be surmised that the more experienced the user, the fewer needle-driving rotations are necessary to complete the suture. This conjecture is further validated through one of the new metrics introduced in this study, NoR, which was able to differentiate between all three groups in the superficial condition. The measure captures the amount of discrete, intentionally made rotations about the needle driver's roll axis. The initial assessment of rotational-based position metrics demonstrates substantial improvements over their translational counterparts, further evidenced by a previous study on the simulator platform analyzing IMU hand motions on the same dataset used in this study.

Towards the more computationally advanced rotational metrics, RoCr differentiated between expert and intermediate scores in both conditions. However, unlike the other metrics in this study, the intermediate group observed increased RoC scores over experts and novices in FIG. 20 instead of the gradual trend towards lower values from novices to experts. Sharon et al. did not have an intermediate resident population in their study, thus not experiencing these results. Experts are likely effectively utilizing the speed-accuracy trade-off, driving their needle at a slower, constant rotational speed to minimize the errors present during suturing. Overall, metric shows potential for suturing skills assessment by allowing objective feedback on adjustments in rotational speed for experts and intermediates.

Figure 20:
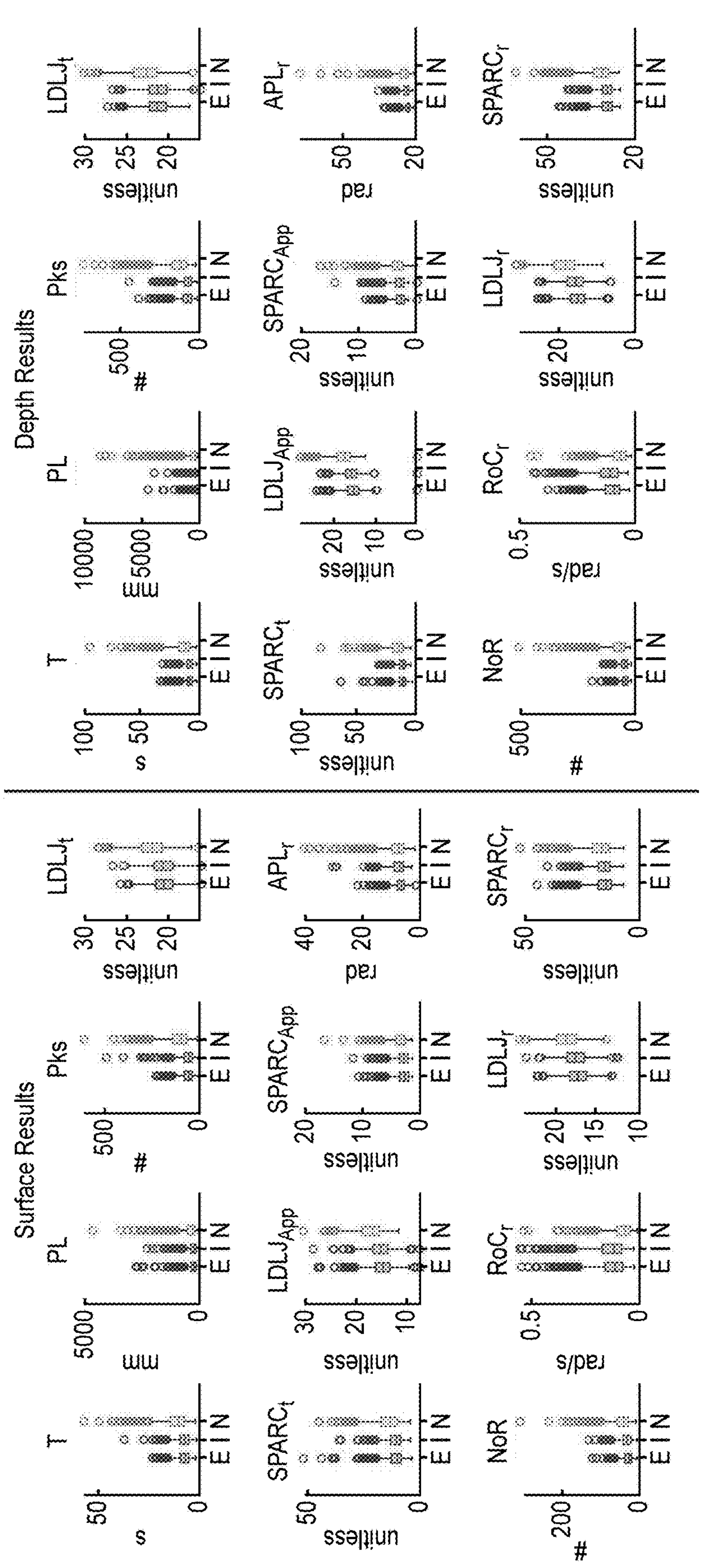
FIG. 20 depicts a graphical representation of score distributions of surface and depth metrics that observed significant differences between experts and intermediates from sensor 1, according to one embodiment.

The final set of metrics, rotational motion smoothness metrics, has demonstrated remarkable efficacy in distinguishing between the various levels of clinical experience. The LDLJr metric successfully distinguished between expert and intermediate groups in both conditions, whereas its SPARC counterpart did not. This is in line with two studies that applied LDLJ and SPARC for rotational motion IMU motion. These results suggest that the differences in metrics' formulation sensitize them to unique task-specific features of motion, as evidenced by the results herein. Nonetheless, LDLJr continues to provide robust results for surgical skills assessment, observing much lower variability than the APLr metric as seen in FIG. 20. The use of smoothness measures as a robust measure of surgical skill continues to show promising results with budding potential for further exploration in various applications.

High correlations were observed between many of the evaluated metrics. In particular, metrics were highly correlated with T, including Pks, LDLJt, LDLJr, and NoR. These findings align with the metrics' quantification of smoothness: a subject with a longer suture completion time (T) would likely exhibit shakier movements reflected by their velocity (Pks), further amplified in jerk (LDLJ). LDLJ's independence of time (due to its dimensionless nature) strengthens this idea. Studies by Hogan and Sternad and Balasubramanian et al. demonstrated that the same movement characteristics result in the same LDLJ or SPARC value regardless of movement duration.

It should be noted that the instant example does not have a measure of task completion or expert ratings. Ultimately, the aim is to develop the simulator system into an assessment tool that follows Messick's framework of validity: content validity, response process, internal structure, relationship to other variables, and consequences. The current work, however, provides evidence for content validity by modeling a procedure deemed relevant to vascular surgery skills training. In addition, both content validity and relationship to other variables were demonstrated by establishing mean score differences between population groups of known levels of clinical expertise. Previous studies have noted the difficulties of defining an expert and argued that expertise is not solely defined by the amount of experience. However, the large number of participants analyzed in this dataset may help to mitigate the effects of noise introduced with these categorizations of skill.

A. Conclusion

In summary, this study has demonstrated the efficacy of the metrics in distinguishing among the three groups of study participants: (1) attending surgeons and fellows, (2) residents, and (3) novices, including both medical and non-medical students. We observed remarkable success with rotational LDLJ and APL metrics, effectively differentiating between all groups in both conditions. In contrast, only one tooltip measure achieved similar success in differentiation. The analysis of open needle driving motion characteristics reveals that rotational motion metrics were more consistent in assessing open suturing skill, highlighting the vast potential for assessing rotational motion for specific surgical skills. Motion smoothness metrics, particularly LDLJ, have exhibited substantial promise in this regard. To the knowledge of the inventors, no prior studies have specifically assessed open suturing skills using rotational motion smoothness metrics.

EXAMPLE 4

Objective assessment of surgical skill using bench-top simulators often implement sensor-based metrics validated through clinical expertise. However, such methods lack specificity, as broad categorizations of skill do not reflect trial-based performance. To establish clinical relevancy, an alternative approach is needed. Expert evaluations of simulator trials allow for a direct comparison of sensor-based metrics, as expert assessment is invaluable for surgical skill evaluation. This study investigates the relationship between sensor-based metrics and expert ratings on the simulator platform, a bench-top simulator for evaluating and training open vascular suturing. The simulator aims to enhance open suturing assessment by utilizing a comprehensive suite of sensors to capture various possible aspects of skill: needle driver motions (tracked by electromagnetic sensors), hand motion (inertial measurement unit), membrane forces and torques, and subcutaneous suture movement (tracked through internal camera computer vision). Previous studies on the simulator system demonstrated that metrics derived from these sensors found population level performance differences between attending surgeons and fellows, residents, and novices. In this study, expert rated performance of 94 subjects was evaluated on the simulator. Individual linear regressions were employed to analyze the association of each sensor metric, along with a metric reflecting a subject's efficiency in their suturing approach (LDLJApp), with the experts' ratings. This study found that each of the four sensors contributed metrics that observed a significant, strong association with expert ratings, with effect sizes comparable to time, a standard measure of surgical competency. These findings emphasize the advantage of using multiple sensors to capture the comprehensive skill evaluation experts provide.

1 Introduction

Vascular surgery requires high proficiency in suturing skills to execute intricate procedures like anastomoses. Mastering this delicate manipulation of vessels hinges on practical surgical training, with studies demonstrating a direct correlation between surgical proficiency and improved patient outcomes. However, accurately assessing these suturing skills for training remains a significant challenge.

Traditionally, senior surgeon-educators provide necessary assessment with valuable feedback shown to have improved trainee performance. Standardized frameworks like Fundamentals of Endovascular Surgery (FEVS) and Fundamentals of Laparoscopic Surgery (FLS) incorporate global rating scales (GRS) for experts to assess skills within their respective specialties. The FEVS and FLS models are typically used in conjunction with simulation-based training, which provides a controlled environment conducive to repeatable practice. The flexibility of GRS allow experts to focus on critical facets of a procedure, regardless of whether training occurs in the operating room or a simulated setting. Notably, minimally invasive surgeries like laparoscopy benefit from these frameworks due to their inherent complexity and advanced training requirements. However, Sheahan et al. highlighted the need for advanced training methods in traditional, open vascular skills, emphasizing the relatively greater difficulty of vascular procedures that cannot be done endoscopically, thus developing of the Fundamentals of Vascular Surgery (FVS) curriculum. Their pilot program found differences in expert assessment scores between junior (postgraduate year [PGY] 1-2) and senior (PGY 3-5) trainees.

While expert assessment remains the gold standard for surgical skill evaluation, its effectiveness is limited by time constraints and reliance solely on what can be readily perceived through human observation. Integrating resident training into live surgeries increases operating times and burdens already busy surgeons. Further, the intricacy of the assessed surgical procedure affect the assessor's workload. A systematic review of vascular surgery skills assessment found that more complex procedures tend to have a greater number of GRS/checklist categories. This, in turn, increases the time and effort required for an expert to become thoroughly familiar with the evaluation process. Additionally, the reliance of visual observation prevents a holistic evaluation of all aspects of a surgical procedure. For example, in suturing, where meticulous suturing technique minimizes harm to vessel and tissue, experts cannot directly assess subcutaneous needle movement. Further, the OSATS "Respect for Tissue" category relies on uncontrolled movements that pull and tear the membrane observable by an expert without incorporating any quantitative force data. This lack of granular detail makes it challenging to assess applied forces and provide feedback for incremental skill improvement. Lastly, expert assessments can be susceptible to bias. Christensen et al. highlight subjectivity in expert evaluation, where factors such as a subject's demeanor or empathetic behavior influenced the expert's ratings. Fung et al. also found that surgeon educators tend to rate the collective performance of a subject rather than an individual trial or procedure. Given these limitations and surgeons' invaluable time, objective and automated methods of assessment are crucial, particularly in the research-scarce field of open vascular education.

Towards this, the controlled nature of simulation-based training facilitates an ideal environment for sensor-based skill evaluation through isolated, repeatable surgical tasks. This approach offers objective and quantifiable analysis through metrics calculated from sensor data. The validity of these metrics is often demonstrated by their ability to differentiate between populations of subjects (e.g., attending surgeons vs. novices) or correlations with clinical expertise (e.g., across resident PGY levels). However, as with expert ratings, simulator-derived proficiency metrics have inherent limitations that require extensive validation prior to widespread use in surgical education.

A key limitation in sensor-based surgical skills assessment is that clinical experience is often assumed to equate to clinical skill. That is, years of clinical experience is assumed to be directly proportional to degree of skill. While this assumption holds some truth, studies in hemodialysis cannulation skills assessment found that GRS scores were much more accurate in indicating skilled performance than years of experience when measured against objective outcomes. Although the study populations consisted of nurses or technicians, they highlight the potential pitfalls of solely relying on clinical experience as a measure of competence.

Sensors excel at capturing fine-grained, quantitative data within their specific domain. For example, quantifying surgical hand motion is a popular area of assessment, often correlated with surgical skill. However, a study by Porte et al. (2007) found that feedback on hand motion efficiency alone was less valuable for skill improvement and retention compared to expert feedback. As evidenced by the OSATS categories of "Respect for Tissue," "Instrument Handling," and "Time and Motion," expert evaluation includes diverse facets of a surgical procedure, factors beyond a single sensing domain. To overcome this limitation, data from multiple sensing modalities is ideal for a comprehensive assessment of surgical skill. The combination of sensors allow for a more holistic evaluation of a trainee's skill and provision of targeted feedback across various facets of performance.

Practical skill development in simulation-based training should prioritize both "simple" foundational tasks crucial to learning advanced surgical techniques and the development of diverse, interpretable metrics evaluating all aspects of a surgical task. The simulator platform exemplifies this approach by leveraging multi-modal sensor data that, for the first time, comprehensively captures open radial suturing skills. In this example, the simulator-based metrics will be examined using the established gold standard of expert ratings via GRS.

This study aims to better understand both objective sensor-based metrics and subjective expert ratings for improved suturing skill assessment. The primary objective of this study is to explore the relationship between these two assessment types to leverage their unique strengths. Sensor metrics provide detailed, quantifiable data that capture even subtle aspects of performance that might be missed by human observation. On the other hand, expert ratings incorporate the valuable procedural and stylistic knowledge of human experience. While some previous studies have correlated the two assessment types, this research will determine the value of individual sensor metrics through their relationship with expert ratings.

The secondary objective of this study is to quantitatively examine which of the four modalities-needle movement, applied forces and torque, tool motion, and hand kinematics—are best associated with GRS scores. As such, this study aims to pave the way for more comprehensive assessment and training on the simulator system by identifying the most effective sensor metrics for suturing skills assessment.

2 Methods 2.1 Simulator System Description

The simulator platform comprises a hollow cylinder housing a synthetic membrane (see FIG. 22A). All instrumented sensors capturing data from hand and needle driver motion, membrane forces/torques, subcutaneous needle movement, and external video recording are synchronized through C++ (Microsoft Visual Studio 2017). A trial consists of 12 sutures in a radial clock face pattern in both "surface" or "depth" conditions. "Surface" trials simulated direct suturing on a superficial blood vessel, while depth trials mimicked suturing deep within an anatomical cavity.

2.2 Sensor Information

Detailed information on the sensors used in the simulator system is presented here as well as in Table 15. In addition, FIG. 22A and FIG. 22B show the placement of the various sensors on the simulator system. More specifically, FIG. 22A depicts an image of the simulator platform detailing the placement of various sensors and equipment. A ring light enclosing the external camera is used to maintain consistent lighting. The internal camera is positioned at the base of the membrane cylinder, while the force/torque sensor is affixed underneath the cylinder. The electromagnetic (EM) field generator tracks the position and orientation of EM sensors affixed to the needle driver through EM sensors on the needle driver. The EM sensors and the IMUs are seen in FIG. 22B. Further, FIG. 22B depicts the survey interface used to gather expert ratings. Raters can use sliders on each skill category to evaluate a subject's performance on a scale from novice to expert.

Computer Vision Needle Tracking and External Recording (Cameras): Needle movement was tracked through advanced computer vision algorithms to provide information about unnecessary needle sway and behavior that may damage or harm the surrounding tissue. The metrics developed to capture this behavior successfully differentiated between attending surgeon and resident performance in the initial version of the simulator system. An external camera recorded subject performance at 30 Hz, placed to minimize identifying subject information.

Membrane Force and Torque (Force/Torque Sensor): In the initial iteration of the simulator system, Kil et al. compared differences in expert and intermediate Fp+, Fp-, and Fpp metrics in the z, orthogonal, and tangential directions, generally differentiating z and orthogonal forces with less consistent results in the tangential direction. There work was expanded through a fresh and extensive dataset and incorporated more complex force metrics.

Instrument Handling (Electromagnetic Tracker): Studies in surgical skills analysis assessing surgical tool or hand motion often evaluate the quality of translational motion. However, in suturing, rotational motion is far more relevant to the quality of suture completion than translational motion. Recognizing this, Sharon et al. formulated new metrics to capture needle driver orientation.

Hand Kinematics (IMU): Several studies have highlighted the potential for analyzing hand motions for assessing vascular skills, successfully differentiating metric values between attending surgeons and novices. Building upon this work, Shayan et al. developed metrics to quantify translational and rotational surgical hand movements during suturing on the simulator system.

TABLE 13

| The SutureCoach Global Rating Score | | | | | |
|---|---|---|---|---|---|
| | 1 | 2 | 3 | 4 | 5 |
| Suturing Technique | Unsteady/unorthodox grip, failure to follow the curvature of the needle, hesitant or awkward strokes, uses two hands. | | | | Smooth, purposeful, and steady movements, appropriate angle of entry, decisive action, clear economy of motion, minimal use of both hands. |
| Efficiency between Sutures | Excessive time or hesitation between sutures, false starts, excessive needle repositioning, slow. | | | | No hesitation between sutures, loads needle appropriately on first attempt, no false starts, minimal wasted motion. |
| Body Posture | Rotates body more than 30 degrees from neutral, bends over the table, stiff or awkward. | | | | Minimal body rotation, does not reach across the table, excellent body position, confident. |

2.3 Establishing a Custom Rating Interface

Collaborating with four vascular surgeon educators, an adapted GRS interface was developed tailored to the simulator system external video recordings. The surgeon-collaborators were presented with ten randomly selected videos of participants' first surface trials and multiple video conference sessions. The collaborators achieved consensus on the following key categories for evaluating suturing performance with the simulator system:

1. Suturing Technique 2. Efficiency between Sutures 3. Body Posture

The same collaborators received detailed instructions for scoring each video based on the adapted GRS. For instance, poor Suturing Technique was characterized by an unsteady or unorthodox grip, failure to follow the curvature of the needle, two-handed manipulation, and hesitant or awkward strokes. Similarly, excessive time between sutures, false starts, and frequent needle repositioning indicated poor Efficiency between Sutures. Finally, significant body rotation or "twisting" exceeding 30 degrees, excessive bending over the table, and stiff or awkward posture contributed to a poor Body Posture score. The specific criteria for each category are further detailed in the adapted GRS rating sheet presented in Table 13.

To facilitate efficient and consistent ratings, a custom survey interface was created for raters to view recorded videos and directly assess each subject (Qualtrics, Provo, UT). For each category, a slider facilitates rating on a five-point Likert scale, where 0 corresponded to novice skill level, 2.5 represented intermediate, and 5 indicated expert performance. The numbers were hidden to allow for an evaluation based on an impression of a subject's skill category. FIG. 22B showcases a sample of this survey interface. The four raters were randomly assigned 48 or 49 videos of a subject's second surface trial, with each trial reviewed by two independent raters. Individual scores were then averaged for each trial, and the three category scores were averaged into an overall (Average Rating) for each subject.

TABLE 14

| Clinical Expertise | Subjects | Technique | Efficiency | Posture | Ave Rating |
|---|---|---|---|---|---|
| Novices | 29 | 1.08 | 1.40 | 1.38 | 1.29 |
| Residents | 31 | 3.24 | 3.65 | 3.63 | 3.51 |
| PGY1 | 3 | 3.53 | 3.88 | 4.06 | 3.82 |
| PGY2 | 5 | 3.20 | 3.80 | 3.80 | 3.60 |
| PGY3 | 5 | 2.87 | 3.34 | 3.37 | 3.19 |
| PGY4 | 7 | 3.25 | 3.56 | 3.77 | 3.53 |
| PGY5 | 11 | 3.33 | 3.73 | 3.48 | 3.52 |
| Experts | 34 | 3.40 | 3.88 | 3.77 | 3.68 |
| Fellow | 9 | 3.32 | 3.76 | 3.52 | 3.53 |
| Attending (<10 years) | 11 | 3.26 | 3.87 | 3.74 | 3.62 |
| Attending (≥10 years) | 14 | 3.57 | 3.96 | 3.95 | 3.82 |

3 Subject Demographics

This study analyzes a dataset of 97 subjects of varying clinical expertise (32 subjects with no experience, 30 residents (PGY 1-5), and 35 attending surgeons/fellows). Three trials were excluded from the analysis due to biased resting forces caused by an error in the simulated barrier placement during data collection, resulting in a remaining 94 subjects. Table 14 details the distribution of subjects used in this study and their average rating per category.

3.1 Sensor-Derived Metrics

To analyze the research questions for this study, performance data was extracted for the twelve individual sutures for each user's trial. Suture start time was determined from initial needle contact (obtained from the force/torque sensor) to needle exit detected via computer vision. Since subjects were rated by trial, each subject's sutures were aggregated for expert review and ratings.

The following are metrics that have been used in this study to comprehensively assess open vascular suturing skill. A subset of these metrics were previously demonstrated to be effective in skill assessment on previous and current versions of the simulator system. Also, several of the metrics below have been applied more than one facet of skill measurement (e.g., the total distance metric was computed for tool, hand, and needle motion). The descriptions and utility of metrics used in this study are listed in Tables 15 and 16.

Time (T): a ubiquitous metric in surgical skill evaluation. T relies on the intuitive assumption that greater proficiency results in a shorter completion time. While T serves as a basic measure of competency, the measure lacks the granularity needed to pinpoint specific areas for improvement.

$$T = t_{exit} - t_{contact} \quad (1)$$

Path Length (PL): A common measure of the economy of motion. Theoretically, the more experienced the user, the less distance traveled by the tool, hand, or needle.

$$PL = \int_{t_{contact}}^{t_{end}} \sqrt{\left(\frac{dx}{dt}\right)^2 + \left(\frac{dy}{dt}\right)^2 + \left(\frac{dz}{dt}\right)^2}\, dt \quad (2)$$

Number of Peaks (Pks): A count of the number of peaks in a motion or force profile.

Log Dimensionless Jerk (LDLJ): One of two predominant motion smoothness measures, LDLJ relies on the assumption that smooth motion requires minimal jerk, or continuous change in acceleration. Jerk is squared, integrated, and then made dimensionless to account for intermittency within the profile. The dimensionless calculation should follow the measured field of motion.

LDLJ for Needle driver orientation and tip position:

$$LDLJ{-}PL = \ln\left|\frac{T^5}{PL^2}\int_{t_{contact}}^{t_{exit}} \left(\frac{d^3x}{dt^3}\right)^2 + \left(\frac{d^3y}{dt^3}\right)^2 + \left(\frac{d^3z}{dt^3}\right)^2 dt\right| \quad (3)$$

LDLJ for Hand angular velocity:

$$LDLJ{-}V = \ln\left|\frac{T^3}{v_p^2}\int_{t_{contact}}^{t_{exit}} \left(\frac{d^2V}{dt^2}\right)^2 dt\right| \quad (4)$$

LDLJ for Hand linear acceleration:

$$LDLJ{-}A = \ln\left|\frac{T^3}{a_p^2}\int_{t_{contact}}^{t_{exit}} \left(\frac{dA}{dt}\right)^2 dt\right| \quad (5)$$

Where vp and ap refer to peak velocity and acceleration, respectively.

Spectral Arc Length (SPARC): The other prominent motion smoothness metric, SPARC, captures submovement characteristics of a movement profile, including magnitude and distance between submovements through the Fourier transform of a speed profile.

$$SPARC_r = -\int_0^{\omega_c}\left[\left(\frac{1}{\omega_c}\right)^2 + \left(\frac{d\hat{V}(\omega)}{d_\omega}\right)^2\right]^{\frac{1}{2}} d\omega; \quad (6)$$

$$\hat{V}(\omega) = \frac{V(\omega)}{V(0)}$$

Where V (w) is the Fourier transform of velocity.

3.2 Statistical Analysis

Sensor metrics were averaged across the 12 sutures within each trial for analysis. To explore the relationship between these metrics and expert ratings, independent linear regressions were performed against each rating category for each sensor metric and the recently developed metric, LDLJApp. This metric assesses the smoothness of the needle driver's tip motion between sutures and was designed to capture a subject's efficiency before suturing-a factor frequently commented on by the Expert Raters and included as a category for rating (Efficiency between Sutures). Given their emphasis on this aspect (as well as being supported by the OSATS assessment), preliminary investigations were conducted on its feasibility and found it to be consistently significant in regression analyses. As such, this metric was incorporated into the overall assessment. By incorporating LDLJApp alongside metrics calculated during active suturing time, the aim was to reduce prediction errors and achieve a more meaningful understanding of suturing skills. This bivariate approach mitigates issues of highly correlated metrics and enables focused discussion of individual metric-skill associations. Consequently, regression models were constructed as:

$$\text{Rating}_{ij} = \beta_{o,i} + \beta_{1,i}LDLJ_{App,j} + \beta_{2,i}\text{metric}_{ij} + \varepsilon_{ij},$$

$$\varepsilon_{i,j} = \Sigma N(0, \sigma_i^2)$$

Where i indexes the metric and j is the individual observation for that metric.

4 Results

This study aimed to identify the most influential metrics for assessing surgical skill by analyzing their relationship with expert ratings through linear regressions with the metric LDLJApp. LDLJApp's strong effect sizes with expert ratings highlight the suitability of this approach, making it possible to analyze the individual contributions of the different metrics to suturing skill assessment.

Figure 23:
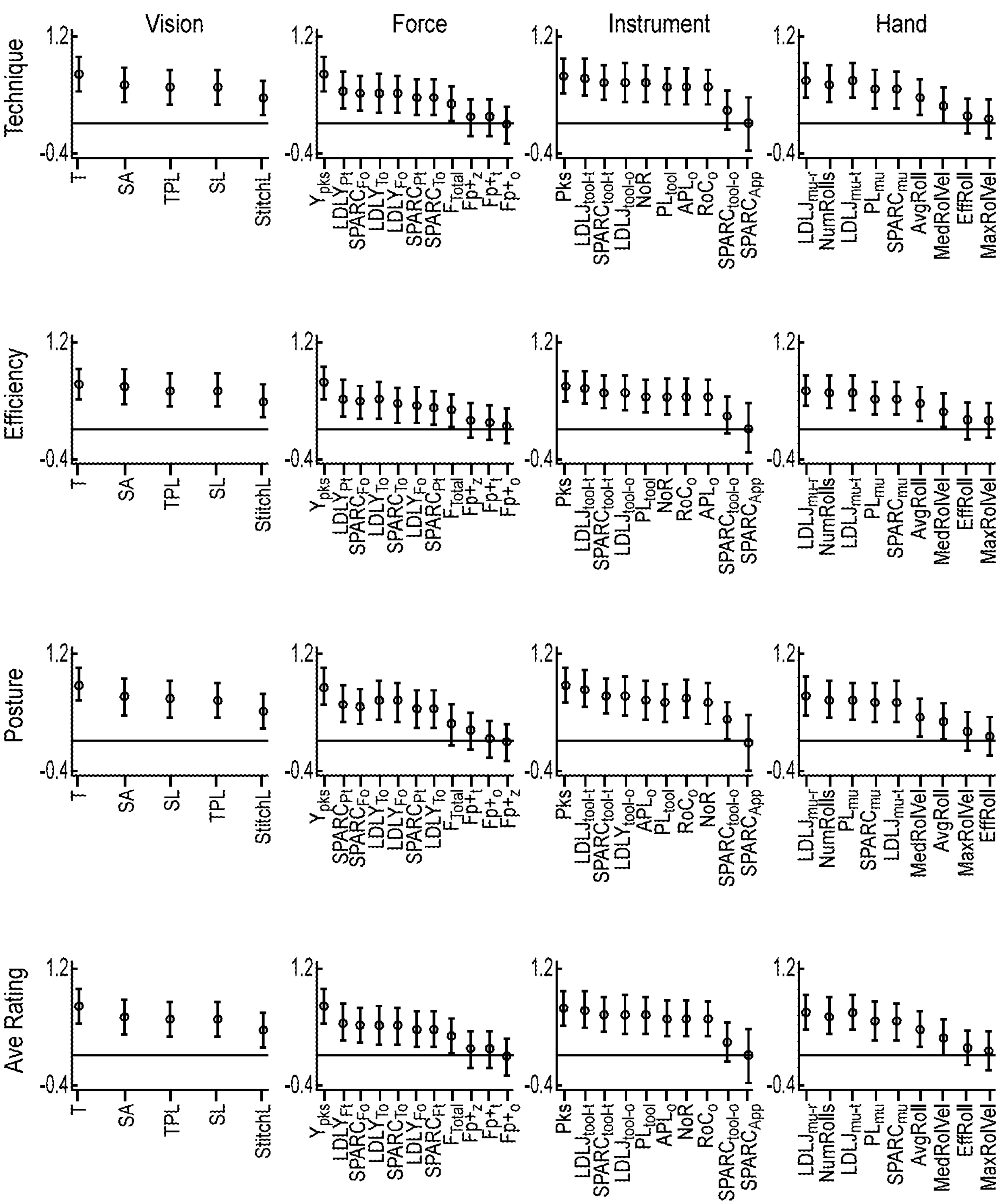
FIG. 23 shows the estimated coefficients and 95% confidence intervals for each individual metric and LDLJapp regressed with expert ratings, according to one embodiment.

The regression analysis results for each sensor are visualized in FIG. 23 for vision, instrument handling, hand kinematics, and membrane force/torque metrics, respectively. These figures display linear regression coefficients and 95% confidence intervals for each metric, ordered by best fit from R2. The R2 from the linear regressions allow for a direct comparison of the variance explained by each metric, whereas the coefficient may not necessarily imply improved performance. Notably, each sensing modality yielded valuable metrics with strong R2 values within the statistical model, with the top performers listed in Table 17. T, despite being a computer vision metric, is considered distinct from the four established sensor suites and is included as a fifth metric for comparison in this table. Detailed information on coefficient numbers and R2 fits for the metrics are tabulated in the Supplementary Materials.

TABLE 15

| Sensor and Description | Metric | Metric Description |
|---|---|---|
| Vision<br>A camera (Intel RealSense d435) placed within the membrane holder recorded subcutaneous needle movement at 60 FPS [28]. Metrics were computed based on detected pixels converted to millimeters, and suture needle tip data was filtered with a discrete-time low-pass filter at 15 Hz | Time (T) | Total time to complete the suture. |
| | Swept Area (SA) | The area covered by the body of the needle. |
| | Sway Length (SL) | Orthogonal needle sway distance. |
| | Tip Path Length (TPL) | The distance covered by the needle tip. |
| | Stitch Length (StitchL) | The length of suture thread after the needle exits the membrane. |
| Membrane Force/Torque<br>A force/torque sensor (ATI Mini40) was affixed to the bottom of the cylinder, measuring force and torque in the x, y, and z directions at 1000 Hz. Forces and torque were transformed into orthogonal (lateral) and tangential (longitudinal) directions. Each metric was applied to these directions and orthogonal torque, denoted with$_{o}$, $_{t}$, and $_{To}$. To compare with previous studies, maximum and minimum forces were applied in the z direction rather than orthogonal torque. | Maximum Force (Fp+) | The maximum applied force. |
| | Minimum Force (Fp−) | The minimum applied force. |
| | Total Force ($F_{total}$) | The cumulative sum of time series changes in force, similar to PL. |
| | Number of Yank Peaks ($Y_{pks}$) | The number of peaks in yank, the first derivative of force. |
| | Log Dimensionless Yank (LDLY) | A modified calculation of LDLJ to find smoothness of yank. |
| | $SPARC_F$ | SPARC applied to force. |

TABLE 16

| Sensor and Description | Metric | Metric Description |
|---|---|---|
| Instrument Handling<br>To assess a trainee's instrument handling ability, two electromagnetic EM position and orientation sensors (Ascension trakSTAR Model 180, Northern Digital Inc.) were affixed to both handles of the needle driver (Titanium, Mayo Hegar, 8"). The sensors recorded x, y, and z position and azimuth, elevation, roll, and quaternion orientation values with a sampling rate of 100 Hz. The tooltip location was estimated through a rotation calibration. As both sensors observed similar results in our previous work, data from one sensor was used in this study. Further details on the tooltip estimation process, calibration, custom attachments, metric formulas, and filtering are found in [21]. | Path Length ($PL_{tool}$) | Total distance covered by the tooltip. |
| | Number of Velocity Peaks (Pks) | The number of peaks in the tooltip's velocity profile with a minimum prominence of 0.05. |
| | Log Dimensionless Jerk ($LDLJ_{imu}$) | The natural log of jerk integrated and squared, made dimensionless through T and PL or APL. |
| | Spectral Arc Length ($SPARC_{imu}$) | The arc length of the Fourier transform of the velocity profile. |
| | Angular Path Length (APL) | The total angular distance traveled by the tool. |
| | Rate of Angular Change (RoC) | The average rate of change in rotation. |
| | Number of Rotations (NoR) | The number of deliberate tool rotations to complete a suture. |
| | Tool Smoothness between Sutures ($LDLJ_{App}$ [21]) | A measure of needle driver tip smoothness between sutures, specifically the second tertile. This metric was designed to assess the subject's control of their needle driver when not actively suturing and is hypothesized to measure their confidence. |
| Hand Kinematics<br>An IMU (Xsens MTw Awinda) placed on the dorsum and the wrist of the subject's dominant hand recorded angular velocity and linear acceleration sampled at 120 Hz. | Number of Rolls (NumRolls) | The number of intentional and unintentional roll motions. |
| | Average Roll Angle (AvgRoll) | The average roll angle of all roll motions found in NumRolls. |
| | Effective Roll (EffRoll) | The total forward roll distance traveled during suturing. |
| | Max Roll | The peak roll-axis angular velocity. |

TABLE 16-continued

| Sensor and Description | Metric | Metric Description |
|---|---|---|
| Previous work on the SutureCoach validated metrics obtaines from the hand IMU. See Shayan et al. (2023) for further details on data processing, filtering, and metric formulas. [20]. | Velocity (MaxRollVel) | |
| | Median Roll Velocity (MedRollVel) | The median roll-axix angular velocity. |
| | $LDLJ_{imu}$ | LDLJ calculated from roll-axis angular velocity and linear acceleration |
| | $SPARC_{imu}$ | SPARC calculated from roll-axis angular velocity. |
| | $PL_{imu}$ | The distance traveled by the hand. |

TABLE 17

| | Technique | | Efficiency | | Posture | | Ave Rating | |
|---|---|---|---|---|---|---|---|---|
| Metric | Coeff | $R^2$ | Coeff | $R^2$ | Coeff | $R^2$ | Coeff | $R^2$ |
| T | −0.704 | 0.492 | −0.656 | 0.553 | −0.833 | 0.497 | −0.731 | 0.537 |
| $Y_{pks}$ | −0.678 | 0.478 | −0.632 | 0.540 | −0.781 | 0.464 | −0.697 | 0.516 |
| Pks | −0.641 | 0.468 | −0.605 | 0.535 | −0.777 | 0.476 | −0.674 | 0.515 |
| $LDLJ_{imu-r}$ | −0.609 | 0.447 | −0.539 | 0.497 | −0.636 | 0.391 | −0.595 | 0.465 |
| SA | −0.541 | 0.422 | −0.580 | 0.526 | −0.621 | 0.392 | −0.581 | 0.466 |

5 Discussion

This study investigated the relationship between sensor-derived metrics and expert evaluations of suturing skill on the simulator platform. The analysis revealed that each sensor contributed at least one metric that was significantly associated with the experts' ratings. Additionally, several newly developed metrics within each sensor modality achieved significant and large effect sizes compared with traditional skill measures.

5.1 LDLJApp

The discussion begins with LDLJApp, which was developed in prior work to specifically target an aspect of suturing skill-Efficiency between Sutures—not captured by the other measures used in this study. We previously demonstrated LDLJApp's effectiveness in differentiating expert surgeons from intermediate residents. LDLJApp demonstrated large effect sizes with the Efficiency between Sutures category, validating its inclusion in the regression analysis by assessing an important facet of suturing skill as rated by experts. The metrics' inclusion reduced prediction errors compared to isolated regression analyses of metrics evaluated during active suturing time, allowing for a more meaningful analysis of the individual metric associations with expert ratings. These results suggest LDLJApp use as a valuable measure for surgical skill assessment, offering a unique perspective on factors influencing performance.

5.2 Time

T, a popular metric for surgical skill assessment, demonstrated a strong relationship with expert ratings, potentially reflecting a combination of subject confidence and overall efficiency in suturing. However, the measure's inability to differentiate expert attending surgeon and resident performance in previous studies reinforces the need for metrics that better convey personalized feedback tailored to the trainee's level rather than solely relying on time as a measure of competency.

5.3 Vision Metrics

Although vision metrics demonstrated statistically significant relationships with expert ratings across all categories, their goodness-of-fit measures (R2) were generally low compared to the best metrics in other sensors. These metrics, focused on quantifying subcutaneous needle movement, offer valuable insights into unnecessary needle movement and potential tissue damage. This crucial aspect of suturing is not directly observed by the experts, potentially explaining the low R2 with respect to expert ratings. However, significant differences were observed between many of these metrics when comparing means between different levels of clinical expertise (see relevant figure in the Supplementary Materials). For example, while the vision metric SA exhibited less fit compared to the other top metrics in the study (Table 17), the importance of minimizing needle movement and the significant group skill-level differences in vision metric scores still validate the metrics' importance for evaluating suturing skill. In this regard, vision metrics hold the potential for objectively evaluating this critical yet elusive aspect of surgical skill.

5.4 Instrument Handling Metrics

Instrument handling metrics displayed significant coefficients and high fits with expert ratings. The analysis revealed that tooltip motion metrics exhibit relatively higher R2 than rotational metrics. Specifically, three metrics consistently stood out: Pks, LDLJt, and SPARCt. Pks, a simpler smoothness measure, and the more robust smoothness measures of LDLJt and SPARCt capture unsteady tooltip motion. The rotational metrics LDLJo, LDLJr, and NoR showed promise with values slightly lower than SPARCt. In a previous study, it was observed that rotational motion measures were more consistent in differentiating expert attending surgeon and intermediate resident performance. The current study suggests, however, that expert assessors assess the smooth, translational movements that are readily observable compared to the subtler and perhaps imperceptible nature of rotational motions. During the pilot rating sessions, expert raters commented on minimizing rotations during suturing for effective technique. Thus, despite differences in R2, the fits of both rotational and translational instrument handling metrics demonstrate their applicability for assessing suturing skills.

5.5 Hand Kinematics Metrics

While the hand kinematics metrics focusing on rudimentary motion aspects (such as peak or median velocity) showed low R2 with expert ratings, metrics like LDLJimu-r, LDLJimu-t, and NumRolls displayed stronger associations. These metrics capture the smoothness of the hand's rotational and translational movements (LDLJimu-r and LDLJimu-t) and the frequency of hand roll reversals (NumRolls), suggesting that experts assess the controlled and smooth nature of hand motions. These results align with a previous study, where these metrics effectively distinguished clinical experience in surface trials. Unlike the instrument handling metrics, where translational motion measures had better fits than rotational motion measures, both types of motion had similar coefficient values in this sensing modality. A potential reason for this is that evaluating the quality of hand rotations is visually easier to assess than the more nuanced quality of instrument rotation. Ultimately, these findings highlight the relevance of hand kinematics metrics for assessing suturing skills.

Interestingly, the direction of the coefficients reveals valuable insights into expert preferences, particularly for hand kinematics and instrument handling metrics. While the most significant metrics exhibit negative coefficients (i.e., higher metric scores correlate with lower ratings), two exceptions were observed. The first of these involves metrics related to rotational speed: the hand kinematics metric MedRollVel and instrument handling metrics RoCo and RoCr. Both metrics measure rotational speeds, and their positive coefficients suggest that experts prefer faster rotational speeds as an indicator of skill for assessment. However, previous studies found that medical residents had higher values in these three metrics than attending surgeons, who had higher values than subjects with no experience. This suggests that, while faster speeds might be an initial indicator of skill for experts to rate subjects, achieving this may come at the expense of accuracy for less experienced individuals. Attending surgeons may prioritize accuracy over raw speed, leading to a more controlled and deliberate approach.

Another exception occurs with AvgRoll, which reflects average hand angular distance across individual hand motions. The positive coefficient suggests experts prefer infrequent, deliberate rotational motions over frequent short motions, aligning with the concept of motion smoothness, a quality proven to be desirable in suturing tasks. These findings suggest that a balance between speed and control is crucial for achieving expert-assessed suturing proficiency.

5.6 Membrane Force/Torque Metrics

The single-instance force metrics (Fp+ and Fp-) demonstrated poor performance in their association with expert ratings, lacking statistical significance and exhibiting the lowest R2 values among all metrics. As Trejos et al. highlight, these metrics fail to capture the subtleties of force application, offering limited feedback for training. In addition, their inconsistency in distinguishing groups of clinical expertise in this dataset (see relevant figure in the Supplementary Materials) aligns with previous studies exhibiting their limitations for practical surgical skill analysis. Efficient force assessment requires metrics that analyze force throughout the suturing process, not isolated points.

Interestingly, improvements were found with Ftotal, demonstrating significant coefficients in all expert rating categories but Body Posture. LDLY and SPARCF demonstrated promise, with statistically significant relationships with respect to expert ratings, albeit with R2 values lower than most other metric regressions. As with the instrument handling rotational metrics, force smoothness metrics may be more challenging to assess visually by experts. However, substantial improvements in results were observed with Ypks, boasting R2 values near or equivalent to Pks and LDLJt. The stressed importance of minimizing force during suturing is underscored through these results, as Ypks outperforms all other metrics with its ability to capture the unsteady application of force.

It should be noted that the expert rating categories lacked a "respect for tissue" category, potentially impacting the force smoothness metrics regression R2 fits. In addition, the pleather membrane material, chosen for its skin-like realism, also differs from real tissue (e.g., porcine) in visually discerning tearing forces. Despite these limitations, the vast improvements observed in force smoothness metrics highlight their value in identifying areas of excessive force application that traditional force metrics likely miss, which is particularly relevant given the prevalence of bleeding in vascular surgery. These metrics offer targeted feedback to improve aspects of force application in suturing skills by capturing subtle force variations through metrics like Ypks and LDLY.

This study explored the potential of combining sensor-based metrics with expert ratings for a more comprehensive and objective assessment of suturing skills. While expert assessments using GRS have been widely used in surgical skill evaluation, accurately capturing subtle nuances in performance-like instrument rotation, applied force, or subcutaneous needle movement—is challenging to assess through human observation. These limitations, combined with time constraints faced by expert surgeons, restrict trainees' ability to receive targeted feedback for consistent skill improvement. In this context, medical training simulators with instrumented sensors offer immense potential. These sensors can capture subtle aspects of performance indiscernible by visual perception, providing objective and quantifiable assessment measures. By validating these sensor-based metrics against expert assessments, the aim was to refine the simulator for a more robust and informative evaluation of open suturing skills.

Notably, key metrics within each category performed similarly, demonstrating their effectiveness in capturing crucial aspects of skill. To further explore the effectiveness of the different sensor metrics for skill assessment, their ability to distinguish average population scores was compared between levels of clinical experience. It was found that metrics that captured more "abstract" suturing skill, like the smoothness of instrument rotation or applied force, consistently distinguished between the more experienced groups (e.g., attending surgeons vs. residents) but exhibited smaller effect sizes compared to metrics that were more easily observable, like instrument tip smoothness or time. However, these more easily observable metrics could not differentiate the finer skill levels. Interestingly, hand kinematics metrics did not exhibit this behavior, with metrics with larger effect sizes being better at finer skill levels. The analysis revealed significant associations between sensor-based metrics and expert ratings across all sensor types, showcasing the potential for a multi-modal, comprehensive suturing skill assessment on the simulator system.

EXAMPLE 5

Well-developed surgical skills are crucial for optimal patient outcomes. While surgical training simulators offer objective sensor-based skill assessment, research has primarily focused on minimally invasive procedures with a distinct lack of open surgical skills assessment.

This study addresses this gap in medical education research by developing an automated system for assessing and training open vascular suturing skills using the simulator platform, which incorporates multiple sensors to comprehensively measure skill. Methods were developed to classify expert-rated subject performance on the simulator system using advanced sensor metrics. Further, a foundation was established for an algorithm that provides feedback for training.

Our findings demonstrate the value of aggregating performance across sutures for subject-based classification, achieving higher accuracies compared to individual suture analysis. Additionally, the system successfully delivers targeted feedback based on specific suture performance, This work highlights the importance of comprehensive, multimodal skill assessment for a more complete evaluation of a surgical procedure.

I. Introduction

The well-established link between surgical proficiency and patient outcomes underscores the necessity for efficient methods of surgical skills training. Expert assessment serves as the benchmark for skill evaluation, offering invaluable insights and comprehensive evaluations that have been shown to improve trainee performance. Notably, a study demonstrated that subjects receiving high expert ratings experienced reduced operative time and decreased postoperative complication rates. However, inherent limitations of subjectivity can impede this approach, especially when evaluating subjects of higher skill. This is particularly concerning in vascular surgery, where inadequate skills can lead to bleeding, a major complication in this field. Given these limitations, automated, objective assessment of surgical skills is crucial for the optimal development of medical education.

Surgical simulators create controlled environments ideal for objective assessment. These environments offer repeatable tasks designed to hone skills specific to a surgical procedure or field. This allows for the development of standardized curricula, such as the Fundamentals of Endovascular Surgery (FEVS) and the Fundamentals of Vascular Surgery (FVS). The American Board of Surgery's requirement of the Fundamentals of Laparoscopy (FLS) exam for board certification highlights the growing need for such methods of skill assessment. Consequently, a crucial challenge in surgical simulation lies in developing objective skill classification: can the simulator effectively judge a subject as skilled or unskilled?

Simulators can be interfaced with objective sensors to generate metrics to classify a subject's performance. The emergence of machine learning and neural networks shifted the surgical education paradigm to leverage sensor metrics in conjunction with these algorithms for automated assessment. While neural networks demonstrate higher accuracies compared to machine learning algorithms, challenges like requiring extensive datasets and the existence of the "black box" phenomenon (where the network's decision-making process is unknown) hinder standardization. Therefore, established machine learning algorithms offer a more transparent foundation for the validity of automated assessment through neural network approaches. However, prior to implementing a machine learning approach, simulators need to demonstrate that generated metrics can accurately assess clinically relevant technical skills for practical training and feedback.

Sensor metrics can be validated by differentiating between population groups or correlating them with clinical expertise. While these inferences serve as an initial step toward metric validation, a subject's performance can vary depending on the specific conditions of the simulated procedure, muddying the analysis of sensor metrics against broad categorizations of skill. As a result, a measure of current trial completion, such as an expertly assessed trial rating, becomes valuable for further validating metric relevance. Expert assessment often utilizes structured Global Rating Scales (GRS), which offer a customizable, versatile approach across various surgical fields. However, this assessment method is labor-intensive and time-consuming for the experts. To achieve a balance between leveraging expert knowledge and reducing their burdens, surgical simulators can combine GRS scores with machine learning. Supervised machine learning classifiers can be trained on sensor metrics from pre-labeled subjects evaluated using GRS scores, enabling automated skill assessment for consistent and practical training.

Studies in surgical skill assessment favor complex algorithms like Support Vector Machines (SVMs) due to their superior accuracy and ability to handle correlated features (metrics). SVMs classify data by determining a hyperplane for optimal separation of classes, accounting for nonlinear data by mapping features into a higher-dimensional space. However, the high-dimensional analysis can be difficult to interpret, impeding the model's capabilities for generating actionable feedback to improve trainee skills. In contrast, decision trees excel in interpretability by classifying data through a series of clear, metric-based decisions. This transparency makes these algorithms well-suited for providing targeted feedback on surgical skills. Holden et al. (2019) implemented this concept in their study on ultrasound-guided needle insertion. Their work applied importance to the decision tree's variable split for plain language feedback, highlighting how decision trees can be used to generate actionable insights for skill improvement.

While decision trees offer advantages in interpretability, several factors influence the successful implementation of any machine learning models for surgical skills assessment. Feature selection is crucial for establishing a model's relevancy and improving its capabilities, as performance can degrade with increasing features. Haung et al. (2019) demonstrated this importance by using Linear Discriminant Analysis (LDA) to categorize the educational background of surgeons, achieving accuracies of 43.4% for post-graduate year (PGY), 79.1% for research training years, and 64.2% for clinical training years with specific metric combinations. Similarly, Brown et al. (2020) implemented recursive feature training with logistic regression to identify effective metrics for classifying robot-assisted surgery skills, achieving up to 90% accuracy. Both studies emphasize the importance of a precise selection of metrics and the use of appropriate models to provide targeted feedback.

Additionally, Lam et al. (2022) identified key limitations when building machine learning classifiers for surgical skills assessment in a review of studies incorporating these algorithms. The authors found that many studies lacked sufficient sample sizes for effective implementation of machine learning approaches, with twenty out of sixty-six reviewed studies analyzing a dataset of under 10 participants. The authors further identified a lack of generalizability and standardization in many studies, impacted by factors such as diverse methodology for sensor measurement, assessed surgical procedure, and the definition of expertise for labeling. Lam et al. recommended addressing these limitations by standardizing methodologies and focusing on informative feedback mechanisms. They emphasize that implementing machine learning algorithms should prioritize targets for improvement, allowing trainees to improve their skill accordingly.

In light of these considerations, this study aims to determine whether it is possible to classify different levels of surgical skill on the simulator system, a multi-modal platform designed to comprehensively measure open suturing performance through various sensors. Previous studies have identified complex metrics suited for population differences from these sensors and their association with expert ratings on the simulator system. The goal is to leverage these findings as a foundation for building an effective classifier for surgical skill assessment and training using the simulator system.

II. Methods

A. Simulator Overview and Subject Demographics

The simulator platform assesses suturing skill on twelve sutures arranged in a radial, clock-face pattern (FIG. 24A) performed under simulated surface and depth conditions, representing suturing at a superficial level and an anatomical depth level. The twelve suture locations are laser-etched onto a pleather membrane secured to the top of a hollow cylinder. 97 subjects of varying clinical expertise completed four trials on the simulator system: a surface trial, a depth trial, then a repetition of the two (FIG. 24B). This analysis focuses on the subjects' second surface trials, which were rated by the expert surgeon collaborators. An error during data collection created falsely biased resting forces. Consequently, these trials were removed from this analysis, resulting in a remaining 94 trials (attending surgeons=25, fellows=9, residents=31, no medical experience=29). By synchronizing various sensors to the simulator, the aim is to comprehensively assess suturing skills. However, before detailing sensor information and features for classification, it is imperative to discuss the concept of motion smoothness and its consistent, successful applications in the various simulator system sensors.

B. Smoothness as a Measure of Clinical Performance

Smoothness of motion is a widely used measure of surgical skill assessment. While smoother motions may not directly translate to ideal suturing (e.g., smooth hand or needle driver motions do not guarantee proper suturing technique), research suggests a consistent link between smoothness and skilled performance. As surgeons develop their skills, their movements tend to become smoother.

In previous studies analyzing simulator system sensor data, formulations of motion smoothness were applied not only to translational motion but also to rotational motion, quality of applied membrane forces, and needle driver smoothness of a subject in between sutures. The results revealed the high applicability of formulations, as these measures could distinguish between attending surgeons and residents and were found to be significantly associated with expert ratings. The concept of smoothness is valuable in measuring subtle performance variations across different domains in surgical skill assessment, not limited to the original application of smoothness in motion.

1) Assessing Rotational Motion Smoothness for Suturing: In the history of motion smoothness, two metrics serve as robust, advanced quantifications of smoothness: log dimensionless jerk (LDLJ), a measure of variation in jerk, and spectral arc length (SPARC), a frequency-based measurement of velocity. By design, these measures are made dimensionless, independent of time and amplitude, meaning that a motion results in the same value regardless of the duration and amplitude of the movement. Traditionally, LDLJ and SPARC have generally been applied to linear tool or hand movements for surgical skills assessment. However, as suturing requires primarily rotational motions to complete the suture, adapting traditional motion metrics to rotational motion holds promise for suturing skills assessment. Recognizing this, Sharon et al. introduced a new metric, rate of orientation change (RoC), to assess the quality of such motions on a needle driver during open suturing. Their study successfully differentiated between experts and novices open needle driving motions with this measure and angular displacement,-referred to as angular path length (APL) on the simulator system. Melendez-Calderon et al. further demonstrated the applicability of LDLJ and SPARC to rotational movements using IMUs. These measures were successfully incorporated into the suturing simulator, differentiating between intermediate residents and expert surgeons based on both needle driver and hand rotations.

2) Smoothness (Efficiency) between Sutures: Beyond measuring active performance, smoothness can be used to assess the controlled motions of a subject when approaching a procedure. Inspired by interactions with clinical collaborators, measures were developed to assess the "approach efficiency" of a subject. Although previous studies have explored using idle time as a measure, the collaborators emphasized the subject's confidence and lack of hesitation when approaching the next suture, concepts reflected in motion smoothness' assessment of movement variability. This behavior was quantified by calculating LDLJ of needle driver tip motions between sutures (LDLJApp), with previous research demonstrating its potential for suturing skill assessment. This measure was the only needle driver translational measure to differentiate between resident and attending surgeon performance in that study, and large effect sizes were further observed when regressed against expert ratings of suturing performance. This approach to evaluating suturing performance demonstrates the value of assessing aspects beyond active procedural time.

3) Evaluating Force Smoothness: Force measurement in surgical simulation often lacks the detailed analysis seen with motion. Single-instance metrics like maximum force are sensitive to outliers and offer limited feedback. Studies have shown that these metrics fail to consistently capture differences in performance between residents and surgeons. Recognizing these limitations, Trejos et al. explored metrics that quantify the entire force profile, developing dimensionless smoothness measures applied to the first through third force derivatives. Building on their work, force smoothness calculations were refined due to advancements in the field to quantify the quality of applied forces in an earlier work on the simulator system. In this previous work, measures of motion smoothness were adapted to the first derivative of force, coined as yank by Lin et al. (2019), developing the metrics log dimensionless yank (LDLY) and spectral arc length of force (SPARCF). See Singh et al. (2024b) for the formulation of these metrics. These measures distinguished average performance between residents and surgeons on the simulator system, whereas the single-instance force metrics could not.

C. Simulator System Sensors and Metrics

The following subsections provide an overview of sensor information and metrics for suturing classification. Further detail on metric definitions and formulas can be found in a previous study analyzing the association of these metrics with expert ratings on the dataset. For effective classification of suturing skill, a selection of metrics proven to be significantly associated with the expert ratings were incorporated.

Subcutaneous needle tracking.

Needle driver position and orientation.

Hand orientation.

Membrane force.

External camera and expert ratings.

1) Subcutaneous Needle Tracking: A camera housed within the cylinder tracks needle tip position and needle body movement at each suture location at 60 fps. Minimizing subcutaneous needle movement is ideal to prevent tissue and membrane damage. To quantify this behavior, the computer vision features were calculated: needle swept area (SA), needle sway length (SL), thread stitch length (StitchL), and needle tip path length (TPL). The camera plays the most crucial role in the simulator as all metrics are calculated based on initial contact before needle entry to needle exit.

2) Needle Driver Position and Orientation Measurement: Two electromagnetic sensors attached to the needle driver handles measure x, y, and z Cartesian position and azimuth, elevation, roll, and quaternion orientation at a rate of 100 Hz (FIG. 24D). Rotation calibration estimates needle driver tip position, resulting in two domains of motion measurement: translational tip motion and orientational motion, denoted with t and o, respectively, or tool-t and tool-o if the same features were used in other sensors. For translational motion, path length (PLtool), number of velocity peaks (Pks), LDLJtool-t, SPARCtool-t, and the recently developed metric LDLJApp were used. For rotational motion, APLo, RoCo, LDLJtool-o, and SPARCtool-o were calculated, and the number of needle driver rotations (NOR). In the analysis, metrics applied to roll/x angular velocity performed similarly to those applied to overall orientation. Therefore, metrics were applied to the overall needle driver orientation for broader applicability in surgical skill assessment.

3) Hand Orientation Measurement: An IMU placed on the subject's hand measures linear acceleration, angular velocity, and Euler orientation at 120 Hz. While similar to needle driver motion metrics, these features capture distinct aspects of surgical skill, as it was observed that surgeons with specific techniques opt to rotate the needle driver with their fingers while exhibiting minimal hand movement. Similar to tool motion, metrics in this sensor were calculated on hand translational motion and hand roll rotational motion, denoted with imu-t and imu-r, respectively. The features pertaining to this domain include the number of hand rolls (NumRolls), average hand roll (AvgRoll), SPARC applied to IMU x angular velocity (SPARCimu), LDLJ applied to IMU position obtained from integrated acceleration data and x angular velocity (LDLJimu-t and LDLJimu-r), and path length applied to IMU position (PLimu).

4) Membrane Force Measurement: A force/torque sensor affixed to the bottom of the cylinder measures force and torque in x, y, and z directions at 1000 Hz. For a more valuable analysis, forces in x and y were transformed into lateral (orthogonal, o) and tangential (along the needle, t) based on suture location information obtained from the internal camera (FIG. 24C). Additionally, as forces in the zdirection were affected by both the needle and needle driver tip during suturing, torque was transformed to calculate forces about the main suture driving axis (orthogonal, To). Thus, the force features used in this study were LDLYTo and SPARCTo (orthogonal torque), LDLYt and SPARCFt (tangential force), LDLYo and SPARCFo (orthogonal force), and the number of peaks in yank (Ypks).

5) External Camera and Expert Ratings: An external camera records subject suturing performance at 30 fps. The camera was positioned to minimize identifying participant information. Four expert vascular surgeon educators rated the second surface trial of the 97 participants, with each participant rated by two surgeons. The experts considered the categories of Suture Technique, Efficiency between Sutures, and Body Posture were sufficient to rate subjects based on the quality of the external camera videos (FIG. 24E). Additionally, scores were averaged across all three categories for an Average Rating. A previous study details the rating interface, categories, and results of metric associations with the expert ratings.

D. Building the Classification Model: Decision Tree Classification of Subject Skill Levels The standardization of skill classification of two labels (e.g., expert vs. novice) hinges on the definition of the grouped subjects. As the dataset analyzed in this study comprises subjects of varying levels of clinical expertise, it was decided to examine three different population splits:

A novice, first quartile split classifying no competency vs. low to high competency, aiming to classify subjects with no skill.

An intermediate, median split classifying no and low competency vs. moderate and high competency, categorizing subjects with a moderate amount of skill.

An expert, third quartile split classifying no to moderate competency vs. high competency, focusing on identifying highly skilled subjects.

TABLE 18

| | Clinical Expertise | | | |
|---|---|---|---|---|
| Quartiles | Attending | Fellow | Resident | Student |
| Suturing Technique | | | | |
| 0-1.66 | 1 | 1 | 2 | 20 |
| 1.66-2.98 | 6 | 0 | 10 | 7 |
| 2.98-3.73 | 9 | 3 | 9 | 2 |
| 3.73-5 | 9 | 5 | 10 | 0 |
| Efficiency between Sutures | | | | |
| 0-2.37 | 0 | 1 | 2 | 21 |
| 2.37-3.38 | 7 | 0 | 8 | 8 |
| 3.38-4.11 | 7 | 5 | 11 | 0 |
| 4.11-5 | 11 | 3 | 10 | 0 |
| Body Posture | | | | |
| 0-2.23 | 1 | 0 | 2 | 21 |
| 2.23-3.36 | 8 | 3 | 8 | 4 |
| 3.36-4.22 | 5 | 4 | 10 | 4 |
| 4.22-5 | 11 | 2 | 11 | 0 |
| Ave Rating | | | | |
| 0-1.99 | 0 | 1 | 2 | 21 |
| 1.99-3.20 | 8 | 1 | 7 | 7 |
| 3.20-3.98 | 6 | 4 | 12 | 1 |
| 3.98-5 | 11 | 3 | 10 | 0 |

The splits were chosen based on quartiles of the subjects' ratings, resulting in a unique split value per rating category. Table 18 presents a distribution of clinical expertise about these splits per rating category.

A previous analysis of the association of the sensor metrics with expert ratings showed that each sensor contributes unique and valuable information to quantifying suturing performance. Therefore, it was determined that a decision tree algorithm was most applicable to this study. Its inclusion made it possible to accommodate multiple correlated features while providing an interpretable decision-making process, thus allowing full use of the suite of metrics. In addition, the suture location and direction of the suture impact its difficulty. In previous studies, when comparing metric score differences between population groups of clinical expertise, suture location was accounted for in the pairwise comparisons. As a result, an entropy-based decision tree was trained independently at each location.

To optimize the performance of decision tree algorithm, a two-step process was employed to tune the hyperparameters of each location's tree and to test the performance of the trained models. First, the dataset was initially split into a=75/25 train-test split. Within the training set, Monte Carlo K-fold cross-validation (k=10 folds, i=100 iterations) was used to cycle through tree depths and cost complexity pruning alpha (ccp alpha) values to find a combination that yielded the highest accuracy across the folds. The modal (most frequent) tree depth and ccp alpha observed across the Monte Carlo iterations were chosen as the hyperparameters for each location. Consequently, tree depths of 1-3 were chosen per location, with a ccp alpha of 0.0.

Following hyperparameter tuning, the data was then resampled into a new=75/25 train-test split to find classification test accuracies. The decision tree models were trained on the new training set using the optimized hyperparameters. The performance of these models was evaluated by calculating the average classification accuracy across all suture locations.

To account for the variation in performance about the clock-face, a vote-counting analysis was applied to each trial to classify a subject's overall skill level rather than their individual sutures. Subjects were classified based on the majority vote of classified sutures, and ties were assigned the modal class (most frequent label). The accuracy of this vote count was then evaluated based on subject-level classification.

To ensure the robustness of the model's performance and to account for variation in testing accuracies, the testing procedure was repeated using Monte Carlo validation (i=1000). The average testing (suture-based) and vote counting (subject-based) accuracies were recorded.

Figure 25:
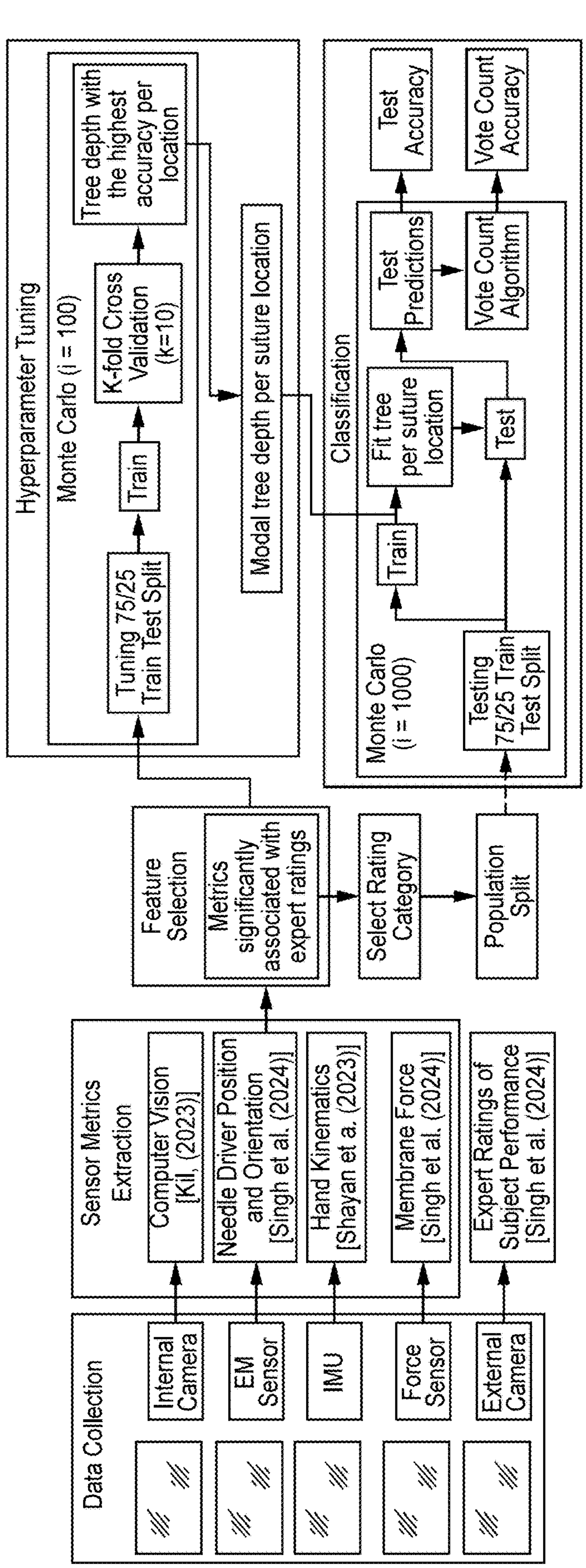
FIG. 25 is a flowchart depicting the decision tree classification process detailing the sensors, metrics extracted, feature selection, and classification algorithm, according to one embodiment.

This process was applied for all rating categories and repeated for the three splits. The relative efficacy of the algorithms were evaluated through Cohen's kappa coefficient, a measure of observed accuracy compared with a naïve accuracy of random chance. FIG. 25 illustrates a flowchart demonstrating the classification methodology.

III. Results

Table 19 summarizes each rating category's decision tree classification algorithm results, grouped by the population splits. Testing and vote count accuracies exhibited little variation across the categories in each split. Further, the vote count algorithm demonstrated notable improvements in accuracy across all skill splits, with an average increase of 9.27% in the novice split (unskilled=24, skilled=70), 7.04% in the median split (unskilled=47, skilled=47), and 6.97% in the expert split (unskilled=70, skilled=24).

Among the classification algorithms' classified accuracies, the novice split models achieved the highest vote count accuracies (average across all four categories=83.90%). Conversely, the intermediate split models displayed the lowest average accuracy (65.88%). However, while exhibiting seemingly good accuracies of =77%, the expert split models revealed poor classification results based on Cohen's kappa coefficient (FIG. 26). The coefficients for adjusted difference ranged from 0.04-0.17, indicating slight increases beyond chance. In comparison, the median split and novice split coefficients both range from 0.30-0.40. Overall, the classification algorithms implemented in the study effectively classified suturing skills across population splits, with the vote count enhancing classification accuracy.

IV. Discussion

A. Decision Tree Classification and Vote Counting

This study investigated the effectiveness of a decision tree algorithm for assessing surgical suturing skills on the platform. Multiple algorithms were trained based on different population splits of the data to evaluate their relative efficacy. A unique decision tree was trained at each suture location to account for variability in suture performance and salient metrics. A simple vote count algorithm was used to determine subject-based skill levels based on the most classified sutures in the trial. Ties were resolved by assigning the subject to the modal class.

The vote count yielded a significant improvement in accuracy over the training accuracy, aligning with a conclusion identified in. Experts evaluated subjects based on video recordings of their entire suturing trials. However, post-evaluation comments revealed that experts often skipped through the videos, observing performance for a few sutures before forming an overall impression. This subjective approach may be sufficient for identifying lower-skilled subjects but likely becomes less effective for distinguishing higher-skilled subjects. Fung et al. found that experts tend to rate based on overall performance rather than individual trials. This inherent subjectivity likely contributes to the lower observed classification test accuracies compared to the vote count. Further, accuracies did not vary across the rating categories within each population split, suggesting that experts may have provided overall subject ratings instead of a distinct score for each category. Similar results were observed in a previous study analyzing the association of sensor metrics with expert ratings, where metric associations with expert ratings did not vary across the categories. The results demonstrate that the vote count approach provides a more robust representation of a subject's skill, accounting for the global impressions made by experts and that subjects' performance can vary between sutures.

The decision tree algorithms demonstrated varying performance across the three population splits. The novice split yielded the highest classified accuracies. This suggests the algorithm can effectively classify subjects with no competency. Although the median split resulted in lower observed accuracies, Cohen's kappa coefficient values revealed that both classifiers achieved similar levels of effective classification beyond random chance. The final expert split initially demonstrated high classification accuracy, but Cohen's kappa coefficient indicates poor classification performance.

During the preliminary rating validation process, the surgeon collaborators commented on a subject's demeanor and attire before they started their first suture, potentially influencing their assessment. Christensen et al. observed that raters often evaluated "taste," a subjective evaluation of factors, due to ease of assessment. They found that raters might comment on proper task completion yet assign a lower score due to the subject's behavior, suggesting that expert performance evaluation is based on a combination of objective and subjective factors. Evaluations may be more subjective the higher subject's skill, as the minimum threshold for good performance has been reached.

This hypothesis is further supported by Yeates et al.'s work analyzing experts' qualitative commentary while assessing PGY 1 residents. Their work identified three themes: differential salience (placing different emphasis on various aspects), criterion uncertainty (assessment based on preconceived notions of competence), and information integration (unique narrative descriptions of skill). These factors can lead to stylistic ratings rather than objective assessments. While expert ratings are valuable for assessing performance, these stylistic preferences for subjects of higher skill, combined with the limitations of the expert rating interface, likely explain the challenges in classifying highly skilled subjects using the expert split.

B. Implementing the Classification Algorithms for User Feedback

The following section will discuss the implementation of this algorithm and interpretations of metrics for feedback based on the Average Rating category and the novice split for its superior accuracy. A flowchart demonstrating the methodology for feedback is seen in FIG. 27. This category was chosen due to ease of interpretation (one algorithm vs. four) and slight variation in results across the categories.: However, all categories were implemented into the simulator system for assessment.

TABLE 19

| Rating Category | Accuracy | | VC Errors | | Cohen's Kappa |
|---|---|---|---|---|---|
| | Test | VC | FP | FN | K |
| Novice (1st quartile) Split | | | | | |
| Technique (1.66) | 75.94% | 83.39% | 3.66 | 0.33 | 0.349 |
| Efficiency (2.37) | 75.57% | 82.13% | 3.98 | 0.29 | 0.300 |
| Posture (2.23) | 76.64% | 84.67% | 3.32 | 0.36 | 0.400 |
| Ave Rating (1.99) | 76.26% | 82.34% | 4.00 | 0.23 | 0.308 |
| Intermediate (Median) Split | | | | | |
| Technique (2.98) | 58.72% | 66.67% | 4.23 | 3.77 | 0.333 |
| Efficiency (3.38) | 60.80% | 69.83% | 3.72 | 3.52 | 0.397 |
| Posture (3.36) | 57.11% | 63.10% | 5.47 | 3.39 | 0.262 |
| Ave Rating (3.20) | 58.62% | 64.88% | 5.21 | 3.22 | 0.298 |
| Expert (3rd quartile) Split | | | | | |
| Technique (3.73) | 70.95% | 77.94% | 0.88 | 4.41 | 0.136 |
| Efficiency (4.11) | 72.23% | 78.84% | 0.69 | 4.38 | 0.171 |
| Posture (4.22) | 72.62% | 77.81% | 0.61 | 4.72 | 0.131 |
| Ave Rating (3.89) | 69.84% | 75.36% | 0.90 | 5.02 | 0.035 |

To evaluate the system for implementation on the simulator system, suture location decision trees were trained on a complete dataset excluding one subject. These trees used the same hyperparameters tuned for the Average Rating novice split (see FIG. 28 for each location's decision trees). The excluded subject's trial was then fed into the vote count algorithm. This algorithm classifies the subject as skilled or unskilled based on the majority classification of individual sutures. For the sutures classified as unskilled, the system extracts the specific metric-based decisions that classified the sutures as unskilled. This information is then translated into actionable feedback to guide improvement at those specific locations, presented in order of importance if multiple decisions contributed to the classification. The simulator platform emphasizes feedback when the subject is classified as unskilled. However, for skilled subjects, the system can optionally provide feedback on specific sutures classified as unskilled for further improvement.

C. Conclusion

In their review, Lam et al. (2022) emphasized the clinical value of classifying skill levels beyond novices, such as resident vs. attending surgeon performance, particularly as a novice may struggle to identify specific areas for improvement. While the study observed lower performance classifying high skilled subjects, decision trees were employed to address the feedback concerns. These trees provide actionable insights tailored to the trainee's performance at specific suture locations.

Figure 28:
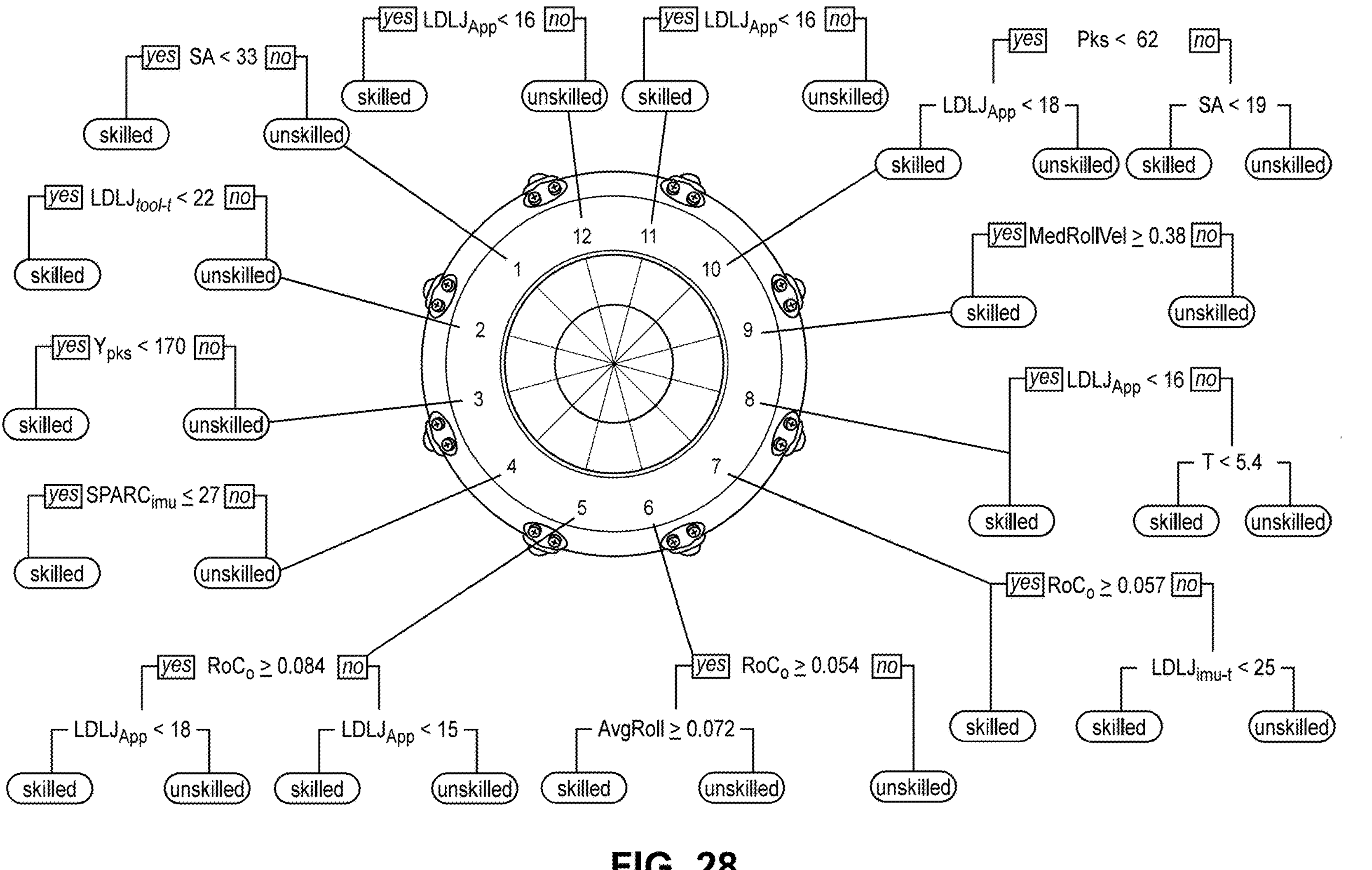
FIG. 28 is figure of the decision trees for each suture location based on average rating, according to one embodiment. Each sensor contributed metrics relevant to a suture location, demonstrating the value of a comprehensive assessment of skills through multi-modal sensors.

This study established a foundation for classifying overall suturing performance based on aggregate performance across all suture locations, recognizing the varying difficulty of the radial suture pattern. Furthermore, the simulator platform aims to provide comprehensive skill assessment through a multi-modal sensor interface. FIG. 28 exemplifies the value of this approach, as each sensor contributed to a decision-making process for a suture location. This study also underscores the importance of smoothness as a measure of surgical performance, as these measures have consistently been shown to be associated with suturing skills, and several of the decision trees in FIG. 28 incorporate a smoothness measure from one of the many sensors. In conclusion, this work lays the groundwork for developing advanced skill classification methods on the simulator platform. The high accuracies achieved with the vote count demonstrate the importance of an overall classification of skill based on segments of the trial. Future work will further enhance the decision tree algorithms developed in this study to refine the simulator system into a robust platform for measuring open vascular suturing skills.

While the various systems described above are separate implementations, any of the individual components, mechanisms, or devices, and related features and functionality, within the various system embodiments described in detail above can be incorporated into any of the other system embodiments herein.

The terms "about" and "substantially," as used herein, refers to variation that can occur (including in numerical quantity or structure), for example, through typical measuring techniques and equipment, with respect to any quantifiable variable, including, but not limited to, mass, volume, time, distance, wave length, frequency, voltage, current, and electromagnetic field. Further, there is certain inadvertent error and variation in the real world that is likely through differences in the manufacture, source, or precision of the components used to make the various components or carry out the methods and the like. The terms "about" and "substantially" also encompass these variations. The term "about" and "substantially" can include any variation of 5% or 10%, or any amount-including any integer-between 0% and 10%. Further, whether or not modified by the term "about" or "substantially," the claims include equivalents to the quantities or amounts.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 11/2, and 43/4 This applies regardless of the breadth of the range.

Although the various embodiments have been described with reference to preferred implementations, persons skilled in the art will recognize that changes may be made in form and detail without departing from the spirit and scope thereof.

What is claimed is:

1. A suturing simulation system comprising:

(a) an adjustable table;

(b) a membrane housing associated with the adjustable table;

(c) a suturing membrane attached to the membrane housing;

(d) an internal camera disposed within the membrane housing; and (e) a force/torque sensor operably coupled with the membrane housing, wherein the internal camera and the force/torque sensor are configured to collect suturing data.

2. The suturing system of claim 1, further comprising a motion sensor associated with the system, wherein the motion sensor is configured to collect suturing data.

3. The suturing system of claim 1, further comprising an external camera disposed above the membrane housing, wherein the external camera is configured to collect suturing data.

4. The suturing system of claim 1, further comprising a data collection software module configured to synchronize the suturing data from the internal camera and the force/torque sensor, thereby resulting in synchronized suturing data.

5. The suturing system of claim 4, wherein the data collection software module is configured to log the synchronized suturing data.

6. The suturing system of claim 5, further comprising a data processing software module configured to process image data in the synchronized suturing data.

7. The suturing system of claim 6, wherein the data processing software module is configured to extract metrics from the synchronized suturing data.

8. The suturing system of claim 1, further comprising at least one surgical depth cylinder removably positionable around the membrane housing.

9. The suturing system of claim 8, wherein the at least one surgical depth cylinder comprises a first surgical depth cylinder comprising a first height and a second surgical depth cylinder comprising a second height, wherein the second height is greater than the first height.

10. A suturing simulation and skills assessment system, comprising:

(a) a table comprising a height-adjustable tabletop;

(b) a membrane housing disposed through an opening in the tabletop, the membrane housing comprising a suturing membrane removably attached to the membrane housing;

(c) at least one removable surgical depth cylinder positionable around the membrane housing;

(d) an internal camera disposed within the membrane housing, wherein the internal camera is configured to collect suturing image data from an underside of the suturing membrane;

(e) at least one sensor associated with the table, wherein the at least one sensor is configured to collect suturing sensor data;

(f) a data collection software module configured to synchronize the suturing image data from the internal camera and the suturing sensor data from at least one sensor, thereby resulting in synchronized suturing data; and (g) a data processing software module configured process and extract metrics from the synchronized suturing data.

11. The suturing simulation and skills assessment system of claim 10, wherein the at least one sensor comprises a force/torque sensor operably coupled with the membrane housing.

12. The suturing simulation and skills assessment system of claim 10, wherein the at least one sensor comprises a motion sensor associated with the system, wherein the motion sensor is attachable to a hand or wrist of a user.

13. The suturing simulation and skills assessment system of claim 10, wherein the at least one sensor comprises a tool motion sensor associated with the system, wherein the tool motion sensor is attachable to a suturing tool.

14. The suturing simulation and skills assessment system of claim 10, further comprising an external camera disposed above the membrane housing, wherein the external camera is configured to collect suturing image data from a top side of the suturing membrane.

15. The suturing simulation and skills assessment system of claim 10, wherein the at least one removable surgical depth cylinder comprises a first surgical depth cylinder comprising a first height and a second surgical depth cylinder comprising a second height, wherein the second height is greater than the first height.

16. A method of assessing suturing skills of a user, the method comprising:

providing a simulation system comprising:

(a) a table comprising a height-adjustable tabletop;

(b) a membrane housing disposed through an opening in the tabletop, the membrane housing comprising a suturing membrane removably attached to the membrane housing;

(c) an internal camera disposed within the membrane housing;

(d) at least one sensor associated with the table;

(e) a data collection software module configured to synchronize the suturing image data from the internal camera and the suturing sensor data from at least one sensor, thereby resulting in synchronized suturing data; and (f) a data processing software module configured process and extract metrics from the synchronized suturing data;

having a user perform a suturing exercise on the suturing membrane;

collecting suturing image data relating to the suturing exercise from an underside of the suturing membrane via the internal camera;

collecting suturing sensor data relating to the suturing exercise via the at least one sensor;

synchronizing the suturing image data and the suturing sensor data, thereby resulting in synchronized suturing data;

processing and extracting metrics from the synchronized suturing data; and assessing a suturing skillset of the user via the metrics from the synchronized suturing data.

17. The method of claim 16, further comprising determining a depth of the suturing exercise by selecting a removable surgical depth cylinder based on a height of the at least one removable surgical depth cylinder and positioning the removable surgical depth cylinder around the membrane housing.

18. The method of claim 16, further comprising comparing the suturing skillset of the user to a suturing skillset of another user.

19. The method of claim 16, further comprising determining whether to certify the user based on the suturing skillset of the user.

20. The method of claim 16, further comprising providing feedback to the user based on the metrics from the synchronized suturing data.

* * * * *